(12) United States Patent
Wucherpfennig et al.

(10) Patent No.: US 10,993,971 B2
(45) Date of Patent: May 4, 2021

(54) VACCINATION WITH MICA/B ALPHA 3 DOMAIN FOR THE TREATMENT OF CANCER

(71) Applicant: Dana-Farber Cancer Institute, Inc., Boston, MA (US)

(72) Inventors: Kai W. Wucherpfennig, Brookline, MA (US); Soumya Badrinath, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 66 days.

(21) Appl. No.: 15/781,448

(22) PCT Filed: Dec. 5, 2016

(86) PCT No.: PCT/US2016/064969
§ 371 (c)(1),
(2) Date: Jun. 4, 2018

(87) PCT Pub. No.: WO2017/096374
PCT Pub. Date: Jun. 8, 2017

(65) Prior Publication Data
US 2018/0353581 A1 Dec. 13, 2018

Related U.S. Application Data

(60) Provisional application No. 62/422,454, filed on Nov. 15, 2016, provisional application No. 62/263,377, filed on Dec. 4, 2015.

(51) Int. Cl.
| | | |
|---|---|---|
| *A61K 39/02* | (2006.01) | |
| *A61K 36/74* | (2006.01) | |
| *A61K 39/00* | (2006.01) | |
| *A61K 35/74* | (2015.01) | |
| *C07K 16/12* | (2006.01) | |

(52) U.S. Cl.
CPC .......... *A61K 35/74* (2013.01); *A61K 39/0011* (2013.01); *A61K 39/105* (2013.01); *C07K 16/121* (2013.01); *A61K 2039/55522* (2013.01); *A61K 2039/55555* (2013.01); *A61K 2039/55561* (2013.01); *A61K 2039/6068* (2013.01); *A61K 2039/645* (2013.01)

(58) Field of Classification Search
CPC .......... A61K 2039/55522; A61K 2039/55555; A61K 2039/55561; A61K 2039/6068; A61K 2039/645; A61K 39/0011; A61K 39/001139; A61P 35/00
See application file for complete search history.

(56) References Cited

U.S. PATENT DOCUMENTS

| | | |
|---|---|---|
| 4,709,017 A | 11/1987 | Collier et al. |
| 4,950,740 A | 8/1990 | Greenfield et al. |
| 5,073,627 A | 12/1991 | Curtis et al. |
| 5,843,711 A | 12/1998 | Collier et al. |
| 5,917,017 A | 6/1999 | Collier et al. |
| 6,455,673 B1 | 9/2002 | Collier |
| 7,094,598 B2 | 8/2006 | Nabel et al. |
| 8,110,196 B2 | 2/2012 | Deem et al. |
| 8,889,044 B2 | 11/2014 | Yano et al. |
| 9,402,905 B2 | 8/2016 | Wucherpfennig et al. |
| 9,937,249 B2 | 4/2018 | Kim et al. |
| 2012/0264599 A1 | 10/2012 | Komatsu et al. |
| 2012/0269721 A1 | 10/2012 | Weng et al. |
| 2014/0086890 A1 | 3/2014 | Childs et al. |

FOREIGN PATENT DOCUMENTS

| | | |
|---|---|---|
| EP | 0378881 | 7/1990 |
| EP | 0372501 | 10/1990 |
| EP | 0427347 | 5/1991 |
| EP | 0471177 | 2/1993 |
| EP | 0594610 | 5/1994 |
| WO | 91/01146 | 2/1991 |
| WO | 93/17712 | 9/1993 |
| WO | 94/03208 | 2/1994 |
| WO | 98/18930 | 5/1998 |
| WO | 98/58668 | 12/1998 |
| WO | 03/37105 | 6/2000 |
| WO | 00/56360 | 9/2000 |
| WO | 00/61761 | 10/2000 |
| WO | 01/72337 | 10/2001 |
| WO | 02/91998 | 11/2002 |
| WO | WO 03/094849 A2 | 11/2003 |
| WO | 2006/067632 | 6/2006 |
| WO | 2008/036981 | 5/2008 |
| WO | 2013/049517 | 4/2013 |
| WO | WO 2013/117647 A1 | 8/2013 |
| WO | 2014/144791 | 9/2014 |
| WO | WO 2014/140904 A2 | 9/2014 |
| WO | WO 2015/139020 A2 | 9/2015 |

OTHER PUBLICATIONS

Skolnick et al. Trends in Biotechnology, 18: 34-39, 2000.*
Rudinger J. In: Peptide Hormones. (Ed) JA Parsons, University Park Press, pp. 1-7, 1976.*
Greenspan et al. Nature Biotechnology 17: 936-937, 1999.*
Parmiani G. et al., Cancer Immunotherapy With Peptide-Based Vaccines: What have we Achieved? Where are we going? Journal of the National Cancer Institute, Jun. 5, 2002, vol. 94, No. 11, pp. 805-818.
Baraldo et al. (2004) Infect Immun 72; 4884-7.
W.A.Pearson, Rapid and Sensitive Sequence Comparison with FASTP and FASTA, Meth. Enzymology, 1990 183:63-98, ed. R. Doolittle, Academic Press, San Diego.
D. Bordo and P. Argos, Suggestions for "Safe" Residue Substitutions in Site-Directed Mutagensis, 1991 J. Mol. Biol. 217:721-729.
Falugi et al (2001) Eur J Immunol 31; 3816-3824.
FDA's CDER Data Standards Manual version 004.
Hermeling, Suzanne, et al. "Structure-immunogenicity relationships of therapeutic proteins." Pharmaceutical research 21.6 (2004): 897-903.
Kuo et al (1995) Infect Immun 63; 2706-13.
Li, P. et al., Nat Immunol. May 2001;2(5):443-51.

(Continued)

*Primary Examiner* — Sarvamangala Devi
(74) *Attorney, Agent, or Firm* — Baker Donelson

(57) ABSTRACT

The present invention provides compositions and methods for treating cancer in a subject by eliciting an immune response against an MIC alpha 3-domain polypeptide.

15 Claims, 27 Drawing Sheets

Specification includes a Sequence Listing.

(56) References Cited

OTHER PUBLICATIONS

Lopez-Sagaseta J. et al., Self-assembling protein nanoparticles in the design of vaccines. Comput Struct Biotechnol J., Nov. 26, 2015, vol. 111, No. 14, pp. 58-68 p. 58.
M. S. Johnson and J. P. Overington, 1993, A Structural Basis for Sequence Comparisons: An Evaluation of Scoring Methodologies, J. Mol. Biol. 233:716-738.
W.R. Taylor, The Classification of Amino Acid Conservation, Theor. Biol. J. 1986 119:205-218.
Nicholls and Youle in Genetically Engineered Toxins, Ed: Frankel, Maecel Dekker Inc, 1992.
Parmiani G. et al., Opposite immune functions of GM-CSF administered as vaccine adjuvant in cancer patients. Annals of Oncology, Nov. 20, 2006, vol. 18, No. 2, pp. 226-232 p. 227.
Zhang, Y. and Orner, B.P., Self-Assembly in the Ferritin Nano-Cage Protein Super Family. 2011, Int. J. Mol. Sci., 12, 5406-5421.
Uchida et al J. Biol. Chem. 218; 3838-3844, 1973.
Vetter, C. S., et al. "Loss of nonclassical MHC molecules MIC-A/B expression during progression of uveal melanoma." British journal of cancer 91.8 (2004): 1495-1499.
Kim, J. et al. (2015) "Injectable, spontaneously assembling, inorganic scaffolds modulate immune cells in vivo and increase vaccine efficacy" *Nature Biotechnology*, 33(1):64-72; includes "Online Methods", doi:.1038/nbt.3071, 2 pages.

* cited by examiner

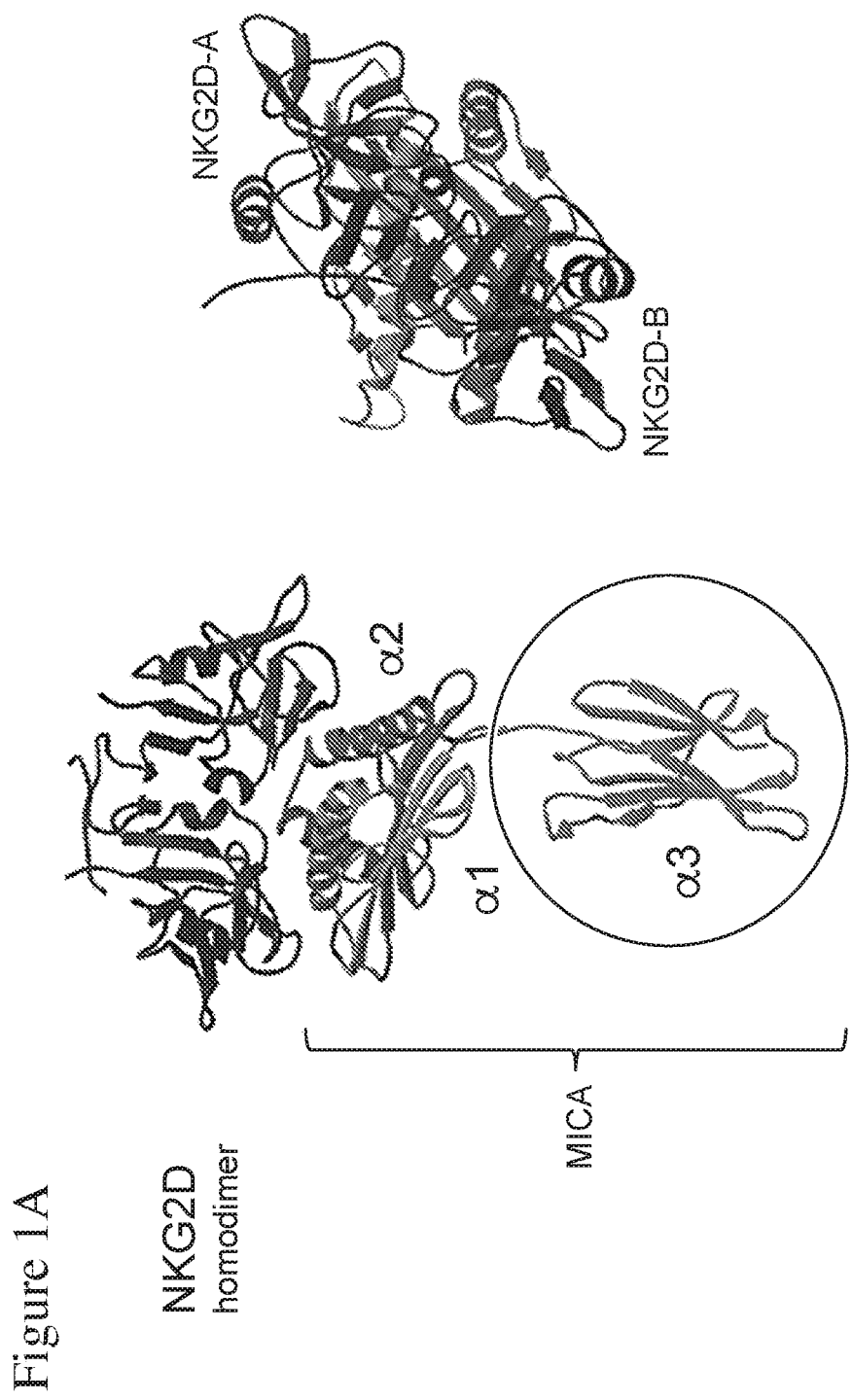

12.5 nm

Kaneyiko, M. et al. Nature, 2014.

H. pylori vs Mouse (L)   H. pylori vs Human (L)   Mouse (L) vs Human (L)

▨ Conserved  ▩ Not conserved

Kaneyiko, M. et al. Nature, 2014.

Construct design

Construct design

EM of MICA - ferritin particles

SDS-PAGE

Figure 20A
Figure 20B
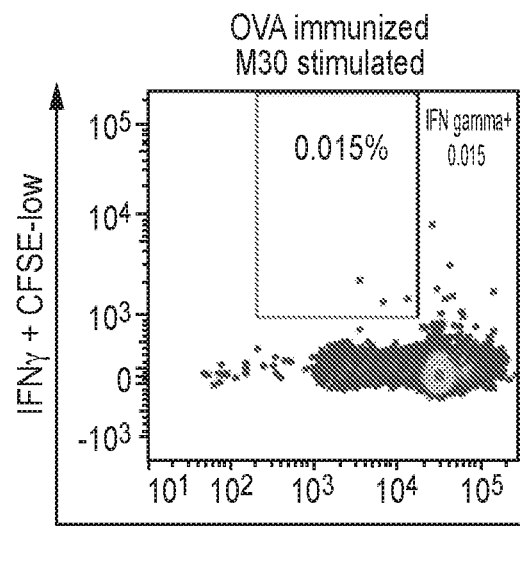
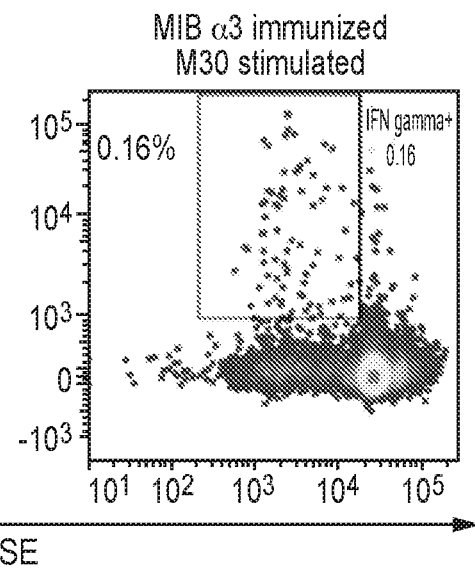
Figure 20C
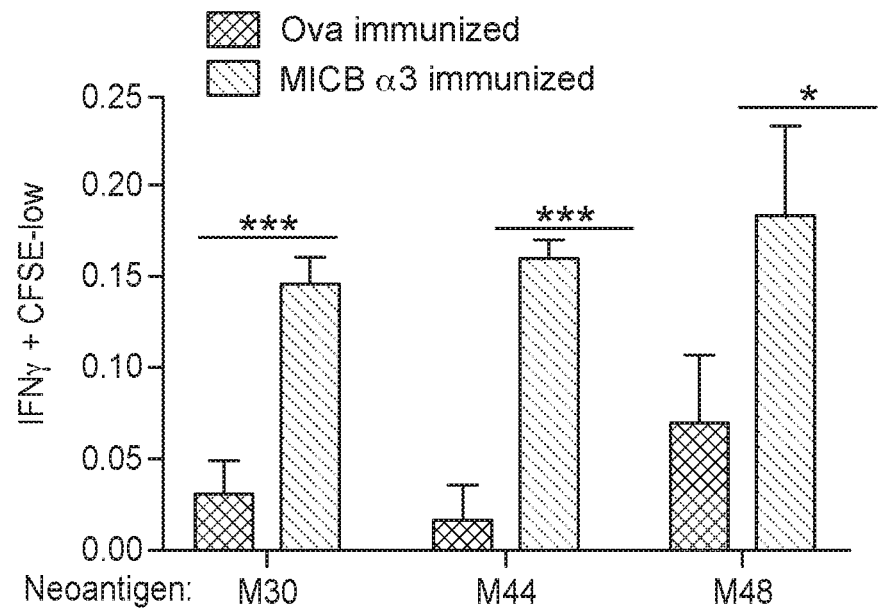

                        SEQUENCE LISTING

<160> NUMBER OF SEQ ID NOS: 30

<210> SEQ ID NO 1
<211> LENGTH: 360
<212> TYPE: PRT
<213> ORGANISM: Homo sapiens

<400> SEQUENCE: 1

His Ser Leu Arg Tyr Asn Leu Thr Val Leu Ser Trp Asp Gly Ser Val
1               5                   10                  15

Gln Ser Gly Phe Leu Ala Glu Val His Leu Asp Gly Gln Pro Phe Leu
            20                  25                  30

Arg Tyr Asp Arg Gln Lys Cys Arg Ala Lys Pro Gln Gly Gln Trp Ala
        35                  40                  45

Glu Asp Val Leu Gly Asn Lys Thr Trp Asp Arg Glu Thr Arg Asp Leu
50                  55                  60

Thr Gly Asn Gly Lys Asp Leu Arg Met Thr Leu Ala His Ile Lys Asp
65                  70                  75                  80

Gln Lys Glu Gly Leu His Ser Leu Gln Glu Ile Arg Val Cys Glu Ile
                85                  90                  95

His Glu Asp Asn Ser Thr Arg Ser Ser Gln His Phe Tyr Tyr Asp Gly
            100                 105                 110

Glu Leu Phe Leu Ser Gln Asn Val Glu Thr Glu Glu Trp Thr Val Pro
        115                 120                 125

Gln Ser Ser Arg Ala Gln Thr Leu Ala Met Asn Val Arg Asn Phe Leu
130                 135                 140

Lys Glu Asp Ala Met Lys Thr Lys Thr His Tyr His Ala Met His Ala
145                 150                 155                 160

Asp Cys Leu Gln Glu Leu Arg Arg Tyr Leu Glu Ser Ser Val Val Leu
                165                 170                 175

Arg Arg Thr Val Pro Pro Met Val Asn Val Thr Arg Ser Glu Ala Ser
            180                 185                 190

Glu Gly Asn Ile Thr Val Thr Cys Arg Ala Ser Ser Phe Tyr Pro Arg
        195                 200                 205

Asn Ile Thr Leu Thr Trp Arg Gln Asp Gly Val Ser Leu Ser His Asp
210                 215                 220

Thr Gln Gln Trp Gly Asp Val Leu Pro Asp Gly Asn Gly Thr Tyr Gln
225                 230                 235                 240

Thr Trp Val Ala Thr Arg Ile Cys Gln Gly Glu Glu Gln Arg Phe Thr
                245                 250                 255

Cys Tyr Met Glu His Ser Gly Asn His Ser Thr His Pro Val Pro Ser
            260                 265                 270

Gly Lys Val Leu Val Leu Gln Ser His Trp Gln Thr Phe His Val Ser
        275                 280                 285

Ala Val Ala Ala Ala Ala Ile Phe Val Ile Ile Phe Tyr
290                 295                 300

Val Arg Cys Cys Lys Lys Lys Thr Ser Ala Ala Glu Gly Pro Glu Leu
305                 310                 315                 320

Val Ser Leu Gln Val Leu Asp Gln His Pro Val Gly Thr Ser Asp His
                325                 330                 335
```

Arg Asp Ala Thr Gln Leu Gly Phe Gln Pro Leu Met Ser Ala Leu Gly
            340                 345                 350

Ser Thr Gly Ser Thr Glu Gly Ala
            355                 360

<210> SEQ ID NO 2
<211> LENGTH: 358
<212> TYPE: PRT
<213> ORGANISM: Homo sapiens

<400> SEQUENCE: 2

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Lys Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
210                 215                 220

Asn Thr Gln Gln Trp Gly Asp Val Leu Pro Asp Gly Thr Gly Thr Tyr Gln
225                 230                 235                 240

Thr Trp Val Ala Thr Arg Ile Arg Gln Gly Glu Glu Gln Arg Phe Thr
                245                 250                 255

Cys Tyr Met Glu His Ser Gly Asn His Gly Thr His Pro Val Pro Ser
            260                 265                 270

Gly Lys Ala Leu Val Leu Gln Ser Gln Arg Thr Asp Phe Pro Tyr Val
        275                 280                 285

Ser Ala Ala Met Pro Cys Phe Val Ile Ile Ile Leu Cys Val Pro
290                 295                 300

Cys Cys Lys Lys Lys Thr Ser Ala Ala Glu Gly Pro Glu Leu Val Ser
305                 310                 315                 320

Leu Gln Val Leu Asp Gln His Pro Val Gly Thr Gly Asp His Arg Asp
                325                 330                 335

```
Ala Ala Gln Leu Gly Phe Gln Pro Leu Met Ser Ala Thr Gly Ser Thr
            340                 345                 350

Gly Ser Thr Glu Gly Ala
        355
```

<210> SEQ ID NO 3
<211> LENGTH: 109
<212> TYPE: PRT
<213> ORGANISM: Artificial Sequence
<220> FEATURE:
<223> OTHER INFORMATION: Artificial polypeptide

<400> SEQUENCE: 3

```
Arg Thr Val Pro Pro Met Val Asn Val Thr Arg Ser Glu Ala Ser Glu
1               5                  10                  15

Gly Asn Ile Thr Val Thr Cys Arg Ala Ser Gly Phe Tyr Pro Trp Asn
            20                  25                  30

Ile Thr Leu Ser Trp Arg Gln Asp Gly Val Ser Leu Ser His Asp Thr
        35                  40                  45

Gln Gln Trp Gly Asp Val Leu Pro Asp Gly Asn Gly Thr Tyr Gln Thr
 50                  55                  60

Trp Val Ala Thr Arg Ile Ser Gln Gly Glu Glu Gln Arg Phe Thr Cys
65                  70                  75                  80

Tyr Met Glu His Ser Gly Asn His Ser Thr His Pro Val Pro Ser Gly
                85                  90                  95

Lys Val Leu Val Leu Gln Ser His Trp Gln Thr Phe His
            100                 105
```

<210> SEQ ID NO 4
<211> LENGTH: 109
<212> TYPE: PRT
<213> ORGANISM: Artificial Sequence
<220> FEATURE:
<223> OTHER INFORMATION: Artificial polypeptide

<400> SEQUENCE: 4

```
Arg Thr Val Pro Pro Met Val Gln Val Thr Arg Ser Glu Ala Ser Glu
1               5                  10                  15

Gly Gln Ile Thr Val Thr Cys Arg Ala Ser Gly Phe Tyr Pro Trp Asn
            20                  25                  30

Ile Asn Leu Ser Trp Arg Gln Asp Gly Val Ser Leu Ser His Asp Thr
        35                  40                  45

Gln Gln Trp Gly Asp Val Leu Pro Asp Gly Asn Gly Thr Tyr Gln Thr
 50                  55                  60

Trp Val Ala Thr Arg Ile Ser Gln Gly Glu Glu Gln Arg Phe Thr Cys
65                  70                  75                  80

Tyr Met Glu His Ser Gly Gln His Ser Thr His Pro Val Pro Ser Gly
                85                  90                  95

Lys Val Leu Val Leu Gln Ser His Trp Gln Thr Phe His
            100                 105
```

<210> SEQ ID NO 5
<211> LENGTH: 314
<212> TYPE: PRT
<213> ORGANISM: Artificial Sequence
<220> FEATURE:
<223> OTHER INFORMATION: Artificial polypeptide

<400> SEQUENCE: 5

```
Met Val Pro Cys Thr Leu Leu Leu Leu Ala Ala Leu Ala Pro
1               5                   10                  15

Thr Gln Thr Arg Ala His His His His His Ser Lys Ser Tyr Pro
            20                  25                  30

Tyr Asp Val Pro Asp Tyr Ala Arg Thr Val Pro Met Val Asn Val
                35                  40                  45

Thr Arg Ser Glu Ala Ser Glu Gly Asn Ile Thr Val Thr Cys Arg Ala
    50                  55                  60

Ser Gly Phe Tyr Pro Trp Asn Ile Thr Leu Ser Trp Arg Gln Asp Gly
65                  70                  75                  80

Val Ser Leu Ser His Asp Thr Gln Gln Trp Gly Asp Val Leu Pro Asp
                85                  90                  95

Gly Asn Gly Thr Tyr Gln Thr Trp Val Ala Thr Arg Ile Ser Gln Gly
                100                 105                 110

Glu Glu Gln Arg Phe Thr Cys Tyr Met Glu His Ser Gly Asn His Ser
            115                 120                 125

Thr His Pro Val Pro Ser Gly Lys Val Leu Val Leu Gln Ser His Trp
    130                 135                 140

Gln Thr Phe His Gly Ser Gly Asp Ile Ile Lys Leu Leu Asn Glu Gln
145                 150                 155                 160

Val Asn Lys Glu Met Gln Ser Ser Asn Leu Tyr Met Ser Met Ser Ser
                165                 170                 175

Trp Cys Tyr Thr His Ser Leu Asp Gly Ala Gly Leu Phe Leu Phe Asp
                180                 185                 190

His Ala Ala Glu Glu Tyr Glu His Ala Lys Lys Leu Ile Ile Phe Leu
            195                 200                 205

Asn Glu Asn Asn Val Pro Val Gln Leu Thr Ser Ile Ser Ala Pro Glu
    210                 215                 220

His Lys Phe Glu Gly Leu Thr Gln Ile Phe Gln Lys Ala Tyr Glu His
225                 230                 235                 240

Glu Gln His Ile Ser Glu Ser Ile Asn Asn Ile Val Asp His Ala Ile
                245                 250                 255

Lys Ser Lys Asp His Ala Thr Phe Asn Phe Leu Gln Trp Tyr Val Ala
            260                 265                 270

Glu Gln His Glu Glu Val Leu Phe Lys Asp Ile Leu Asp Lys Ile
        275                 280                 285

Glu Leu Ile Gly Asn Glu Asn His Gly Leu Tyr Leu Ala Asp Gln Tyr
    290                 295                 300

Val Lys Gly Ile Ala Lys Ser Arg Lys Ser
305                 310
```

<210> SEQ ID NO 6
<211> LENGTH: 945
<212> TYPE: DNA
<213> ORGANISM: Artificial Sequence
<220> FEATURE:
<223> OTHER INFORMATION: Artificial polynucleotide

<400> SEQUENCE: 6

```
atggtcccct gtaccctgct gctgctgctg gctgctgcac tggcacctac tcagactcgg      60
gcccaccatc atcaccatca ctcaaaaagt taccccctacg atgtccccga ctacgccagg    120
accgtgcccc ctatggtgaa cgtcacacgc tcagaagcta gcgagggcaa tatcaccgtg    180
acatgccgag catctgggtt ctatccttgg aacattacac tgagttggag gcaggacggg    240
```

-continued

```
gtgtccctgt ctcacgatac tcagcagtgg ggcgacgtgc tgccagatgg caatgggacc    300
taccagacat gggtggctac tcggatctcc caggggagg aacagagatt cacctgctat    360
atggagcata gtggaaacca ctcaacacat cctgtgccat ctggcaaggt gctggtcctg    420
cagagtcact ggcagacatt tcatggatca ggcgatatca ttaagctgct gaacgaacag    480
gtgaacaagg agatgcagtc tagtaacctg tacatgagca tgtcaagctg gtgttataca    540
cactccctgg acgagccgg cctgttcctg tttgatcacg ccgctgagga atacgaacat    600
gctaagaaac tgatcatttt cctgaatgag aacaatgtgc agtccagct gactagcatt    660 tccgcacccg aacacaagtt cgagggcctg acccagatct ttcagaaagc ctacgaacac    720
gagcagcata tctctgaaag tatcaacaac atcgtggacc acgcaatcaa gagcaaagat    780
catgccacct tcaactttct gcagtggtac gtggccgagc agcacgagga agaggtcctg    840
tttaaggaca ttctggataa aatcgaactg attggcaatg agaatcacgg gctgtacctg    900
gcagatcagt atgtcaaggg catcgcaaag tcaaggaaat catga                    945
```

<210> SEQ ID NO 7
<211> LENGTH: 314
<212> TYPE: PRT
<213> ORGANISM: Artificial Sequence
<220> FEATURE:
<223> OTHER INFORMATION: Artificial polypeptide

<400> SEQUENCE: 7

Met Val Pro Cys Thr Leu Leu Leu Leu Ala Ala Leu Ala Pro
1               5                   10                  15

Thr Gln Thr Arg Ala His His His His His Ser Lys Ser Tyr Pro
                20                  25                  30

Tyr Asp Val Pro Asp Tyr Ala Arg Thr Val Pro Pro Met Val Asn Val
            35                  40                  45

Thr Arg Ser Glu Ala Ser Glu Gly Asn Ile Thr Val Thr Cys Arg Ala
        50                  55                  60

Ser Gly Phe Tyr Pro Trp Asn Ile Thr Leu Ser Trp Arg Gln Asp Gly
65                  70                  75                  80

Val Ser Leu Ser His Asp Thr Gln Gln Trp Gly Asp Val Leu Pro Asp
                85                  90                  95

Gly Asn Gly Thr Tyr Gln Thr Trp Val Ala Thr Arg Ile Ser Gln Gly
            100                 105                 110

Glu Glu Gln Arg Phe Thr Cys Tyr Met Glu His Ser Gly Asn His Ser
        115                 120                 125

Thr His Pro Val Pro Ser Gly Lys Val Leu Val Leu Gln Ser His Trp
    130                 135                 140

Gln Thr Phe His Gly Ser Gly Asp Ile Ile Lys Leu Leu Asn Glu Gln
145                 150                 155                 160

Val Asn Lys Glu Met Gln Ser Ser Asn Leu Tyr Met Ser Met Ser Ser
                165                 170                 175

Trp Cys Tyr Thr His Ser Leu Asp Gly Ala Gly Leu Phe Leu Phe Asp
            180                 185                 190

His Ala Ala Glu Glu Tyr Glu His Ala Lys Lys Leu Ile Ile Phe Leu
        195                 200                 205

Asn Glu Asn Asn Val Pro Val Gln Leu Thr Ser Ile Ser Ala Pro Glu
    210                 215                 220

His Lys Phe Glu Gly Leu Thr Gln Ile Phe Gln Lys Ala Tyr Glu His
225                 230                 235                 240

Glu Gln His Ile Ser Glu Ser Ile Asn Asn Ile Val Asp His Ala Ile
                245                 250                 255

Lys Ser Lys Asp His Ala Thr Phe Asn Phe Leu Gln Trp Tyr Val Ala
            260                 265                 270

Glu Gln His Glu Glu Val Leu Phe Lys Asp Ile Leu Asp Lys Ile
        275                 280                 285

Glu Leu Ile Gly Asn Glu Asn His Gly Leu Tyr Leu Ala Asp Gln Tyr
    290                 295                 300

Val Lys Gly Ile Ala Lys Ser Arg Lys Ser
305                 310

<210> SEQ ID NO 8
<211> LENGTH: 945
<212> TYPE: DNA
<213> ORGANISM: Artificial Sequence
<220> FEATURE:
<223> OTHER INFORMATION: Artificial polynucleotide

<400> SEQUENCE: 8
atggtcccct gtaccctgct gctgctgctg gctgctgcac tggcacctac tcagactcgg      60
gcccaccatc atcaccatca ctcaaaaagt taccccctacg atgtccccga ctacgccagg    120
accgtgcccc ctatggtgaa cgtcacacgc tcagaagcta gcgagggcaa tatcaccgtg    180
acatgccgag catctgggtt ctatccttgg aacattacac tgagttggag caggacggg     240 gtgtccctgt ctcacgatac tcagcagtgg ggcgacgtgc tgccagatgg caatgggacc    300
taccagacat gggtggctac tcggatctcc caggggagg aacagagatt cacctgctat     360
atggagcata gtggaaacca ctcaacacat cctgtgccat ctggcaaggt gctggtcctg    420
cagagtcact ggcagacatt tcatggatca ggcgatatca ttaagctgct gaacgaacag    480
gtgaacaagg agatgcagtc tagtaacctg tacatgagca tgtcaagctg gtgttataca    540
cactccctgg acggagccgg cctgttcctg tttgatcacg ccgctgagga atacgaacat    600
gctaagaaac tgatcatttt cctgaatgag aacaatgtgc cagtccagct gactagcatt    660
tccgcacccg aacacaagtt cgagggcctg acccagatct ttcagaaagc ctacgaacac    720
gagcagcata tctctgaaag tatcaacaac atcgtggacc acgcaatcaa gagcaaagat    780
catgccacct tcaactttct gcagtggtac gtggccgagc agcacgagga agaggtcctg    840
tttaaggaca ttctggataa aatcgaactg attggcaatg agaatcacgg gctgtacctg    900
gcagatcagt atgtcaaggg catcgcaaag tcaaggaaat catga                    945

<210> SEQ ID NO 9
<211> LENGTH: 40
<212> TYPE: DNA
<213> ORGANISM: Artificial Sequence
<220> FEATURE:
<223> OTHER INFORMATION: Artificial polynucleotide

<400> SEQUENCE: 9
aaaaaacccg ggatggtccc ctgtaccctg ctgctgctgc                            40

<210> SEQ ID NO 10
<211> LENGTH: 50
<212> TYPE: DNA
<213> ORGANISM: Artificial Sequence
<220> FEATURE:
<223> OTHER INFORMATION: Artificial polynucleotide

```
<400> SEQUENCE: 10
gttcgttcag cagcttaatg atatcgcctg atccatgaaa tgtctgccag                  50

<210> SEQ ID NO 11
<211> LENGTH: 50
<212> TYPE: DNA
<213> ORGANISM: Artificial Sequence
<220> FEATURE:
<223> OTHER INFORMATION: Artificial polynucleotide

<400> SEQUENCE: 11
ctggcagaca tttcatggat caggcgatat cattaagctg ctgaacgaac                  50

<210> SEQ ID NO 12
<211> LENGTH: 43
<212> TYPE: DNA
<213> ORGANISM: Artificial Sequence
<220> FEATURE:
<223> OTHER INFORMATION: Artificial polynucleotide

<400> SEQUENCE: 12
aaaaaaggat cctcatgatt tccttgactt tgcgatgccc ttg                         43

<210> SEQ ID NO 13
<211> LENGTH: 10
<212> TYPE: DNA
<213> ORGANISM: Artificial Sequence
<220> FEATURE:
<223> OTHER INFORMATION: Artificial polynucleotide
<220> FEATURE:
<221> NAME/KEY: misc_feature
<222> LOCATION: (7)..(10)
<223> OTHER INFORMATION: n is a, c, g, or t

<400> SEQUENCE: 13 acctgcnnnn                                                              10

<210> SEQ ID NO 14
<211> LENGTH: 11
<212> TYPE: DNA
<213> ORGANISM: Artificial Sequence
<220> FEATURE:
<223> OTHER INFORMATION: Artificial polynucleotide
<220> FEATURE:
<221> NAME/KEY: misc_feature
<222> LOCATION: (4)..(8)
<223> OTHER INFORMATION: n is a, c, g, or t

<400> SEQUENCE: 14
gacnnnnngt c                                                            11

<210> SEQ ID NO 15
<211> LENGTH: 11
<212> TYPE: DNA
<213> ORGANISM: Artificial Sequence
<220> FEATURE:
<223> OTHER INFORMATION: Artificial polynucleotide
<220> FEATURE:
<221> NAME/KEY: misc_feature
<222> LOCATION: (4)..(8)
<223> OTHER INFORMATION: n is a, c, g, or t

<400> SEQUENCE: 15
cctnnnnnag g                                                            11
```

-continued

```
<210> SEQ ID NO 16
<211> LENGTH: 167
<212> TYPE: PRT
<213> ORGANISM: Helicobacter pylori

<400> SEQUENCE: 16

Met Leu Ser Lys Asp Ile Ile Lys Leu Leu Asn Glu Gln Val Asn Lys
1               5                   10                  15

Glu Met Gln Ser Ser Asn Leu Tyr Met Ser Met Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Ile Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Ser Lys
            100                 105                 110

Asp His Ala Thr Phe Asn Phe Leu Gln Trp Tyr Val Ala Glu Gln His
        115                 120                 125

Glu Glu Glu Val Leu Phe Lys Asp Ile Leu Asp Lys Ile Glu Leu Ile
    130                 135                 140

Gly Asn Glu Asn His Gly Leu Tyr Leu Ala Asp Gln Tyr Val Lys Gly
145                 150                 155                 160

Ile Ala Lys Ser Arg Lys Ser
                165

<210> SEQ ID NO 17
<211> LENGTH: 167
<212> TYPE: PRT
<213> ORGANISM: Helicobacter pylori

<400> SEQUENCE: 17

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Ile Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Ser Lys
            100                 105                 110

Asp His Ala Thr Phe Asn Phe Leu Gln Trp Tyr Val Ala Glu Gln His
        115                 120                 125

Glu Glu Glu Val Leu Phe Lys Asp Ile Leu Asp Lys Ile Glu Leu Ile
    130                 135                 140
```

Gly Asn Glu Asn His Gly Leu Tyr Leu Ala Asp Gln Tyr Val Lys Gly
145                 150                 155                 160

Ile Ala Lys Ser Arg Lys Ser
                165

<210> SEQ ID NO 18
<211> LENGTH: 429
<212> TYPE: DNA
<213> ORGANISM: Artificial Sequence
<220> FEATURE:
<223> OTHER INFORMATION: Artificial polynucleotide

<400> SEQUENCE: 18
atggtcccct gtaccctgct gctgctgctg gctgctgcac tggcacctac tcagactcgg    60
gcctcaaaaa gttaccccta cgatgtcccc gactacgcca ggaccgtgcc ccctatggtg    120
caggtcacac gctcagaagc tagcgagggc caaatcaccg tgacatgccg agcatctggg    180
ttctatcctt ggaacattaa cctgagttgg aggcaggacg gggtgtccct gtctcacgat    240
actcagcagt ggggcgacgt gctgccagat ggcaatggga cctaccagac atgggtggct    300
actcggatct cccagggggga ggaacagaga ttcacctgct atatggagca tagtggacag    360
cactcaacac atcctgtgcc atctggcaag gtgctggtcc tgcagagtca ctggcagaca    420
tttcattga                                                             429

<210> SEQ ID NO 19
<211> LENGTH: 429
<212> TYPE: DNA
<213> ORGANISM: Artificial Sequence
<220> FEATURE:
<223> OTHER INFORMATION: Artificial polynucleotide

<400> SEQUENCE: 19
atggtcccct gtaccctgct gctgctgctg gctgctgcac tggcacctac tcagactcgg    60
gcctcaaaaa gttaccccta cgatgtcccc gactacgcca ggaccgtgcc ccctatggtg    120
caggtcacac gctcagaagc tagcgagggc caaatcaccg tgacatgccg agcatctggg    180
ttctatcctt ggaacattaa cctgagttgg aggcaggacg gggtgtccct gtctcacgat    240
actcagcagt ggggcgacgt gctgccagat ggcaatggga cctaccagac atgggtggct    300
actcggatct cccagggggga ggaacagaga ttcacctgct atatggagca tagtggacag    360
cactcaacac atcctgtgcc atctggcaag gtgctggtcc tgcagagtca ctggcagaca    420
tttcattga                                                             429

<210> SEQ ID NO 20
<211> LENGTH: 142
<212> TYPE: PRT
<213> ORGANISM: Artificial Sequence
<220> FEATURE:
<223> OTHER INFORMATION: Artificial polypeptide

<400> SEQUENCE: 20

Met Val Pro Cys Thr Leu Leu Leu Leu Ala Ala Ala Leu Ala Pro
1               5                   10                  15

Thr Gln Thr Arg Ala Ser Lys Ser Tyr Pro Tyr Asp Val Pro Asp Tyr
                20                  25                  30

Ala Arg Thr Val Pro Pro Met Val Gln Val Thr Arg Ser Glu Ala Ser
            35                  40                  45

Glu Gly Gln Ile Thr Val Thr Cys Arg Ala Ser Gly Phe Tyr Pro Trp
        50                  55                  60

```
Asn Ile Asn Leu Ser Trp Arg Gln Asp Gly Val Ser Leu Ser His Asp
 65                  70                  75                  80

Thr Gln Gln Trp Gly Asp Val Leu Pro Asp Gly Asn Gly Thr Tyr Gln
                 85                  90                  95

Thr Trp Val Ala Thr Arg Ile Ser Gln Gly Glu Glu Gly Arg Phe Thr
            100                 105                 110

Cys Tyr Met Glu His Ser Gly Gln His Ser Thr His Pro Val Pro Ser
        115                 120                 125

Gly Lys Val Leu Val Leu Gln Ser His Trp Gln Thr Phe His
    130                 135                 140

<210> SEQ ID NO 21
<211> LENGTH: 10
<212> TYPE: DNA
<213> ORGANISM: Artificial Sequence
<220> FEATURE:
<223> OTHER INFORMATION: Artificial polynucleotide
<220> FEATURE:
<221> NAME/KEY: misc_feature
<222> LOCATION: (7)..(10)
<223> OTHER INFORMATION: n is a, c, g, or t

<400> SEQUENCE: 21 acctgcnnnn                                                          10

<210> SEQ ID NO 22
<211> LENGTH: 11
<212> TYPE: DNA
<213> ORGANISM: Artificial Sequence
<220> FEATURE:
<223> OTHER INFORMATION: Artificial polynucleotide
<220> FEATURE:
<221> NAME/KEY: misc_feature
<222> LOCATION: (4)..(8)
<223> OTHER INFORMATION: n is a, c, g, or t

<400> SEQUENCE: 22
gacnnnnngt c                                                        11

<210> SEQ ID NO 23
<211> LENGTH: 40
<212> TYPE: DNA
<213> ORGANISM: Artificial Sequence
<220> FEATURE:
<223> OTHER INFORMATION: Artificial polynucleotide

<400> SEQUENCE: 23
aaaaaaagat ctatggtccc ctgtaccctg ctgctgctgc                         40

<210> SEQ ID NO 24
<211> LENGTH: 40
<212> TYPE: DNA
<213> ORGANISM: Artificial Sequence
<220> FEATURE:
<223> OTHER INFORMATION: Artificial polynucleotide

<400> SEQUENCE: 24
aaaaaagaat tctcaatgaa atgtctgcca gtgactctgc                         40

<210> SEQ ID NO 25
<211> LENGTH: 142
<212> TYPE: PRT
<213> ORGANISM: Artificial Sequence
<220> FEATURE:
<223> OTHER INFORMATION: Artificial polypeptide
```

```
<400> SEQUENCE: 25

Met Val Pro Cys Thr Leu Leu Leu Leu Ala Ala Ala Leu Ala Pro
1               5                   10                  15

Thr Gln Thr Arg Ala Ser Lys Ser Tyr Pro Tyr Asp Val Pro Asp Tyr
                20                  25                  30

Ala Arg Thr Val Pro Pro Met Val Gln Val Thr Arg Ser Glu Ala Ser
            35                  40                  45

Glu Gly Gln Ile Thr Val Thr Cys Arg Ala Ser Gly Phe Tyr Pro Trp
    50                  55                  60

Asn Ile Asn Leu Ser Trp Arg Gln Asp Gly Val Ser Leu Ser His Asp
65                  70                  75                  80

Thr Gln Gln Trp Gly Asp Val Leu Pro Asp Gly Asn Gly Thr Tyr Gln
                85                  90                  95

Thr Trp Val Ala Thr Arg Ile Ser Gln Gly Glu Glu Arg Phe Thr
                100                 105                 110

Cys Tyr Met Glu His Ser Gly Gln His Ser Thr His Pro Val Pro Ser
            115                 120                 125

Gly Lys Val Leu Val Leu Gln Ser His Trp Gln Thr Phe His
        130                 135                 140

<210> SEQ ID NO 26
<211> LENGTH: 128
<212> TYPE: PRT
<213> ORGANISM: Artificial Sequence
<220> FEATURE:
<223> OTHER INFORMATION: Artificial polypeptide

<400> SEQUENCE: 26

Met Ala Pro Ala Arg Ser Pro Ser Pro Ser Thr Gln Pro Trp Glu His
1               5                   10                  15

Val Asn Ala Ile Gln Glu Ala Arg Arg Leu Leu Asn Leu Ser Arg Asp
                20                  25                  30

Thr Ala Ala Glu Met Asn Glu Thr Val Glu Val Ile Ser Glu Met Phe
            35                  40                  45

Asp Leu Gln Glu Pro Thr Cys Leu Gln Thr Arg Leu Glu Leu Tyr Lys
    50                  55                  60

Gln Gly Leu Arg Gly Ser Leu Thr Lys Leu Lys Gly Pro Leu Thr Met
65                  70                  75                  80

Met Ala Ser His Tyr Lys Gln His Cys Pro Pro Thr Pro Glu Thr Ser
                85                  90                  95

Cys Ala Thr Gln Ile Ile Thr Phe Glu Ser Phe Lys Glu Asn Leu Lys
            100                 105                 110

Asp Phe Leu Leu Val Ile Pro Phe Asp Cys Trp Glu Pro Val Gln Glu
    115                 120                 125

<210> SEQ ID NO 27
<211> LENGTH: 125
<212> TYPE: PRT
<213> ORGANISM: Artificial Sequence
<220> FEATURE:
<223> OTHER INFORMATION: Artificial polypeptide

<400> SEQUENCE: 27

Met Ala Pro Thr Arg Ser Pro Ile Thr Val Thr Arg Pro Trp Lys His
1               5                   10                  15

Val Glu Ala Ile Lys Glu Ala Leu Asn Leu Leu Asp Asp Met Pro Val
                20                  25                  30
```

```
Thr Leu Asn Glu Glu Val Glu Val Ser Asn Glu Phe Ser Phe Lys
         35                  40                  45
Lys Leu Thr Cys Val Gln Thr Arg Leu Lys Ile Phe Glu Gln Gly Leu
 50                  55                  60
Arg Gly Asn Phe Thr Lys Leu Lys Gly Ala Leu Asn Met Thr Ala Ser
 65                  70                  75                  80
Tyr Tyr Gln Thr Tyr Cys Pro Pro Thr Pro Glu Thr Asp Cys Glu Thr
                 85                  90                  95
Gln Val Thr Thr Tyr Ala Asp Phe Ile Asp Ser Leu Lys Thr Phe Leu
            100                 105                 110
Thr Asp Ile Pro Phe Glu Cys Lys Lys Pro Val Gln Lys
        115                 120                 125

<210> SEQ ID NO 28
<211> LENGTH: 781
<212> TYPE: DNA
<213> ORGANISM: Homo sapiens

<400> SEQUENCE: 28
acacagagag aaaggctaaa gttctctgga ggatgtggct gcagagcctg ctgctcttgg     60
gcactgtggc ctgcagcatc tctgcacccg cccgctcgcc cagccccagc acgcagccct    120
gggagcatgt gaatgccatc caggaggccc ggcgtctcct gaacctgagt agagacactg    180
ctgctgagat gaatgaaaca gtagaagtca tctcagaaat gtttgacctc caggagccga    240
cctgcctaca gacccgcctg agctgtaca agcagggcct gcggggcagc ctcaccaagc    300
tcaagggccc cttgaccatg atggccagcc actacaagca gcactgccct ccaaccccgg    360
aaacttcctg tgcaacccag attatcacct ttgaaagttt caaagagaac ctgaaggact    420
ttctgcttgt catccccttt gactgctggg agccagtcca ggagtgagac cggccagatg    480
aggctggcca agccggggag ctgctctctc atgaaacaag agctagaaac tcaggatggt    540
catcttggag ggaccaaggg gtgggccaca gccatggtgg gagtggcctg gacctgccct    600
gggccacact gaccctgata caggcatggc agaagaatgg gaatatttta tactgacaga    660
aatcagtaat atttatatat ttatattttt aaaatattta tttatttatt tatttaagtt    720
catattccat atttattcaa gatgttttac cgtaataatt attattaaaa atatgcttct    780
a                                                                    781

<210> SEQ ID NO 29
<211> LENGTH: 144
<212> TYPE: PRT
<213> ORGANISM: Homo sapiens

<400> SEQUENCE: 29

Met Trp Leu Gln Ser Leu Leu Leu Leu Gly Thr Val Ala Cys Ser Ile
  1               5                  10                  15
Ser Ala Pro Ala Arg Ser Pro Ser Pro Ser Thr Gln Pro Trp Glu His
             20                  25                  30
Val Asn Ala Ile Gln Glu Ala Arg Arg Leu Leu Asn Leu Ser Arg Asp
         35                  40                  45
Thr Ala Ala Glu Met Asn Glu Thr Val Glu Val Ile Ser Glu Met Phe
 50                  55                  60
Asp Leu Gln Glu Pro Thr Cys Leu Gln Thr Arg Leu Glu Leu Tyr Lys
 65                  70                  75                  80
Gln Gly Leu Arg Gly Ser Leu Thr Lys Leu Lys Gly Pro Leu Thr Met
                 85                  90                  95
```

```
Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
            130                 135                 140

<210> SEQ ID NO 30
<211> LENGTH: 20
<212> TYPE: DNA
<213> ORGANISM: Artificial Sequence
<220> FEATURE:
<223> OTHER INFORMATION: Artificial polynucleotide

<400> SEQUENCE: 30
tccatgacgt tcctgacgtt                                           20
```

VACCINATION WITH MICA/B ALPHA 3 DOMAIN FOR THE TREATMENT OF CANCER

RELATED APPLICATIONS

This application is a U.S. National Phase application, filed under 35 U.S.C. § 371, of International Application No. PCT/US2016/064969, filed on Dec. 5, 2016, which claims priority to and benefit of U.S. Provisional Application No. 62/263,377, filed on Dec. 4, 2015, and 62/422,454, filed on Nov. 15, 2016, the contents of each of which are hereby incorporated by reference in their entireties.

GOVERNMENT INTEREST

This invention was made with government support under R01CA173750 awarded by the National Institutes of Health. The government has certain rights in the invention.

INCORPORATION-BY-REFERENCE OF SEQUENCE LISTING

The contents of the text file named "DFCI-126_NO1US_SequenceListing_ST25.txt", which was created on May 31, 2018 and is 31 KB in size, are hereby incorporated by reference in their entireties.

FIELD OF THE INVENTION

The present invention relates generally to composition and methods for inducing an anti-tumor immune response in a subject.

BACKGROUND OF THE INVENTION

Recent advances in the field of cancer immunotherapy have demonstrated the ability of our immune system to eradicate even advanced cancers. These therapies are rapidly changing the face of cancer treatment. Unlike monoclonal antibody therapies which require repeated administration of antibodies to prevent tumor relapse, vaccines can induce endogenous immunological memory and thus have the potential to provide long-term protection.

The selection of antigens for vaccine therapy requires a comprehensive understanding of the biological role of the candidate antigens in tumor growth and their expression levels by tumor cells compared to normal tissues. MICA and the closely related MICB protein (abbreviated as MIC) are antigens that are absent or expressed at very low levels by normal cells, but are broadly upregulated by a variety of different cancers secondary to genomic damage. MIC is an important ligand for the NKG2D receptor on cytotoxic lymphocytes, specifically NK cells, CD8 T cells and gamma-delta T cells. Expression of MIC targets such cells for elimination by the immune system. However, many tumors are found to escape this important immune surveillance pathway by shedding MIC from the cell surface, a process in which the MIC alpha3 domain is unfolded by the disulfide isomerase ERp5 rendering it sensitive to cleavage by matrix metalloproteases such as ADAM 10 and ADAM 17. Shed MIC causes downregulation of the NKG2D receptor on NK cells and CD8 T cells. Proteolytic cleavage thus turns an immune-stimulatory protein into an immunosuppressive sub stance.

Thus a need exists for compounds to inhibit MICA shedding.

SUMMARY OF THE INVENTION

In various aspects, the invention provides vaccine compositions including as an immunogenic component, an effective amount of a peptide including the MIC alpha 3-domain. By effective amount means an amount effective to elicit an immune response against the MIC alpha 3-domain.

The MIC alpha 3-domain is a MICA or MICB alpha 3-domain. Optionally, the MIC alpha 3-domain is non glycosylated. Preferably, the peptide includes amino acid sequence of SEQ ID NO: 3 or SEQ ID NO: 4. In various aspects, the vaccine composition comprises a plurality of peptides. In some aspects, the peptide is conjugated to a carrier protein.

In another aspect, the invention provides a fusion protein having a monomeric ferritin subunit protein joined to a MIC alpha 3-domain protein. The monomeric ferritin subunit protein has a domain that allows the fusion protein to self-assemble into nanoparticles. In a preferred embodiment, the monomeric subunit is a *Helicobacter pylori* ferritin protein. Optionally, the fusion protein is further conjugated to a CpG oligonucleotide.

In yet another aspect, the invention provides a nanoparticle including the fusion protein according to the invention. The nanoparticle includes a plurality of MIC alpha 3-domain peptides.

In yet another aspect, the invention provides a vaccine composition comprising the nanoparticle according to the invention. The vaccine composition can further comprise GM-CSF.

In a further aspect the invention provides method of treating cancer in a subject by administering to a subject a vaccine composition according to the invention. Optionally, the vaccine composition contains GM-CSF. The subject has tested positive for shed MIC in their serum. The vaccine composition is administered as part of a therapeutic regimen. A therapeutic regimen includes for example, radiation therapy, targeted therapy, immunotherapy, or chemotherapy. Optionally, the subject is further administered one or more vaccines specific for an antigen other than a MIC alpha 3-domain antigen.

In another aspect the invention provides a method for treating cancer by administering to the subject a vaccine comprising cells that express MIC alpha-3 domain. In a further aspect the invention provides a method for treating cancer where an immune response against MIC is induced by use of a replicating or non-replicating virus.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 1A is a schematic that demonstrates the interaction between NKG2D homodimer and MICA. The MICA-alpha3 domain is identified for reference. From: Nat Immunol. 2001 May; 2(5):443-51. Complex structure of the activating immunoreceptor NKG2D and its MHC class I-like ligand MICA.

FIG. 2B further depicts (Right) an SDS gel under reducing conditions containing samples that were collected between 22 to 27 minutes at the protein peak.

FIG. 2D further depicts (Right) an SDS gel under reducing conditions containing samples that were collected between 16 to 20 minutes at the peak protein.

FIG. 5A depicts a FACS plot of MICAα3 specific antibodies in the sera of immunized mice to full length MICA expressed on the surface of B16F10 mouse melanoma cells. B16F10 melanoma cells were transfected with human MICA cDNA (allele 009) and then labeled with isotype control antibody (negative control) or a saturating concentration of a murine mAb specific for MICA (6D4, positive control). This system was then used to test sera from mice vaccinated with MICA α3—ferritin or a control antigen (OVA). A PE-labeled secondary anti-mouse IgG antibody was used to detected antibodies bound to the cell surface. Fluorescence was quantified by FACS. Strong staining was detected even with 1 µl of serum from mice on days 14-42 following vaccination. FIG. 5B depicts a bar graph of the mean fluorescence intensity (MFI) representing+/−SD of 3 replicates of binding of MICAα3 specific antibodies in the sera of immunized mice to full length MICA expressed on the surface of B16F10 mouse melanoma cells.

FIG. 8A demonstrates that immunization with MICA alpha3-ferritin prevents metastasis in comparison to naïve controls, or animals that received OVA-protein injection. FIG. 8B is a graph that demonstrates results obtained by ELISA which indicate that vaccinated mice had undetectable levels of sMICA (shed MICA) in the sera.

FIG. 11A is a graph that depicts the number of pulmonary metastases following vaccination with MICAα vaccine alone. FIG. 11B is a graph that depicts the amount of sMICA in the serum at day 0, day 5 and day 13 post vaccination with MICAα vaccine alone.

In FIG. 12A, 7 week old C57BL/6 female mice (n=8) were immunized with MICA-ferritin vaccine and boosted on day 12. The mice were challenged with subcutaneous injection of $0.5\times10^6$ B16F10 cells expressing MICA on day 25 after initial vaccination and the tumor volume was measured every other day. Tumor growth in the MICA-ferritin immunized group was found to be significantly slower (empty square) compared to the naïve, untreated age matched control group (filled circle). In FIG. 12B, sMICA levels were undetectable in sera of mice immunized with MICA-ferritin vaccine (empty triangle) while high levels of sMICA were detected within two weeks after tumor challenge in the sera of the non-immunized control group (filled triangle).

In FIG. 13A, 7 week old C57BL/6 female mice were immunized with MICA-ferritin vaccine (n=16) or with OVA control vaccine (n=8) and boosted on day 14. The mice were challenged with subcutaneous injection of $0.5\times10^6$ B16F10 cells expressing MICA on day 21 after initial vaccination. Mice received intravenous injection of 200 μg of anti-CD8 antibody (n=8) or isotype control antibody (n=8) 2 days prior to tumor challenge and twice a week thereafter at a dose of 100 μg per mouse until the study endpoint. Tumor volume was measured every other day. The mice were euthanized when the tumors reached ≥250 mm$^2$. Tumors reached their maximum volume by day 12 in OVA protein vaccinated control mice treated with CD8 antibody (empty triangle) and by day 14 in naïve, untreated, non-depleted control group (filled circle). CD8 depletion accelerated tumor growth in MICA-vaccinated group (filled triangle) compared to MICA-vaccinated group that received isotype antibody (empty square). In FIG. 13B, survival analysis of CD8 depletion experiment showing age matched naïve, untreated, non-depleted control group in thick solid line, OVA protein vaccinated group in thin dashed line, MICA-ferritin vaccinated, CD8 depleted in thick dashed line and MICA-ferritin vaccinated, isotype antibody injected mice in thin solid line.

In FIG. 14A, 7 week old C57BL/6 female mice were immunized with MICA-ferritin vaccine (n=16) and boosted on day 14. The mice were challenged with subcutaneous injection of $0.5\times10^6$ B16F10 cells expressing MICA on day 21 after initial vaccination. Mice received intravenous injection of 200 μg of anti-NK1.1 antibody (n=8) or isotype control antibody (n=8) 2 days prior to tumor challenge and twice a week thereafter at a dose of 100 μg per mouse until the study endpoint. Tumor volume was measured every other day. The mice were euthanized when the tumors reached ≥250 mm$^2$. Tumors reached their maximum volume by day 14 in naïve, untreated, non-depleted control group (filled circle). NK cell depletion accelerated tumor growth in MICA-vaccinated group (empty triangle) compared to MICA-vaccinated group that received isotype antibody (filled square). In FIG. 14B, survival analysis of NK cell depletion experiment showing age matched naïve, untreated, non-depleted control group in thick solid line; MICA-ferritin vaccinated, NK cell depleted in dashed line and MICA-ferritin vaccinated, isotype antibody injected mice in thin solid line.

In FIG. 15A, 8 week old Ighmtm1Cgn/J female mice (n=12) were challenged with intravenous injection of $0.5\times10^6$ MICA expressing B16F10 melanoma cells. The mice were randomized into 3 cohorts with 4 mice each. On days 1, 2, 4 and 6 after tumor challenge, the mice were injected (intraperitoneal route) with 100 μl of end point sera from naïve, OVA-protein or MICA-ferritin immunized C57BL/6 mice. Mice were euthanized 14 days after tumor challenge; lungs were harvested and fixed in 10% neutral-buffered formalin and the number of pulmonary metastases was quantified. Mice injected with sera from MICA-ferritin vaccinated group (empty square) had significantly fewer lung metastases compared to mice injected with sera from untreated, age matched control group (filled circle) and OVA-protein immunized group. In FIG. 15B, sMICA level was lower in mice receiving sera from MICA-ferritin vaccinated group (empty square) compared to mice receiving sera from naïve or OVA-protein immunized group.

In FIG. 16A, 7 week old C57BL/6 female mice (n=4) were immunized with MICA-ferritin vaccine and boosted on day 14. The mice were challenged with subcutaneous injection of $0.5\times10^6$ B16F10 cells expressing MICB on day 21 after initial vaccination and the tumor volume was measured every other day. B16F10-MICB tumor growth in the MICA-ferritin immunized group was found to be significantly slower (empty square) compared to the OVA-protein immunized control group (filled circle). In FIG. 16B, sMICB levels were nearly undetectable in sera of mice immunized with MICA-ferritin vaccine (empty square) while high levels of sMICB were detected within two weeks after tumor challenge in the sera of the OVA-protein immunized control group (filled circle).

FIGS. 20A-20C are a series of graphs showing that MICA-ferritin vaccine induces secondary T cell responses to neoantigens. We examined whether the MICB α3 domain vaccine induces secondary responses to tumor neoantigens. Lymph node T cells were labeled with CFSE and cultured for three days with four different neoantigen peptides previously identified for B16F10 tumors as CD4 T cell epitopes. CD4 T cell responses were identified for three of the four peptides based on intracellular IFNγ staining in proliferating cells (CFSE$^{low}$). We hypothesize that MICA antibodies trigger Fc receptor mediated uptake of apoptotic tumor fragments by dendritic cells and thereby promote T cell responses to neoantigens. In FIGS. 20A-20B, B6 mice were immunized with MICB α3—ferritin or OVA (n=5/group) and injected with B16F10-MICB tumor cells. T cells were isolated from tumor-draining lymph nodes 10 days after tumor implantation and labeled with CF SE. T cells were cultured for 3 days with CD11c+ spleen cells in the presence of four different CD4 neoantigen peptides (10 μg/ml) previously identified for B16F10 tumors. Intracellular IFNγ staining was performed and proliferating T cells (CF SE-low) positive for intracellular IFNγ were quantified. T cell responses to neoantigen peptides were compared between mice immunized with the OVA control antigen (FIG. 20A) or MICB α3 domain (FIG. 20B). Both T cell populations were incubated in vitro with the M30 neoantigen. In FIG. 20C, summary of T cell responses to three neoantigens (M30, M44 and M48) for which enhanced T cell responses were observed in MICB immunized mice.

In FIG. 21A, macaque MICAS-ferritin was conjugated to CpG ODN 1826 by CLICK chemistry (protein-oligo conjugation kit, Solulink). Briefly, S-HyNic (succinimidyl-6-hydrazino-nicotinamide) linker was conjugated to the protein through primary amines on the lysine and S-4B (succinimidyl-4-formylbenzamide) linker was added to CpG oligo. The modified protein and oligo were incubated in a catalyzed conjugation reaction. Following this reaction, excess of unconjugated CpG was removed by size exclusion chromatography. Protein-oligo conjugate bond (stable, bis-arylhydrazone bond) formed is UV traceable at 350 nm (see graph). In FIG. 21B, the CpG conjugated protein was used to immunize C57BL/6 mice. MICAS specific antibodies in the serum were analyzed on day 14 by labeling of B16-MICA cells. The CpG linked protein induced higher titer antibodies (thin solid line) compared to the MICA-ferritin protein formulated with the scaffold (dashed line; thick solid line demonstrates background staining levels).

DETAILED DESCRIPTION OF THE INVENTION

Figure 1B:
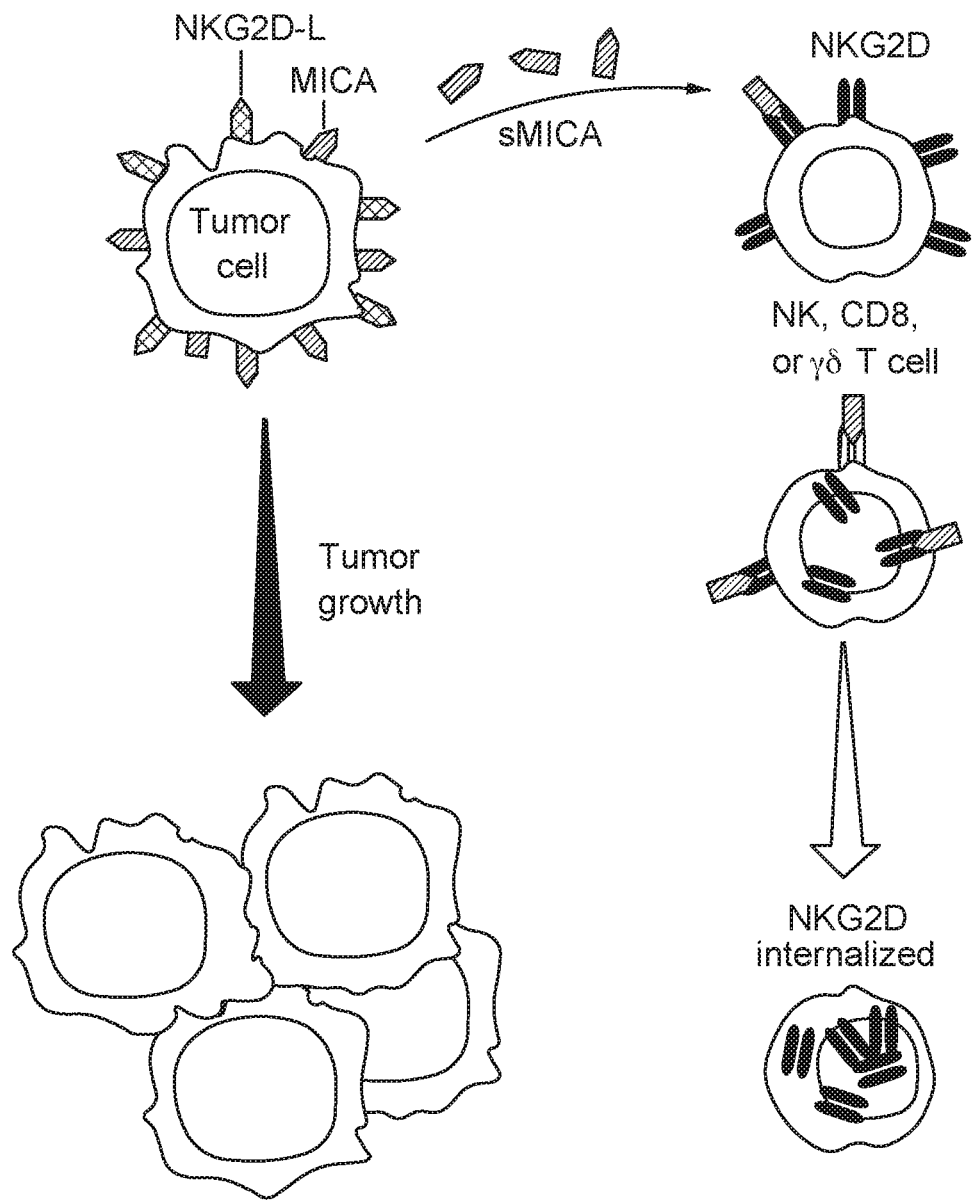
FIG. 1B is a schematic that demonstrates one mechanism through which tumors escape immune surveillance through the shedding of MIC from the tumor cells' surface.

The present invention provides a vaccine for cancer. More specifically, the present invention provides a MIC alpha 3-domain vaccine that can elicit an immune response against MIC alpha 3-domain. Importantly, the vaccine elicits antibodies against the MIC α3 domain, but not against the α1-α2 domains of MIC as not to interfere with the binding of the α1-α2 domains to the NKG2D receptor on NK cells.

The purpose of the vaccine is to induce polyclonal antibodies that bind to the membrane-proximal Ig domain of MICA and inhibit proteolytic shedding of this protein from tumor cells. The MICA alpha 3 domain was expressed on the surface of nanoparticles. Specifically, the MICA alpha 3 domain coding sequence was fused to the ferritin sequence (from *H. pylori*), given that ferritin spontaneously forms nanoparticles. The vaccine was formulated either with an immunization scaffold (mesoporous silica rods) using CpG as the adjuvant and GM-CSF to recruit dendritic cells to the injection site or directly conjugating CpG to the MICA alpha 3 domain-ferritin fusion protein and GM-CSF. It was found that injections of these vaccines induced high-titer antibodies directed against the MICA alpha 3 domain. Surprisingly, the MICA alpha 3 domain-ferritin fusion protein that had CpG directly conjugated achieved higher antibody titers.

These antibodies induced by the vaccine composition of the invention bound to multiple MICA alleles and stained tumor cells that were MICA positive. Importantly, these polyclonal antibodies inhibited shedding of MICA by tumor cells. The in vivo efficacy of the vaccine was tested in a metastatic mouse model of melanoma. B16F10 melanoma cells were genetically modified to express MICA and injected intravenously after the mice had been vaccinated twice. The vaccine provided a high level of protection while control mice had large numbers of pulmonary metastases (~150-200).

The vaccine of the invention is conceptually different from conventional cancer vaccines that attempt to induce an immune response that eliminates all cancer cells expressing a particular antigen. In contrast the purpose of the vaccine of the invention is to prevent tumor escape from an important immune surveillance pathway. This vaccine will be safe based on the study of patients with MICA antibodies and the fact that MIC expression flags cells for elimination by cytotoxic lymphocytes. The benefits of the vaccine approach are: low cost of a vaccine, long-term protection against escape from immune surveillance, induction of polyclonal antibodies that inhibit shedding and rapidly clear shed MIC by formation of immune complexes and induction of a T cell response against other tumor antigens by enhanced uptake of apoptotic tumor fragments by dendritic cells.

Also provided by the invention are self-assembling ferritin-based, nanoparticles that display immunogenic portions of MICA alpha 3 domain on their surface. Optionally, the nanoparticles further include a CpG oligonucleotide. For example, CpG oligonucleotide is covalently coupled to the MICA alpha 3 domain-ferritin fusion protein. Such nanoparticles are useful for vaccinating individuals. Accordingly, the present invention also relates to fusion proteins for producing such nanoparticles and nucleic acid molecules encoding such proteins. Additionally, the present invention relates to, methods of producing nanoparticles of the present invention, and methods of using such nanoparticles to vaccinate individuals.

Also provided by the invention are vaccine compositions comprising a MIC alpha 3-domain peptide joined to a CpG oligonucleotide.

Vaccines Against MIC Alpha3 Domain Protein

The invention provides a vaccine composition suitable for administration to a human comprising, as an immunogenic component, at least one MIC alpha 3-domain peptide. The MIC alpha 3-domain peptide comprises or consists of the full-length alpha 3 domain of MICA or MICB, which domain corresponds to amino acids 181 to 274 of SEQ ID NO: 1 or SEQ ID NO: 2. Optionally, the peptide includes one or more flanking amino acids. In this context, the term "flanking amino acids" refers to the amino acids adjacent to the MIC alpha 3-domain sequence in the full-length reference sequence [SEQ ID NO: 1 for MICA or SEQ ID NOs: 2 for MICB]. In certain embodiments, the peptide comprises 2, 4, 6, 8, or 10 flanking amino acids on either its N- or C-terminal end, or both. In some embodiments the vaccine peptide is non glycosylated.

Amino Acid Sequence of MICA

```
HSLRYNLTVLSWDGSVQSGFLAEVHLDGQPFLRYDRQKCRAKPQGQWAED
VLGNKTWDRETRDLTGNGKDLRMTLAHIKDQKEGLHSLQEIRVCEIHEDN
STRSSQHFYYDGELFLSQNVETEEWTVPQSSRAQTLANINVRNFLKEDAM
KTKTHYHAMHADCLQELRRYLESSVVLRRTVPPMVNVTRSEASEGNITVT
CRASSFYPRNITLTWRQDGVSLSHDTQQWGDVLPDGNGTYQTWVATRICQ
GEEQRFTCYMEHSGNHSTHPVPSGKVLVLQSHWQTFHVSAVAAAAAAIFV
IIIFYVRCCKKKTSAAEGPELVSLQVLDQHPVGTSDHRDATQLGFQPLMS
ALGSTGSTEGA (SEQ ID NO: 1)
```

Amino Acid Sequence of MICB

```
PHSLRYNLMVLSQDGSVQSGFLAEGHLDGQPFLRYDRQKRRAKPQGQWAE
DVLGAKTWDTETEDLTENGQDLRRTLTHIKDQKGGLHSLQEIRVCEIHED
SSTRGSRHFYYDGELFLSQNLETQESTVPQSSRAQTLAMNVTNFWKEDAM
KTKTHYRAMQADCLQKLQRYLKSGVAIRRTVPPMVNVTCSEVSEGNITVT
CRASSFYPRNITLTWRQDGVSLSHNTQQWGDVLPDGGTYQTWVATRIRQG
EEQRFTCYMEHSGNHGTHPVPSGKALVLQSQRTDFPYVSAAMPCFVIIII
LCVPCCKKKTSAAEGPELVSLQVLDQHPVGTDHRDAAQLGFQPLMSATG
STGSTEGA (SEQ ID NO: 2)
```

In a preferred embodiment, the vaccine comprises a peptide having the amino acid sequence of:

(SEQ ID NO: 3)
RTVPPMVNVTRSEASEGNITVTCRASGFYPWNITLSWRQDGVSLSHDTQQ

WGDVLPDGNGTYQTWVATRISQGEEQRFTCYMEHSGNHSTHPVPSGKVLV

LQSHWQTFH
or (SEQ ID NO: 4)
RTVPPMVQVTRSEASEGQITVTCRASGFYPWNINLSWRQDGVSLSHDTQQ

WGDVLPDGNGTYQTWVATRISQGEEQRFTCYMEHSGQHSTHPVPSGKVLV

LQSHWQTFH.

In another embodiment, the vaccine composition comprises a nucleic acid encoding the MIC alpha 3-domain sequence. The nucleic acid may be in the form of an expression vector, for example a plasmid or a viral vector, or the nucleic acid may be packaged into nanoparticles. In one embodiment, the nucleic acid is delivered to a subject by injection. In one embodiment, the nucleic acid is injected as purified DNA or in the form of nanoparticles. In one embodiment, modified immune cells which have been modified to express the nucleic acid are injected. In one embodiment, the immune cells are modified via transfection or infection in vitro with a vector comprising the nucleic acid.

The peptides which form or are incorporated into the vaccine compositions of the invention are preferably purified from contaminating chemical precursors, if chemically synthesized, or substantially free of cellular material from the cell or tissue source from which they are derived. In a specific embodiment, the peptides are 60%, preferably 65%, 70%, 75%, 80%, 85%, 90%, 95%, or 99% free of contaminating chemical precursors, proteins, lipids or nucleic acids. In a preferred embodiment, the peptides are substantially free of contaminating virus. Preferably, each composition for administering to a subject is at least 95%, at least 97%, or at least 99% free of contaminating virus.

In one embodiment, the MIC alpha 3-domain peptide of a vaccine composition of the invention comprises or consists of one or more peptides that is at least 90%, at least 95%, at least 98%, or at least 99% identical to a peptide including amino acids 181 to 274 of SEQ ID NO: 1 or SEQ ID NO: 2. In this context, the term "similar" refers to amino acid sequence similarity which is defined according to the number of conservative and non-conservative amino acid changes in a query sequence relative to a reference sequence. Conservative and non-conservative amino acid changes are known in the art. See, for example, W. R. Taylor, The Classification of Amino Acid Conservation, J. Theor. Biol. 1986 119:205-218, and D. Bordo and P. Argos, Suggestions for "Safe" Residue Substitutions in Site-Directed Mutagenesis, 1991 J. Mol. Biol. 217:721-729. Generally, a conservative amino acid change refers to a substitution of one amino acid for another amino acid having substantially similar chemical properties, specifically with reference to the amino acid side chains. A non-conservative change refers to a substitution of one amino acid for another amino acid having substantially different chemical properties. Generally, conservative substitutions are those recognized in the art as being unlikely to affect the overall structure or biological function of the polypeptide, while non-conservative changes are recognized as more likely to affect structure and function.

Non-limiting examples of a conservative amino acid change include substitution of amino acids within the following groups: aliphatic, aromatic, polar, nonpolar, acidic, basic, phosphorylatable hydrophobic, hydrophilic, small nonpolar, small polar, large nonpolar, and large polar. Non-limiting examples of non-conservative amino acid changes include substitutions of amino acids between the foregoing groups.

In one embodiment, a conservative amino acid change is a substitution in which the substitution matrix for the pair of residues has a positive value. Examples of amino acid substitution matrices are known in the art, for example the BLOSUM50 matrix or the PAM250 matrix (see W. A. Pearson, Rapid and Sensitive Sequence Comparison with FASTP and FASTA, Meth. Enzymology, 1990 183:63-98, ed. R. Doolittle, Academic Press, San Diego). For further examples of scoring matrices and a comparison between them see M. S. Johnson and J. P. Overington, 1993, A Structural Basis for Sequence Comparisons: An Evaluation of Scoring Methodologies, J. Mol. Biol. 233:716-738.

In a preferred embodiment, a conservative amino acid change is a substitution of one amino acid for another amino acid within the same chemical group wherein the groups are selected from neutral and polar amino acids (Ser, Thr, Pro, Ala, Gly, Asn, Gln), negatively charged and polar amino acids (Asp, Glu), positively charged and polar amino acids (His, Arg, Lys), nonpolar amino acids lacking a ring structure (Met, Ile, Leu, Val), nonpolar amino acids having a ring structure (Phe, Tyr, Trp), and Cysteine.

In various embodiments, the peptide is conjugated to a CpG oligonucleotide sequence.

In other embodiments, the peptide is conjugated to a carrier protein. The term "carrier protein" is intended to cover both small peptides and large polypeptides (>10 kDa). The carrier protein may be any peptide or protein. It may comprise one or more T-helper epitopes. The carrier protein may be tetanus toxoid (TT), tetanus toxoid fragment C, non-toxic mutants of tetanus toxin [note all such variants of TT are considered to be the same type of carrier protein for the purposes of this invention], polypeptides comprising tetanus toxin T-cell epitopes such as N19 (WO2006/067632), diphtheria toxoid (DT), CRM197, other non-toxic mutants of diphtheria toxin such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or 4,950,740; mutation of at least one or more residues Lys 516, Lys 526, Phe 530 and/or Lys 534 and other mutations disclosed in U.S. Pat. No. 5,917,017 or 6,455,673; or fragment disclosed in U.S. Pat. No. 5,843,711] (note all such variants of DT are considered to be the same type of carrier protein for the purposes of this invention), pneumococcal pneumolysin (Kuo et al (1995) Infect Immun 63; 2706-13), OMPC (meningococcal outer membrane protein—usually extracted from N. meningitidis serogroup B—EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761), *H. influenzae* Protein D (EP594610 and WO 00/56360), pneumococcal PhtA (WO 98/18930, also referred to Sp36), pneumococcal PhtD (disclosed in WO 00/37105, and is also referred to Sp036D), pneumococcal PhtB (disclosed in WO 00/37105, and is also referred to Sp036B), or PhtE (disclosed in WO00/30299 and is referred to as BVH-3).

In one embodiment, the carrier protein can be selected from the group consisting of: tetanus toxoid (TT), fragment C of tetanus toxoid, diphtheria toxoid (DT), CRM197, Pneumolysin (Ply), protein D, PhtD, PhtDE and N19. In one embodiment the carrier protein is CRM197.

Vaccines Comprising HA-Ferritin Fusion Proteins

The inventors have also discovered that fusion of a MIC alpha 3-domain peptide with ferritin protein a MIC alpha 3-ferritin fusion protein) results in a vaccine that elicits a robust immune response to cancer. Such MIC alpha 3-ferritin fusion proteins self-assemble into nanoparticles that display immunogenic portions of the MIC alpha 3-domain peptide on their surface. These nanoparticles are useful for vaccinating individuals against MIC alpha 3-domain. Thus, one embodiment of the present invention is an MIC alpha 3-ferritin fusion protein comprising a monomeric ferritin subunit disclosed herein joined to a MIC alpha 3-domain peptide disclosed herein. The MIC alpha 3-ferritin fusion protein is capable of self-assembling into nanoparticles. In various aspects the fusion protein further comprises a CpG oligonucleotide sequence. The CpG oligonucleotide sequence can be covalently attached to the MIC alpha 3-ferritin fusion protein.

Ferritin is a globular protein found in all animals, bacteria, and plants, that acts primarily to control the rate and location of polynuclear $Fe(III)_2O_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled ‘A, B, C, and D & E’ from the N-terminus respectively. The N-terminal sequence lies adjacent to the capsid three-fold axis and extends to the surface, while the E helices pack together at the four-fold axis with the C-terminus extending into the particle core. The consequence of this packing creates two pores on the capsid surface. It is expected that one or both of these pores represent the point by which the hydrated iron diffuses into and out of the capsid. Following production, these monomeric ferritin subunit proteins self-assemble into the globular ferritin protein. Thus, the globular form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the globular form of the protein. Amino acid sequences from monomeric ferritin subunits of any known ferritin protein can be used to produce fusion proteins of the present invention, so long as the monomeric ferritin subunit is capable of self-assembling into a nanoparticle displaying MIC alpha 3-domain on its surface. In one embodiment, the monomeric subunit is from a ferritin protein selected from the group consisting of a bacterial ferritin protein, a plant ferritin protein, an algal ferritin protein, an insect ferritin protein, a fungal ferritin protein and a mammalian ferritin protein. In one embodiment, the ferritin protein is from *Helicobacter pylori.*

MIC alpha 3-ferritin fusion proteins of the present invention need not comprise the full-length sequence of a monomeric subunit polypeptide of a ferritin protein. Portions, or regions, of the monomeric ferritin subunit protein can be utilized so long as the portion comprises an amino acid sequence that directs self-assembly of monomeric ferritin subunits into the globular form of the protein. One example of such a region is located between amino acids 5 and 167 of the *Helicobacter pylori* ferritin protein. More specific regions are described in Zhang, Y. Self-Assembly in the Ferritin Nano-Cage Protein Super Family. 2011, Int. J. Mol. Sci., 12, 5406-5421, which is incorporated herein by reference in its entirety.

One embodiment of the present invention is an MIC alpha 3-ferritin fusion protein comprising an MIC alpha 3-domain protein of the present invention joined to at least 25 contiguous amino acids, at least 50 contiguous amino acids, at least 75 contiguous amino acids, at least 100 contiguous amino acids, or at least 150 contiguous amino acids from a monomeric ferritin subunit, wherein the MIC alpha 3-ferritin fusion protein is capable of self-assembling into nanoparticles. One embodiment of the present invention is an MIC alpha 3-ferritin fusion protein comprising an MIC alpha 3-domain protein of the present invention joined to at least 25 contiguous amino acids, at least 50 contiguous amino acids, at least 75 contiguous amino acids, at least 100 contiguous amino acids, or at least 150 contiguous amino acids from the region of a ferritin protein corresponding to the amino acid sequences of the *Helicobacter pylori* ferritin monomeric subunit that direct self-assembly of the monomeric subunits into the globular form of the ferritin protein, wherein the MIC alpha 3-ferritin fusion protein is capable of self-assembling into nanoparticles.

It is well-known in the art that some variations can be made in the amino acid sequence of a protein without affecting the activity of the protein. Such variations include insertion of amino acid residues, deletions of amino acid residues, and substitutions of amino acid residues. Thus, in one embodiment, the sequence of the monomeric ferritin subunit is divergent enough from the sequence of a ferritin subunit naturally found in a mammal, such that when the variant monomeric ferritin subunit is introduced into the mammal, it does not result in the production of antibodies that react with the mammal’s natural ferritin protein. According to the present invention, such a monomeric subunit is referred to as immunogenically neutral. One embodiment of the present invention is an MIC alpha 3-ferritin fusion protein comprising an MIC alpha 3-domain protein of the present invention joined to an amino acid sequence at least 80%, at least 85%, at least 90%, at least 95%, and at least 97% identical to the amino acid sequence of a monomeric ferritin subunit that is responsible for directing self-assembly of the monomeric ferritin subunits into the globular form of the protein, wherein the MIC alpha 3-ferritin fusion protein is capable of self-assembling into nanoparticles. In one embodiment, the HA-ferritin fusion protein comprises a polypeptide sequence identical in sequence to a monomeric ferritin subunit. One embodiment of the present invention is an MIC alpha 3-ferritin fusion protein comprising an MIC alpha 3-domain protein of the present invention joined to an amino acid sequence at least 80%, at least 85%, at least 90%, at least 95%, and at least 97% identical to the amino acid sequence of a monomeric ferritin subunit from *Helicobacter pylori*, wherein the MIC alpha 3-ferritin fusion protein is capable of self-assembling into nanoparticles.

In some embodiments, it may be useful to engineer mutations into the amino acid sequences of proteins of the present invention. For example, it may be useful to alter sites such as enzyme recognition sites or glycosylation sites in the monomeric ferritin subunit, the trimerization domain, or linker sequences, in order to give the fusion protein beneficial properties (e.g., solubility, half-life, mask portions of the protein from immune surveillance). In this regard, it is known that the monomeric subunit of ferritin is not glycosylated naturally. However, it can be glycosylated if it is expressed as a secreted protein in mammalian or yeast cells. Thus, in one embodiment, potential N-linked glycosylation sites in the amino acid sequences from the monomeric ferritin subunit are mutated so that the mutated ferritin subunit sequences are no longer glycosylated at the mutated site.

Proteins of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can effect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, a viral vector, or other vector. In one embodiment, a vector can be a cytomegalovirus (CMV), retrovirus, adenovirus, adeno-associated virus, herpes virus, vaccinia virus, poliovirus, sindbis virus, or any other DNA or RNA virus vector. In one embodiment, a vector can be a pseudotyped lentiviral or retroviral vector. In one embodiment, a vector can be a DNA plasmid. In one embodiment, a vector can be a DNA plasmid comprising viral components and plasmid components to enable nucleic acid molecule delivery and expression. Methods for the construction of nucleic acid constructs of the present disclosure are well known. See, for example, Molecular Cloning: a Laboratory Manual, 3.sup.rd edition, Sambrook et al. 2001 Cold Spring Harbor Laboratory Press, and Current Protocols in Molecular Biology, Ausubel et al. eds., John Wiley & Sons, 1994. In one embodiment, the vector is a DNA plasmid, such as a CMV/R plasmid such as CMV/R or CMV/R 8 KB (also referred to herein as CMV/R 8 kb). Examples of CMV/R and CMV/R 8 kb are provided herein. CMV/R is also described in U.S. Pat. No. 7,094,598 B2, issued Aug. 22, 2006.

As used herein, a nucleic acid molecule comprises a nucleic acid sequence that encodes MIC alpha 3-domain peptide immunogen, a ferritin monomeric subunit, and/or an MIC alpha 3-ferritin fusion protein of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate codons encoding different amino acids, such as to introduce codons that encode an N-linked glycosylation site. Methods to produce nucleic acid molecules of the disclosure are known in the art, particularly once the nucleic acid sequence is known. It is to be appreciated that a nucleic acid construct can comprise one nucleic acid molecule or more than one nucleic acid molecule. It is also to be appreciated that a nucleic acid molecule can encode one protein or more than one protein.

In one embodiment, the monomeric subunit of ferritin is from the ferritin protein of *Helicobacter pylori*.

Also embodied in the present invention are nucleic acid sequences that are variants of nucleic acid sequence encoding protein of the present invention. Such variants include nucleotide insertions, deletions, and substitutions, so long as they do not affect the ability of fusion proteins of the present invention to self-assemble into nanoparticles, or significantly affect the ability of the MIC alpha 3-domain portion of fusion proteins to elicit an immune response to MIC alpha 3-domain protein.

Also encompassed by the present invention are expression systems for producing fusion proteins of the present invention. In one embodiment, nucleic acid molecules of the present invention are operationally linked to a promoter. As used herein, operationally linked means that proteins encoded by the linked nucleic acid molecules can be expressed when the linked promoter is activated. Promoters useful for practicing the present invention are known to those skilled in the art. One embodiment of the present invention is a recombinant cell comprising a nucleic acid molecule of the present invention. One embodiment of the present invention is a recombinant virus comprising a nucleic acid molecule of the present invention.

As indicated above, the recombinant production of the ferritin fusion proteins of the present invention can take place using any suitable conventional recombinant technology currently known in the field. For example, molecular cloning a fusion protein, such as ferritin with a suitable protein such as the recombinant MIC alpha 3-domain protein, can be carried out via expression in *E. coli* with the suitable monomeric subunit protein, such as the *Helicobacter pylori* ferritin monomeric subunit. The construct may then be transformed into protein expression cells, grown to suitable size, and induced to produce the fusion protein.

As has been described, because MIC alpha 3-ferritin fusion proteins of the present invention comprise a monomeric subunit of ferritin, they can self-assemble. According to the present invention, the supramolecule resulting from such self-assembly is referred to as a MIC alpha 3 expressing ferritin based nanoparticle. For ease of discussion, the MIC alpha 3 expressing ferritin based nanoparticle will simply be referred to as a, or the, nanoparticle (np). Nanoparticles of the present invention have the same structural characteristics as the ferritin proteins described earlier. That is, they contain 24 subunits and have 432 symmetry. In the case of nanoparticles of the present invention, the subunits are the fusion proteins comprising a ferritin monomeric subunit joined to an MIC alpha 3-domain protein. Such nanoparticles display at least a portion of the MIC alpha 3-domain protein on their surface. Thus, one embodiment of the present invention is a nanoparticle comprising an MIC alpha 3-ferritin fusion protein, wherein the fusion protein comprises a monomeric ferritin subunit joined to a MIC alpha 3-domain protein. In one embodiment, the nanoparticle is an octahedron.

Because MIC alpha 3-ferritin fusion proteins and nanoparticles of the present invention can elicit an immune response to an MIC alpha 3-domain protein, they can be used as vaccines to treat cancer. According to the present invention a vaccine can be a MIC alpha 3-domain peptide immunogen, an MIC alpha 3-ferritin fusion protein, or a nanoparticle of the present invention. Vaccines of the present invention can also contain other components such as adjuvants, buffers and the like. Although any adjuvant can be used, preferred embodiments can contain: chemical adjuvants such as aluminum phosphate, benzylkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C—C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C—C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

Mesoporous Silica

The vaccine composition according to the invention can further comprise an immunization scaffold. In one embodiment, the immunization scaffold is mesoporous silica nanoparticles (MSR). MSR can be in any shape or form, such as rods, spheres, wires, cubes, or polyhedrons. The shape or form of MSR is typically the result of specific reaction conditions. For example, mesoporous silica nanoparticles can be synthesized by any method known in the art, such as reacting tetraethyl orthosilicate with a template made of micellar rods. The result is a collection of nano-sized spheres or rods that are filled with a regular arrangement of pores. The template can then be removed by washing with a solvent adjusted to the proper pH. In another technique, the mesoporous particle could be synthesized using a simple sol-gel method or a spray drying method. Tetraethyl orthosilicate is also used with an additional polymer monomer (as a template). Other methods include those described in U.S. Patent Publication 20150072009, 20120264599 and 20120256336, hereby incorporated by reference.

Granulocyte Macrophage Colony Stimulating Factor (GM-CSF)

Granulocyte-macrophage colony-stimulating factor (GM-CSF) is a protein secreted by macrophages, T cells, mast cells, endothelial cells and fibroblasts. Specifically, GM-CSF is a cytokine that functions as a white blood cell growth factor. GM-CSF stimulates stem cells to produce granulocytes and monocytes. Monocytes exit the blood stream, migrate into tissue, and subsequently mature into macrophages.

Scaffold devices described herein comprise and release GM-CSF polypeptides to attract host DCs to the device. Contemplated GM-CSF polypeptides are isolated from endogenous sources or synthesized in vivo or in vitro. Endogenous GM-CSF polypeptides are isolated from healthy human tissue. Synthetic GM-CSF polypeptides are synthesized in vivo following transfection or transformation of template DNA into a host organism or cell, e.g. a mammal or cultured human cell line. Alternatively, synthetic GM-CSF polypeptides are synthesized in vitro by polymerase chain reaction (PCR) or other art-recognized methods (e.g., Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

GM-CSF polypeptides are modified to increase protein stability in vivo. Alternatively, GM-CSF polypeptides are engineered to be more or less immunogenic. Endogenous mature human GM-CSF polypeptides are glycosylated, reportedly, at amino acid residues 23 (leucine), 27 (asparagine), and 39 (glutamic acid) (see U.S. Pat. No. 5,073,627). GM-CSF polypeptides of the present invention are modified at one or more of these amino acid residues with respect to glycosylation state.

GM-CSF polypeptides are recombinant. Alternatively, GM-CSF polypeptides are humanized derivatives of mammalian GM-CSF polypeptides. Exemplary mammalian species from which GM-CSF polypeptides are derived include, but are not limited to, mouse, rat, hamster, guinea pig, ferret, cat, dog, monkey, or primate. In a preferred embodiment, GM-CSF is a recombinant human protein (PeproTech, Catalog #300-03). Alternatively, GM-CSF is a recombinant murine (mouse) protein (PeproTech, Catalog #315-03). Finally, GM-CSF is a humanized derivative of a recombinant mouse protein.

Human Recombinant GM-CSF (PeproTech, Catalog #300-03) is encoded by the following polypeptide sequence:

```
                                       (SEQ ID NO: 26)
MAPARSPSPS TQPWEHVNAI QEARRLLNLS RDTAAEMNET

VEVISEMFDL QEPTCLQTRL ELYKQGLRGS LTKLKGPLTM

MASHYKQHCP PTPETSCATQ IITFESFKEN LKDFLLVIPF

DCWEPVQE
```

Murine Recombinant GM-CSF (PeproTech, Catalog #315-03) is encoded by the following polypeptide sequence:

```
                                       (SEQ ID NO: 27)
MAPTRSPITV TRPWKHVEAI KEALNLLDDM PVTLNEEVEV
VSNEFSFKKL TCVQTRLKIF EQGLRGNFTK LKGALNMTAS
YYQTYCPPTP ETDCETQVTT YADFIDSLKT FLTDIPFECK KPVQK
```

Human Endogenous GM-CSF is encoded by the following mRNA sequence (NCBI Accession No. NM 000758 and SEQ ID NO: 28):

```
                                        (SEQ ID NO: 28)
acacagagag aaaggctaaa gttctctgga ggatgtggct gcagagcctg ctgctcttgg    61
gcactgtggc ctgcagcatc tctgcacccg cccgctcgcc cagcccagc acgcagccct   121 gggagcatgt gaatgccatc caggaggccc ggcgtctcct gaacctgagt agagacactg   181
ctgctgagat gaatgaaaca gtagaagtca tctcagaaat gtttgacctc caggagccga   241
```

```
                                  -continued
cctgcctaca gacccgcctg gagctgtaca agcagggcct gcggggcagc ctcaccaagc    301
tcaagggccc cttgaccatg atggccagcc actacaagca gcactgccct ccaaacccgg    361
aaacttcctg tgcaacccag attatcacct ttgaaagttt caaagagaac ctgaaggact    421
ttctgcttgt catcccttt gactgctggg agccagtcca ggagtgagac cggccagatg      481
aggctggcca agccggggag ctgctctctc atgaaacaag agctagaaac tcaggatggt    541
catcttggag ggaccaaggg gtgggccaca gccatggtgg gagtggcctg gacctgccct    601
gggccacact gaccctgata caggcatggc agaagaatgg gaatatttta tactgacaga    661
aatcagtaat atttatatat ttatattttt aaaatattta tttatttatt tatttaagtt    721
catattccat atttattcaa gatgttttac cgtaataatt attattaaaa atatgcttct    781 a
```

Human Endogenous GM-CSF is encoded by the following amino acid sequence (NCBI Accession No. NP000749.2 and SEQ ID NO: 29):

(SEQ ID NO: 29)
MWLQSLLLLGTVACSISAPARSPSPSTQPWEHVNAIQEARRLLNLSRDT

AAEMNETVEVISEMFDLQEPTCLQTRLELYKQGLRGSLTKLKGPLTMM

ASHYKQHCPPTPETSCATQIITFESFKENLKDFLLVIPFDCWEPVQE

Cytosine-Guanosine (CpG) Oligonucleotide (CpG-ODN) Sequences

CpG sites are regions of deoxyribonucleic acid (DNA) where a cysteine nucleotide occurs next to a guanine nucleotide in the linear sequence of bases along its length (the "p" represents the phosphate linkage between them and distinguishes them from a cytosine-guanine complementary base pairing). CpG sites play a pivotal role in DNA methylation, which is one of several endogenous mechanisms cells use to silence gene expression. Methylation of CpG sites within promoter elements can lead to gene silencing. In the case of cancer, it is known that tumor suppressor genes are often silenced while oncogenes, or cancer-inducing genes, are expressed. CpG sites in the promoter regions of tumor suppressor genes (which prevent cancer formation) have been shown to be methylated while CpG sites in the promoter regions of oncogenes are hypomethylated or unmethylated in certain cancers. The TLR-9 receptor binds unmethylated CpG sites in DNA.

The vaccine composition described herein comprises CpG oligonucleotides. CpG oligonucleotides are isolated from endogenous sources or synthesized in vivo or in vitro. Exemplary sources of endogenous CpG oligonucleotides include, but are not limited to, microorganisms, bacteria, fungi, protozoa, viruses, molds, or parasites. Alternatively, endogenous CpG oligonucleotides are isolated from mammalian benign or malignant neoplastic tumors. Synthetic CpG oligonucleotides are synthesized in vivo following transfection or transformation of template DNA into a host organism. Alternatively, Synthetic CpG oligonucleotides are synthesized in vitro by polymerase chain reaction (PCR) or other art-recognized methods (Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

CpG oligonucleotides are presented for cellular uptake by dendritic cells. For example, naked CpG oligonucleotides are used. The term "naked" is used to describe an isolated endogenous or synthetic polynucleotide (or oligonucleotide) that is free of additional substituents. In another embodiment, CpG oligonucleotides are bound to one or more compounds to increase the efficiency of cellular uptake. Alternatively, or in addition, CpG oligonucleotides are bound to one or more compounds to increase the stability of the oligonucleotide within the scaffold and/or dendritic cell. CpG oligonucleotides are optionally condensed prior to cellular uptake. For example, CpG oligonucleotides are condensed using polyethylimine (PEI), a cationic polymer that increases the efficiency of cellular uptake into dendritic cells.

CpG oligonucleotides can be divided into multiple classes. For example, exemplary CpG-ODNs encompassed by compositions, methods and devices of the present invention are stimulatory, neutral, or suppressive. The term "stimulatory" describes a class of CpG-ODN sequences that activate TLR9. The term "neutral" describes a class of CpG-ODN sequences that do not activate TLR9. The term "suppressive" describes a class of CpG-ODN sequences that inhibit TLR9. The term "activate TLR9" describes a process by which TLR9 initiates intracellular signaling.

Stimulatory CpG-ODNs can further be divided into three types A, B and C, which differ in their immune-stimulatory activities. Type A stimulatory CpG ODNs are characterized by a phosphodiester central CpG-containing palindromic motif and a phosphorothioate 3' poly-G string. Following activation of TLR9, these CpG ODNs induce high IFN-.alpha. production from plasmacytoid dendritic cells (pDC). Type A CpG ODNs weakly stimulate TLR9-dependent NF-.kappa.B signaling.

Type B stimulatory CpG ODNs contain a full phosphorothioate backbone with one or more CpG dinucleotides. Following TLR9 activation, these CpG-ODNs strongly activate B cells. In contrast to Type A CpG-ODNs, Type B CpG-ODNS weakly stimulate IFN-.alpha. secretion.

Type C stimulatory CpG ODNs comprise features of Types A and B. Type C CpG-ODNs contain a complete phosphorothioate backbone and a CpG containing palindromic motif. Similar to Type A CpG ODNs, Type C CpG ODNs induce strong IFN-.alpha. production from pDC. Similar to Type B CpG ODNs, Type C CpG ODNs induce strong B cell stimulation.

Exemplary stimulatory CpG ODNs comprise, but are not limited to, ODN 1585, ODN 1668, ODN 1826, ODN 2006, ODN 2006-G5, ODN 2216, ODN 2336, ODN 2395, ODN M362 (all InvivoGen). The present invention also encompasses any humanized version of the preceding CpG ODNs. In one preferred embodiment, compositions, methods, and devices of the present invention comprise ODN 1826 (the sequence of which from 5' to 3' is tccatgacgttcctgacgtt, wherein CpG elements are bolded, SEQ ID NO: 30).

Neutral, or control, CpG ODNs that do not stimulate TLR9 are encompassed by the present invention. These ODNs comprise the same sequence as their stimulatory counterparts but contain GpC dinucleotides in place of CpG dinucleotides.

Exemplary neutral, or control, CpG ODNs encompassed by the present invention comprise, but are not limited to, ODN 1585 control, ODN 1668 control, ODN 1826 control, ODN 2006 control, ODN 2216 control, ODN 2336 control, ODN 2395 control, ODN M362 control (all InvivoGen). The present invention also encompasses any humanized version of the preceding CpG ODNs.

Methods of Treating and Administration

The vaccine compositions of the present invention are useful for the prophylaxis and treatment of cancer. Accordingly, the present invention provides methods of prophylaxis against cancer in a subject at risk of developing cancer and methods of treating cancer in a subject in need of such treatment. In one embodiment, the cancer is selected from the group consisting of prostate cancer, multiple myeloma, gliobastoma multiforme, and melanoma. In one embodiment, the cancer is melanoma.

In one embodiment, a vaccine composition of the invention is administered to a subject having a cancer associated with overexpression of MICA. The overexpression of MICA can be determined using any known method in the art for measuring the expression level of a protein or the corresponding nucleic acid. Such methods include, but are not limited to, western blots, northern blots, southern blots, ELISA, immunoprecipitation, immunofluorescence, flow cytometry, immunocytochemistry, nucleic acid hybridization techniques, nucleic acid reverse transcription methods, and nucleic acid amplification methods. In one embodiment, the cancer is selected from the group consisting of melanoma, lung, breast, kidney, ovarian, prostate, pancreatic, gastric, and colon carcinoma, lymphoma or leukemia. In one embodiment, the cancer is melanoma. In one embodiment, the cancer is a plasma cell malignancy, for example, multiple myeloma (MM) or pre-malignant condition of plasma cells. In some embodiments the subject has been diagnosed as having a cancer or as being predisposed to cancer.

The vaccine compositions of the invention may be administered separately or as part of a therapeutic regimen or combination therapy, as described below. The vaccine compositions of the invention may also be administered singly, or in multiple administrations, for example in a prime-boost strategy. In this context, the term "prime-boost" refers to the use of two different immunogens in succession. The two different immunogens are typically administered successively following a period of time such as 10 to 30 days or 10 to 60 days. In one embodiment, the period of time is from 2 to 4 weeks. Thus, for example, in one embodiment a vaccine composition of the invention is administered at time zero and a second vaccine composition of the invention (comprising a different immunogen) is administered following a period of time, for example from 10 to 30 days, from 10 to 60 days, or from 2 to 4 weeks.

The first and second vaccine compositions can be, but need not be, the same composition. Thus, in one embodiment of the present invention, the step of administering the vaccine comprises administering a first vaccine composition, and then at a later time, administering a second vaccine composition.

In one embodiment, one or a plurality of different vaccine compositions of the invention is administered to the subject at multiple sites as described in U.S. Pat. No. 8,110,196. Preferably, each site drains to a lymph node or group of lymph nodes. In one embodiment, a vaccine composition of the invention is administered to multiple sites draining to two or more lymph nodes selected from the group consisting of the lymph nodes of the head and neck, the axillary lymph nodes, the tracheobronchial lymph nodes, the parietal lymph nodes, the gastric lymph nodes, the ileocolic lymph nodes, and the inguinal and subinguinal lymph nodes. In another embodiment, the sites are selected from the group consisting of the right arm, the left arm, the right thigh, the left thigh, the right shoulder, the left shoulder, the right breast, the left breast, the abdomen, the right buttock, and the left buttock. In one embodiment, the site is or drains to a nonencapsulated cluster of lymphoid tissue selected from the group consisting of the tonsils, the adenoids, the appendix, and Peyer's patches. In one embodiment, a vaccine composition of the invention is administered to a site that drains to the spleen.

In one embodiment, each vaccine composition is administered by a route independently selected from the group consisting of intradermally, subcutaneously, transdermally, intramuscularly, orally, rectally, vaginally, by inhalation, and a combination thereof. In one embodiment, at least one composition is injected directly into an anatomically distinct lymph node, lymph node cluster, or nonencapsulated cluster of lymphoid tissue.

Any suitable route of administration is encompassed by the methods of the invention, e.g. intradermal, subcutaneous, intravenous, intramuscular, or mucosal. Mucosal routes of administration include, but are not limited to, oral, rectal, vaginal, and nasal administration. In a preferred embodiment, at least one composition is administered transdermally, intradermally, subcutaneously, orally, rectally, vaginally or by inhalation. Any route approved by the Food and Drug Administration (FDA) can be used for the vaccine compositions of the invention. Exemplary methods of administration are described in the FDA's CDER Data Standards Manual, version number 004 (which is available at fda.give/cder/dsm/DRG/drg00301.htm).

Preferably, the route of administration is selected to target a composition to a particular site, for example, by injection directly into a lymph node or a lymph node cluster, by oral administration to target the lymph nodes of the stomach, by anal administration to target the lymph nodes of the rectum, by inhalation or aerosol to target the lymph nodes of the lungs, or by any other suitable route of administration.

Where the methods of the invention comprise administering a vaccine composition to multiple sites, each composition is preferably administered at substantially the same time, for example, within one to eight hours or during the same doctor's visit. In one embodiment, each composition is administered within one to two hours, within one to three hours, within one to four hours, or within one to five hours.

Where the vaccine composition is in the form of a scaffold, the method of vaccinating a subject comprises implanting the scaffold composition in the subject, preferably subcutaneous implantation. In certain embodiments, the method of vaccinating a subject may comprise implanting or injecting the scaffold vaccine composition in two or more areas of the subject's anatomy.

In one embodiment, the methods of the invention further comprise administering to the subject antigen presenting cells which have been sensitized with at least one MIC peptide. In a preferred embodiment, the antigen presenting cells are dendritic cells.

In one embodiment, the method further comprises administering to the subject one or more adjuvants. In one embodiment, the one or more adjuvants is selected from the group consisting of an oil-based adjuvant, a CpG DNA adjuvant, polyinosinic:polycytidylic acid (usually abbreviated poly(I: C)), a mineral salt adjuvant, a mineral salt gel adjuvant, a particulate adjuvant, a microparticulate adjuvant, a mucosal adjuvant, and a cytokine. Such adjuvants may either be formulated with the compositions of the invention or administered separately from the compositions, e.g., prior to, concurrently with, or after the compositions are administered to the subject. The one or more adjuvants can be covalently linked to the peptide or fusion protein of the invention. For example, a CpG DNA adjuvant is covalently linked to the peptide or fusion protein of the invention.

The methods disclosed herein can be applied to a wide range of species, e.g., humans, non-human primates (e.g., monkeys), horses, cattle, pigs, sheep, deer, elk, goats, dogs, cats, mustelids, rabbits, guinea pigs, hamsters, rats, and mice.

The terms "treat" or "treating," as used herein, refers to partially or completely alleviating, inhibiting, ameliorating, and/or relieving the disease or condition from which the subject is suffering. In some instances, treatment can result in the continued absence of the disease or condition from which the subject is suffering.

In general, methods include selecting a subject at risk for or with a condition or disease. In some instances, the subject's condition or disease can be treated with a pharmaceutical composition disclosed herein. For example, in some instances, methods include selecting a subject with cancer, e.g., wherein the subject's cancer can be treated by targeting one or both of MICA.

In some instances, treatment methods can include a single administration, multiple administrations, and repeating administration as required for the prophylaxis or treatment of the disease or condition from which the subject is suffering. In some instances, treatment methods can include assessing a level of disease in the subject prior to treatment, during treatment, and/or after treatment. In some instances, treatment can continue until a decrease in the level of disease in the subject is detected.

The terms "administer," "administering," or "administration," as used herein refers to implanting, absorbing, ingesting, injecting, or inhaling, the inventive peptide, regardless of form. In some instances, one or more of the peptides disclosed herein can be administered to a subject topically (e.g., nasally) and/or orally. For example, the methods herein include administration of an effective amount of compound or compound composition to achieve the desired or stated effect. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Following administration, the subject can be evaluated to detect, assess, or determine their level of disease. In some instances, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some instances, the disclosure provides methods for detecting immune cells e.g., B cells and/or memory B cells, from a human subject. Such methods can be used, for example, to monitor the levels of immune cells e.g., B cells and/or memory B cells, in a human subject, e.g., following an event. Exemplary events can include, but are not limited to, detection of diseases, infection; administration of a therapeutic composition disclosed herein, administration of a therapeutic agent or treatment regimen, administration of a vaccine, induction of an immune response. Such methods can be used clinically and/or for research.

Effective Amounts and Dosages

In one embodiment, an effective amount of a vaccine composition of the invention is the amount sufficient to reduce the severity of a cancer in a subject having cancer, or the amount sufficient to reduce or ameliorate the severity of one or more symptoms thereof, the amount sufficient to prevent the progression of the cancer, the amount sufficient to prevent further metastasis of the cancer, the amount sufficient to cause clinical regression of the cancer, or the amount sufficient to enhance or improve the therapeutic effect(s) of another therapy or therapeutic agent administered concurrently with, before, or after a vaccine composition of the invention.

Symptoms of cancer are well-known to those of skill in the art and include, without limitation, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

In one embodiment, the effective amount of a vaccine composition of the invention is the amount sufficient to produce an antibody secreting B cell or cytotoxic T cell mediated immune response directed against one or more of the peptides of the vaccine compositions of the invention. In one embodiment, the effective amount of a vaccine composition of the invention is the amount sufficient to produce an antibody secreting B cell or cytotoxic T cell mediated immune response directed against a cancer cell. The ability of the vaccine compositions of the invention to elicit an immune response can be determined using any routine method available to those of skill in the art. In one embodiment, the effective amount of each composition is the amount sufficient to produce a cytotoxic T cell response in the subject as measured, for example, by a mixed lymphocyte T cell assay.

In one embodiment, the effective amount of the vaccine composition administered to the subject, or at a particular site of the subject, is that amount which delivers 1 to 1000 micrograms of the one or more peptides of the composition. In one embodiment, the amount of peptides is 1 to 100 micrograms, 1 to 200 micrograms, 1 to 300 micrograms, 1 to 400 micrograms, 1 to 500 micrograms, 1 to 600 micrograms, 1 to 700 micrograms, 1 to 800 micrograms, or 1 to 900 micrograms. In another embodiment, the amount of peptides is 1 to 10 micrograms, 1 to 20 micrograms, 1 to 30 micrograms, 1 to 40 micrograms, 1 to 50 micrograms, 1 to 60 micrograms, 1 to 70 micrograms, 1 to 80 micrograms, or 1 to 90 micrograms. In one embodiment, the total amount of peptides administered to a subject does not exceed 5 milligrams. In one embodiment, the total amount of peptides administered to a subject does not exceed 2 milligrams.

Combination Therapy

The present invention also provides methods for the treatment or prophylaxis of cancer which comprise administering a vaccine composition of the invention to a subject in need thereof, along with one or more additional therapeutic agents or therapeutic regimens. In one embodiment, a vaccine composition of the invention is administered as part of a therapeutic regimen that includes surgery, a chemotherapeutic agent, or radiation therapy, an immunotherapy, or any combination of the foregoing.

In one embodiment, the therapeutic regimen comprises or further comprises one or more immunostimulatory agents. In one embodiment, the one or more immunostimulatory agents is selected from the group consisting of an anti-CTLA-4 antibody or peptide, an anti-PD-1 antibody or peptide, an anti-PDL-1 antibody or peptide, an anti-OX40 (also known as CD134, TNFRSF4, ACT35 and/or TXGP1L) antibody or peptide, an anti-GITR (also known as TNFRSF18, AITR, and/or CD357) antibody or peptide, an anti-LAG-3 antibody or peptide, and/or an anti-TIM-3 antibody or peptide.

In one embodiment, the one or more immunostimulatory agents is selected from an anti-MICA antibody described in WO 2013/049517 or WO 2008/036981. In one embodiment, the one or more immunostimulatory agents is selected from CM33322 Ab4, CM33322 Ab28, and CM33322 Ab29, which are described in U.S. Provisional Application Nos. 61/792,034 and 61/913,198 and in U.S. application Ser. No. 14/025,573.

In one embodiment, the therapeutic regimen comprises or further comprises one or more cytokines. In one embodiment, the vaccine compositions of the invention comprise one or more cytokines. In one embodiment, at least one cytokine is an interleukin or an interferon. In one embodiment, at least one cytokine is an interleukin selected from the group consisting of IL-1.alpha., IL-1.beta., IL-2, IL-3, IL-4, IL-5, IL-6, IL-7, IL-8, IL-9, IL-11, IL-12, IL-13, IL-15, and IL-18. In another embodiment, at least one cytokine is an interferon selected from IFN.alpha., IFN.beta., and IFN.gamma.

In one embodiment, a vaccine composition of the invention is administered as part of a therapeutic regimen that includes administering to the subject at least one chemotherapeutic agent selected from the group consisting of histone deacetylase inhibitors ("HDAC") inhibitors, proteasome inhibitors, alkylating agents, and topoisomerase inhibitors.

In one embodiment, the chemotherapeutic agent is an HDAC inhibitor selected from the group consisting of hydroxamic acid, Vorinostat (Zolinza), suberoylanilide hydroxamic acid (SAHA)(Merck), Trichostatin A (TSA), LAQ824 (Novartis), Panobinostat (LBH589) (Novartis), Belinostat (PXD101)(CuraGen), ITF2357 Italfarmaco SpA (Cinisello), Cyclic tetrapeptide, Depsipeptide (romidepsin, FK228) (Gloucester Pharmaceuticals), Benzamide, Entinostat (SNDX-275/MS-275)(Syndax Pharmaceuticals), MGCD0103 (Celgene), Short-chain aliphatic acids, Valproic acid, Phenyl butyrate, AN-9, pivanex (Titan Pharmaceutical), CHR-3996 (Chroma Therapeutics), and CHR-2845 (Chroma Therapeutics).

In one embodiment, the chemotherapeutic agent is a proteasome inhibitor selected from the group consisting of Bortezomib, (Millennium Pharmaceuticals), NPI-0052 (Nereus Pharmaceuticals), Carfilzomib (PR-171) (Onyx Pharmaceuticals), CEP 18770, and MLN9708.

In one embodiment, the chemotherapeutic agent is an alkylating agent such as mephalan.

In one embodiment, the chemotherapeutic agent is a topoisomerase inhibitor such as Adriamycin (doxorubicin).

In one embodiment, the therapeutic regimen comprises or further comprises one or more of chemotherapy, radiation therapy, cytokines, chemokines and other biologic signaling molecules, tumor specific vaccines, cellular cancer vaccines (e.g., GM-CSF transduced cancer cells), tumor specific monoclonal antibodies, autologous and allogeneic stem cell rescue (e.g., to augment graft versus tumor effects), other therapeutic antibodies, molecular targeted therapies, anti-angiogenic therapy, infectious agents with therapeutic intent (such as tumor localizing bacteria) and gene therapy.

Kits

The invention provides a pharmaceutical pack or kit for carrying out the methods or therapeutic regimens of the invention. In one embodiment, the kit comprises a vaccine composition of the invention in lyophilized form. In one embodiment, the kit comprises a vaccine composition of the invention in the form of a protein scaffold.

In another embodiment, the kit further comprises in one or more additional containers a cytokine or an adjuvant.

The composition in each container may be in the form of a pharmaceutically acceptable solution, e.g., in combination with sterile saline, dextrose solution, or buffered solution, or other pharmaceutically acceptable sterile fluid. Alternatively, the composition may be lyophilized or desiccated; in this instance, the kit optionally further comprises in a separate container a pharmaceutically acceptable solution (e.g., saline, dextrose solution, etc.), preferably sterile, to reconstitute the composition to form a solution for injection purposes.

In another embodiment, the kit further comprises one or more reusable or disposable device(s) for administration (e.g., syringes, needles, dispensing pens), preferably packaged in sterile form, and/or a packaged alcohol pad. Instructions are optionally included for administration of the compositions by a clinician or by the patient. The kit may also comprise other materials, e.g., metal or plastic foil, such as a blister pack.

In some embodiments, the present disclosure provides methods for using any one or more of the vaccine compositions (indicated below as 'X') disclosed herein in the following methods.

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some instances, therapeutic compositions disclosed herein can be formulated for sale in the US, import into the US, and/or export from the US.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

EXAMPLES

Example 1: General Methods

Vector Construction

Figure 1C:
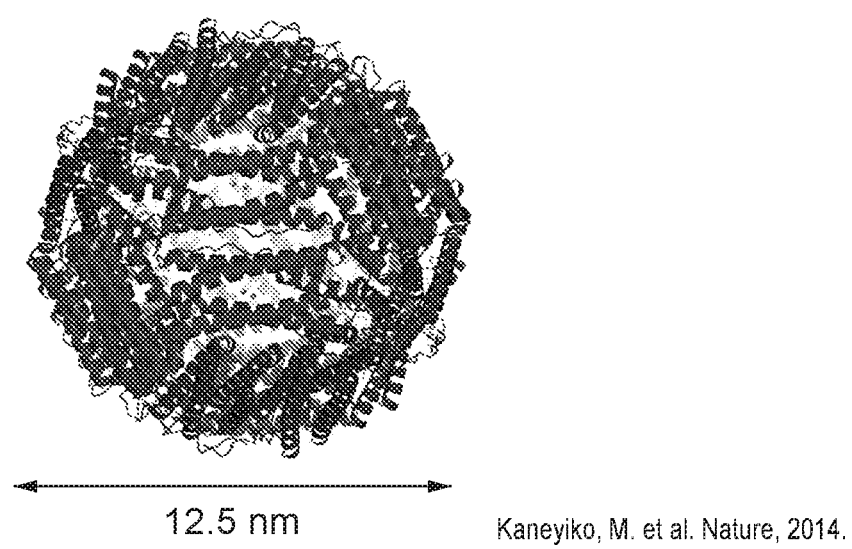
FIG. 1C is a schematic that depicts a ferritin particle.
Figure 1D:
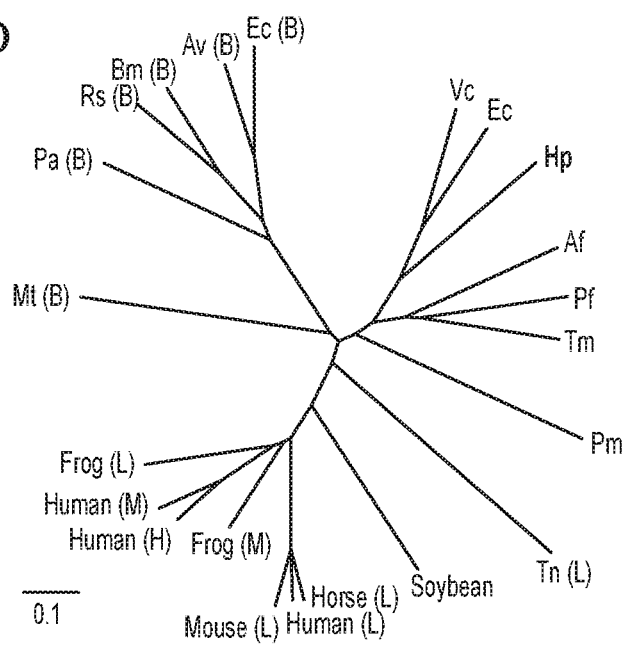
FIG. 1D is a schematic that depicts a map demonstrating cellular and humoral immune responses against human and mouse ferritin.
Figure 1D:
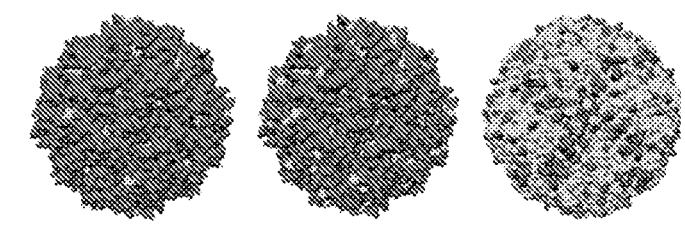
Figure 2A:
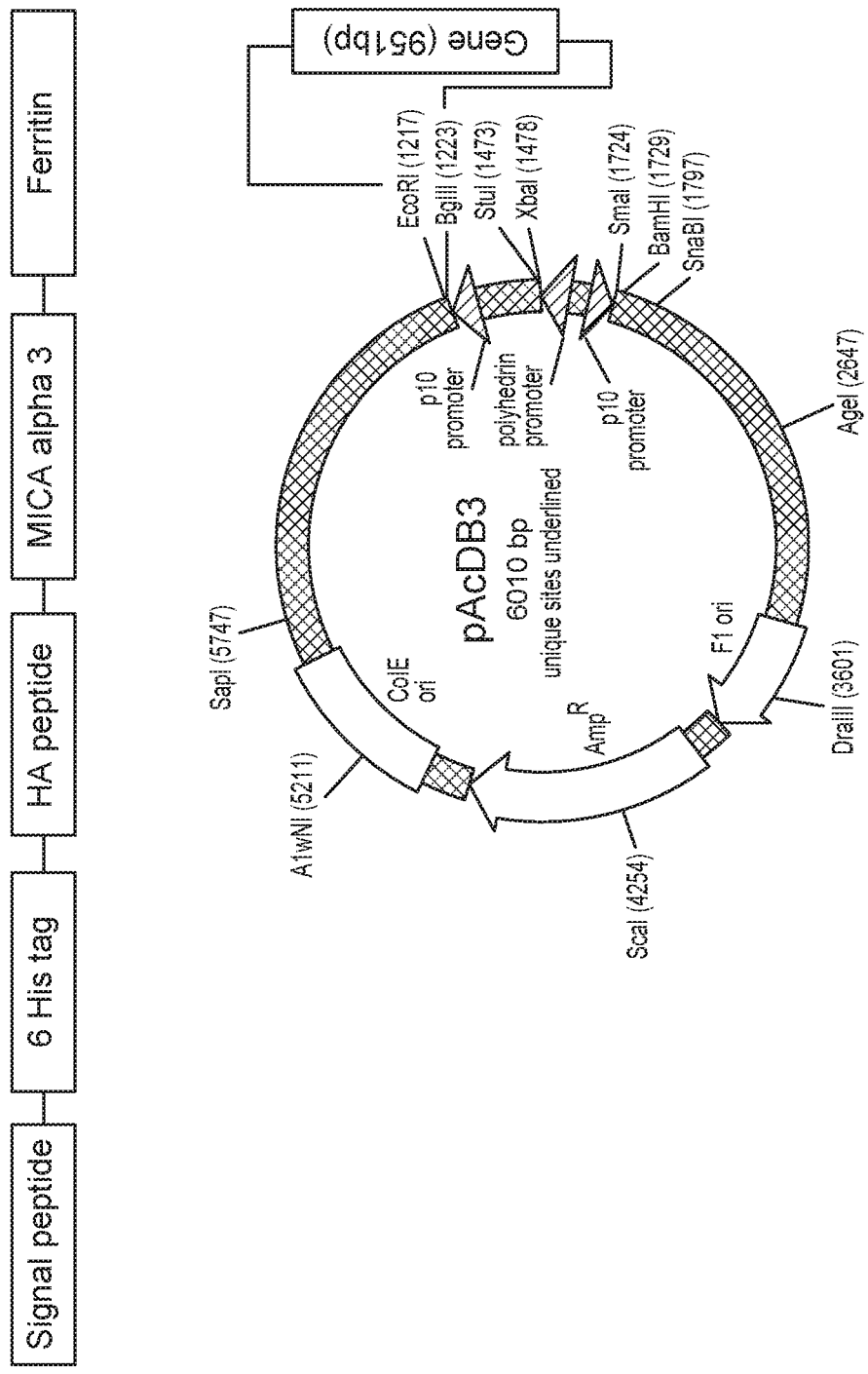
FIG. 2A is a schematic of the MICA alpha3 ferritin fusion gene construct.

Multivalent vaccines induce substantially higher-titer antibody responses than monovalent proteins. Herein is used a multivalent display in which the MICA alpha3 domain is fused to *Helicobacter pylori* (*H. pylori*) ferritin. Ferritin-based nanoparticles were recently shown to induce high-titer antibodies for influenza and EBV vaccines. Ferritin is found in most organisms as an iron storage protein. Ferritin is a self-assembling particle that forms a spherical particle with octahedral symmetry, consisting of 24 subunits. See FIGS. 1C and 1D for a schematic of a ferritin particle as well as a map demonstrating cellular and humoral immune responses against human and mouse ferritin. MICA alpha3 ferritin fusion gene (abbreviated as MICA-ferritin) was generated by fusing the gene encoding for α3 domain of MICA to *H. pylori* ferritin using a Gly-Ser-Gly linker (FIG. 2A). A point mutation (Asn19Gln) was introduced in the *H. pylori* ferritin to abolish a potential N-glycosylation site. To determine the antibody response of MICAα3 alone (without the ferritin), deglycosylated version of MICAα3 gene was generated by mutating 7 out of 8 potential N-glycosylation sites to Asp or Gln. A C-terminal HA tag was included for downstream protein purification purpose. The genes were synthesized using GeneArt® Gene Synthesis platform and codon optimized for insect cell expression. The synthesized genes were cloned into pAcDB3 baculovirus expression vector. (See FIG. 2C).

Figure 2B:
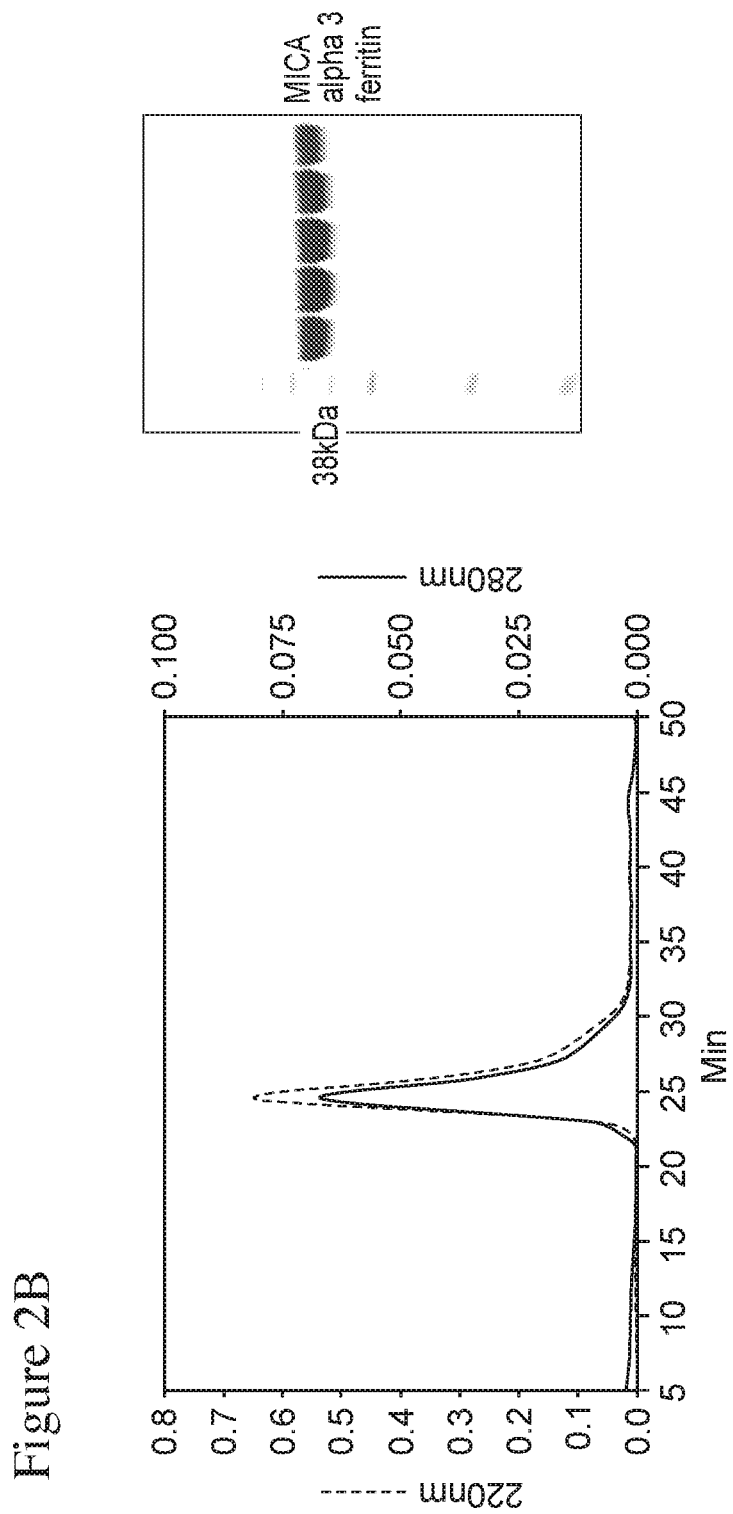
FIG. 2B is (Left) a size exclusion chromatogram of MICA alpha3-ferritin using XK16/60 Superdex200™ column (Flowrate: 2 ml/min; Running buffer: 50 mM Tris, 150 mM NaCl pH 7.5).
Figure 2C:
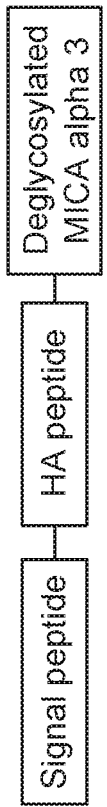
FIG. 2C is a schematic of the deglycosylated MICA alpha3 construct.
Figure 2C:
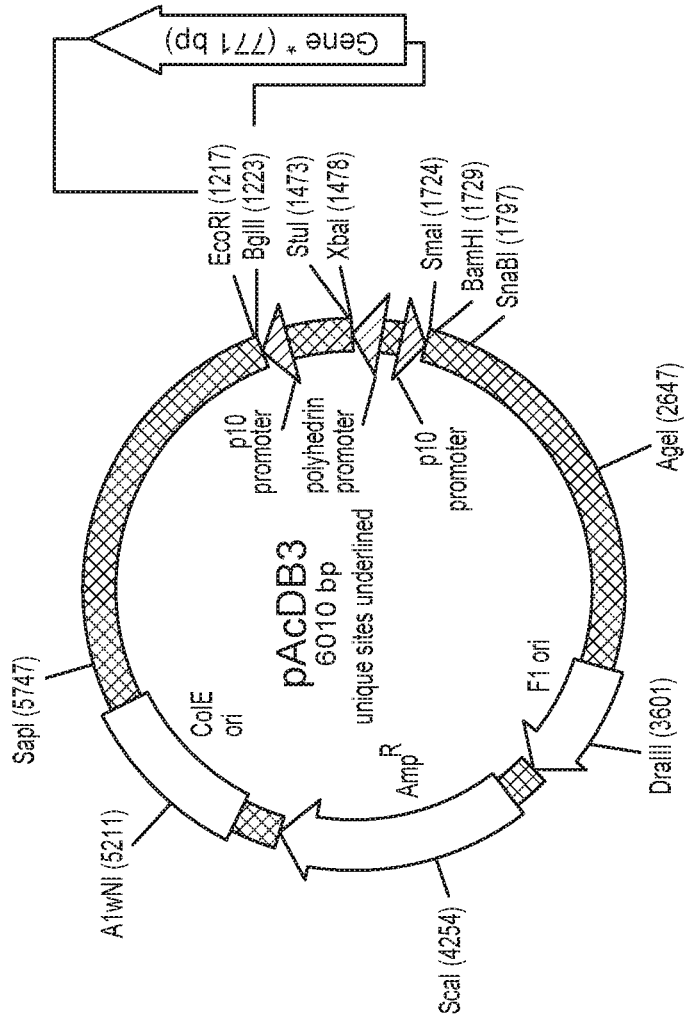
Figure 2D:
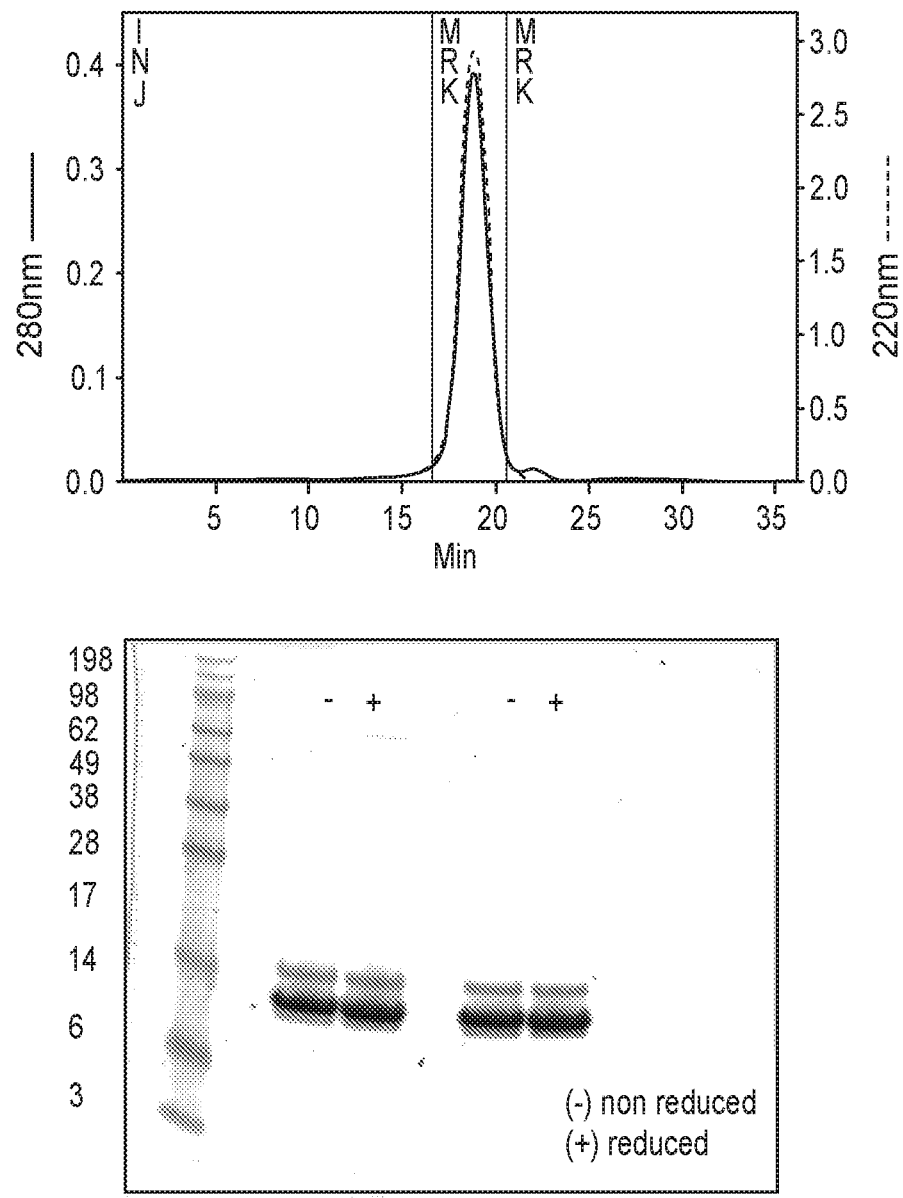
FIG. 2D is (Left) a size exclusion chromatogram of MICA alpha3 using Superdex200™ column (Flowrate: 1ml/min; Running buffer: 50 mM Tris, 150 mM NaCl pH 7.5).

Assays that demonstrate the generation of MIC alpha 3 domain vaccine and the generation of deglycosylated MICA alpha3 vaccine are presented in FIGS. 2B and 2D, respectively.

Protein Biosynthesis and Purification

MICAα3 and MICA-ferritin fusion proteins were expressed in Sf9 (*Spodoptera frugiperda*) insect cells by infecting these cells with recombinant baculovirus at a multiplicity of infection of 10. The cells were grown in Sf900 serum free expression medium (Life Technologies) and the cultured supernatants were collected 3 days post-transfection. The supernatants were concentrated and then exchanged into Tris buffer (50 mM Tris, 150 mM NaCl, pH 7.5 buffer). The proteins were purified by HA affinity chromatography and aggregates were removed by performing size exclusion chromatography using Superose 6 column (GE Healthcare). The purified proteins were buffer exchanged into PBS using PD-10 desalting columns (GE) and concentrated to 1 mg/ml using Amicon Ultra 4 ml centrifugal filters. Protein purity and size was verified by SDS-PAGE.

Preparation of MPS Vaccine and Immunization

The scaffold vaccine described here was recently reported (Kim et al *Nat. Biotechnol.* 2015, 33, 64-72). Mesoporous silica rods (MSR) injected with a needle spontaneously assembles in vivo to form a macroporous structure resembling a haystack that provides a 3D cellular microenvironment for dendritic cells. This biodegradable scaffold recruits and educates dendritic cells which then migrate to lymph nodes where they induce an immune response. 5 mg of MSR was loaded with 1 µg of GM-CSF (to recruit dendritic cells), 100 µg of CpG oligonucleotide (to induce dendritic cell activation) and 200 µg of MICA-ferritin fusion or a control protein (ovalbumin) for 12 hours at room temperature. The particles were lyophilized, resuspended in PBS and injected subcutaneously into the flank of C57BL/6 mice. Mice receive a boost on days 14 or 21 following initial immunization. Age matched non-immunized mice (naïve) and mice immunized with ovalbumin were be used as control groups for the MICA-ferritin immunization experiments. As an additional control in the MICAα3 experiment, mice were immunized with all vaccine components but without the MSR scaffold (bolus).

Lung Metastasis Experiment in MICAα3 and MICA Ferritin Immunized Mice

C57B1/6J mice were immunized with MICAα3 or MICAα-ferritin vaccine. Three weeks after the boost, mice were challenged with intra venous (i.v) injection of $0.5 \times 10^6$ MICA expressing B16F10 melanoma cells. Sera were collected prior to tumor challenge and at weekly intervals to analyze shed MICA levels. Mice were euthanized 14 days after tumor challenge; lungs were harvested and fixed in 10% neutral-buffered formalin and the number of pulmonary metastases was quantified.

Flow Cytometric Analysis and ELISA to Determine the MICA Antibody Titers in Immunized Mice MICA specific antibody titers were tested by ELISA using the full length extracellular domain of MICA. Full length MICA protein (0.2 µg) was coated on 96 well ELISA plate overnight at 4° C. The plates were blocked for an hour at room temperature with PBS/2% BSA. The plates were washed and incubated with serial dilution of sera collected at weekly intervals from each experimental group. Goat anti-mouse HRP was used as detection antibody. Flow cytometric analysis was used to assess the binding of serum antibodies to full length expressed on the surface of tumor cells. Briefly, $1 \times 10^5$ tumor cells were incubated with 1 µl of serum for 2 hrs at 4° C. $1 \times 10^5$ cells were stained with 1 µl of serum from non-immunized mice (naïve), mice immunized with vaccine components without the MSR scaffold (bolus) or MICA-ferritin vaccine (vaccinated) in 100 µl of PBS for 2 hours. Commercially available monoclonal antibody 6D4 that binds to the alpha1-alpha2 domains of MICA was used as a positive control (10 µg). PE conjugated anti-mouse IgG was used as secondary antibody.

Example 2: Scaffold Vaccine for Induction of Potent Immune Response

Figure 3:
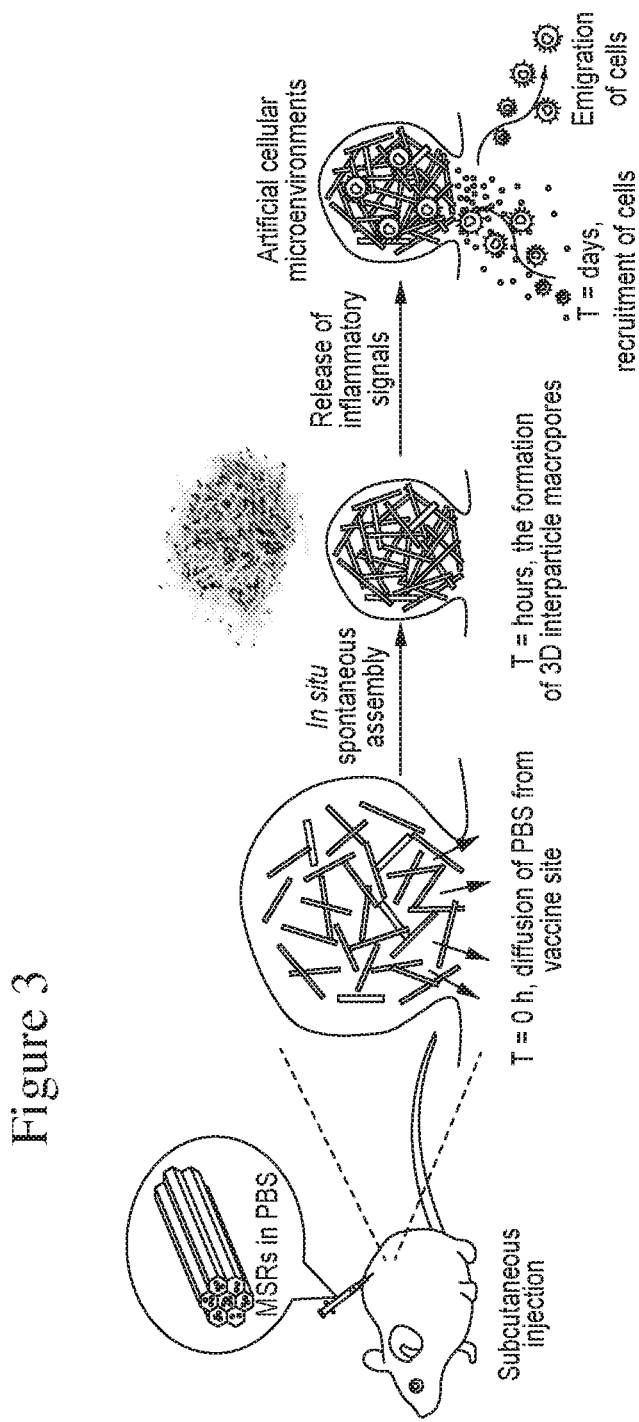
FIG. 3 is a schematic that depicts the use of Mesoporous silica rods (MSR) vaccine for subcutaneous injection, and the resulting induction of potent immune responses. See Kim, J & Aileen, W. L. et al. *Nature Biotech.* 2015.

The MIC α3 domain was expressed as a recombinant protein in the Baculovirus system; the protein was displayed in a multivalent form on *H. pylori* ferritin, an iron storage protein with 24 identical subunits. A vaccination approached using mesoporous silica rods (MSRs) originally described in Kim et al *Nat. Biotechnol.* 2015, 33, 64-72 was used herein, and is hereby incorporated by reference in its entirety (see FIG. 3). MSRs that are injected subcutaneously with a needle spontaneously assemble in vivo into macroporous structures that provide a 3D cellular microenvironment for host immune cells. This system recruits large numbers of immune cells, exposes them to the relevant antigens and also provides the appropriate molecular cues for induction of a potent immune response. The MIC α3 domain protein was absorbed to MSRs, along with GM-CSF (for recruitment of dendritic cells) and CpG oligonucleotide (an adjuvant that activates dendritic cells). This vaccination approach enabled induction of high-titer antibodies specific to the MIC α3 domain. These antibodies stained tumor cells that express MIC and inhibited shedding of MIC by tumor cells.

Figure 4B:
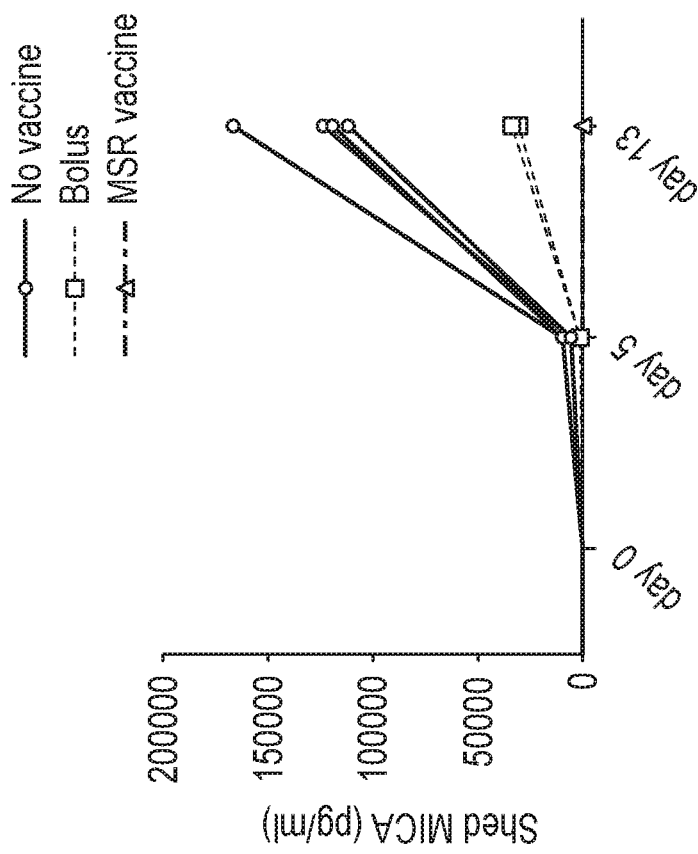
FIGS. 4A and 4B are a series of graphs that depict the efficacy of MIC α3 domain vaccine in a lung metastasis model. The data presented in FIG. 4A was obtained as follows. B6 mice were immunized with 200 µg of MIC α3 protein, 1 µg of GM-CSF and 100 µg of CpG-ODN, either as a bolus without scaffold (bolus) or within the mesoporous silica rods (MSR) scaffold (MSR vaccine). Mice received one booster injection on day 28. Three weeks later, mice were challenged by i.v. injection of $5\times10^5$ B16-MIC tumor cells. The number of lung metastases was quantified on day 14 following tumor cell injection. The data obtained in FIG. 4B was obtained as follows. Shed MIC was quantified by ELISA on days 0, 5, and 13 following tumor cell injection. Prior experiments had shown that MIC α3 domain specific antibodies do not interfere with ELISA used to detect shed MIC.
Figure 4A:
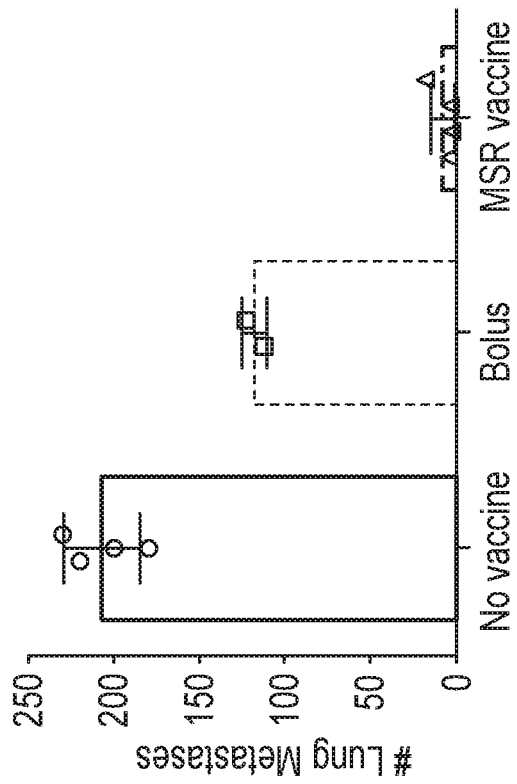

To test the anti-tumor activity of this vaccine, we utilized B16 melanoma cells transfected with human MIC. When these tumor cells are injected intravenously into non-immunized mice, they form large numbers of lung metastases (~200 metastases/mouse). The MSR scaffold vaccine provided potent protection from the outgrowth of such metastases. When the vaccine components were injected as a bolus without the MSR scaffold, partial protection was observed, but the biological effect was significantly weaker. This result shows that local recruitment of immune cells to the MSR scaffold greatly enhances the activity of this vaccine. (See FIG. 4).

Figure 5A:
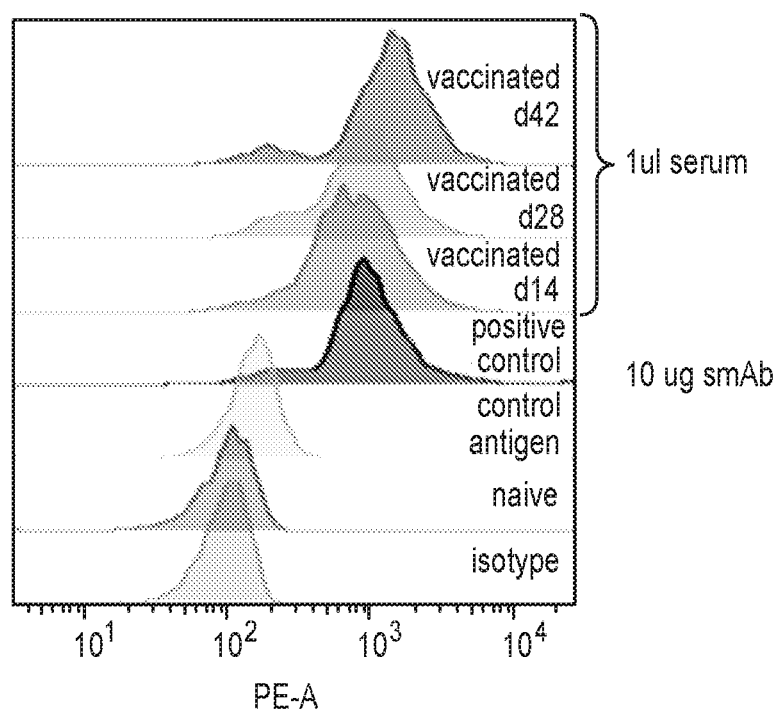
FIGS. 5A and 5B are a series of plots and graphs that demonstrate vaccination with MICA-ferritin fusion protein induces high-titers of MICA specific antibodies.
Figure 5B:
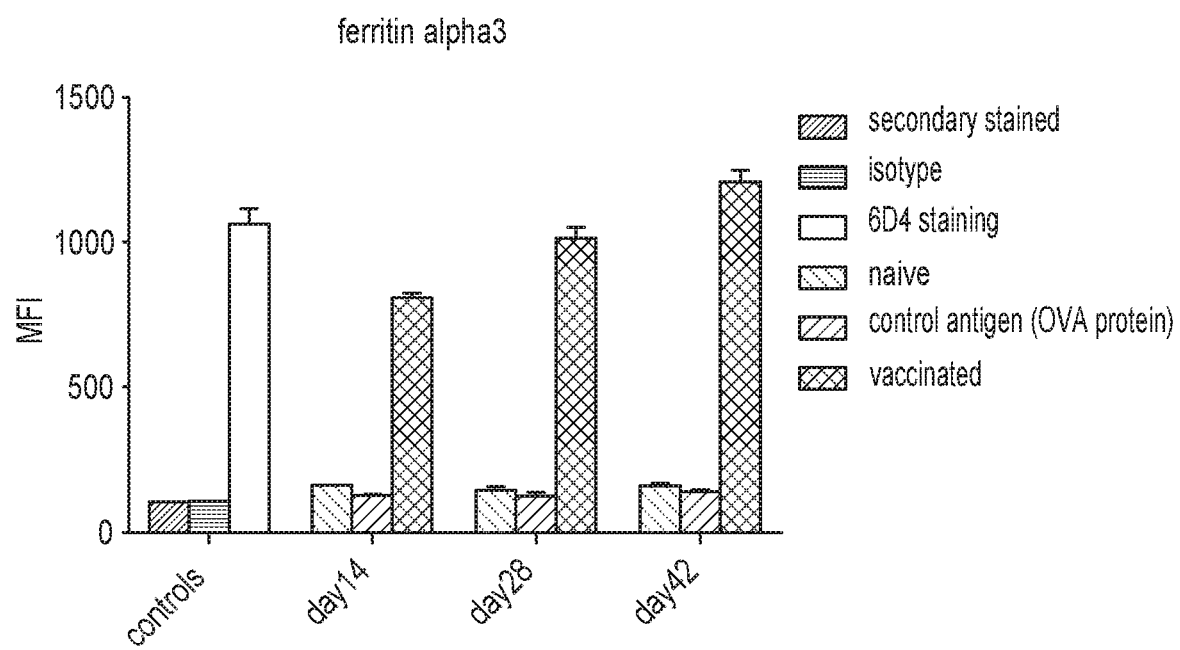

Example 3: Vaccination with Mica-Ferritin Fusion Protein Induces High-Titers of Mica Specific Antibodies Binding of MICAα3 specific antibodies in the sera of immunized mice to full length MICA expressed on the surface of B16F10 mouse melanoma cells was tested by flow cytometry. Briefly, $1\times10^5$ cells were stained with 1 μl of serum from non-immunized mice (naïve), mice immunized with control vaccine (OVA-protein) or MICA-ferritin vaccine from days 14, 28 and 42 (vaccinated) in 100 μl of PBS for 2 hours. Commercially available monoclonal antibody 6D4 that binds to the α1-α2 domains of MICA was used as a positive control (10 μg). PE conjugated anti-mouse IgG was used as secondary antibody. MICAα3 specific antibodies in the sera of vaccinated mice (histograms—green (d14), blue (d28), red (d42) showed significant binding to MICA expressed on the tumor cell surface (FIGS. 5A and 5B). The results of these assays demonstrate that MICA-feritin fusion protein vaccination induces high-titers of MICA specific antibodies.

Example 4: Vaccination with Mica-Ferritin Fusion Protein Generates High Levels of IgG1, IgG2a and IgG3 MICAa3 Specific Polyclonal Antibody Response Sera from MICA-ferritin immunized mice were tested in ELISA to determine the different subclasses of IgGs induced upon vaccination. Sera from mice immunized with OVA-protein (bolus) or non-immunized mice (naive) were used as control groups. Full length MICA was used as the capture antigen and a serum dilution of 1/1000 was used in each well. HRP conjugated anti-mouse IgG1, IgG2a, IgG2b or IgG3 were used for detection. Immunization with MICA-ferritin (vaccinated) was found to induce high levels of all the IgG subclasses tested (See FIG. 6).

Example 5: Polyclonal Antibodies Generated in Response to the MICA-Ferritin Vaccine Prevent MICA Shedding from the Surface of Human Metastatic Melanoma Cell Line Induction of MICA antibodies in melanoma patients treated with autologous tumor vaccine (GVAX) plus Ipilimumab, correlated with reduced serum soluble MICA (sMICA) levels. The extracellular part of MICAS contains two MHC class I-like domains (α1 and α2) and a membrane-proximal immunoglobulin domain (α3). It has been shown that the disulfide isomerase ERp5 cleaves the structural disulfide bond in the MICA α3 domain, and the resulting unfolding of this domain allows proteolytic cleavage by ADAM 10, ADAM 17 and MMP-14. The purpose of this assay was to determine whether the polyclonal antibodies generated in response to the MICA-ferritin vaccine prevents MICA shedding from the human melanoma tumor cell line A375.

Figure 7:
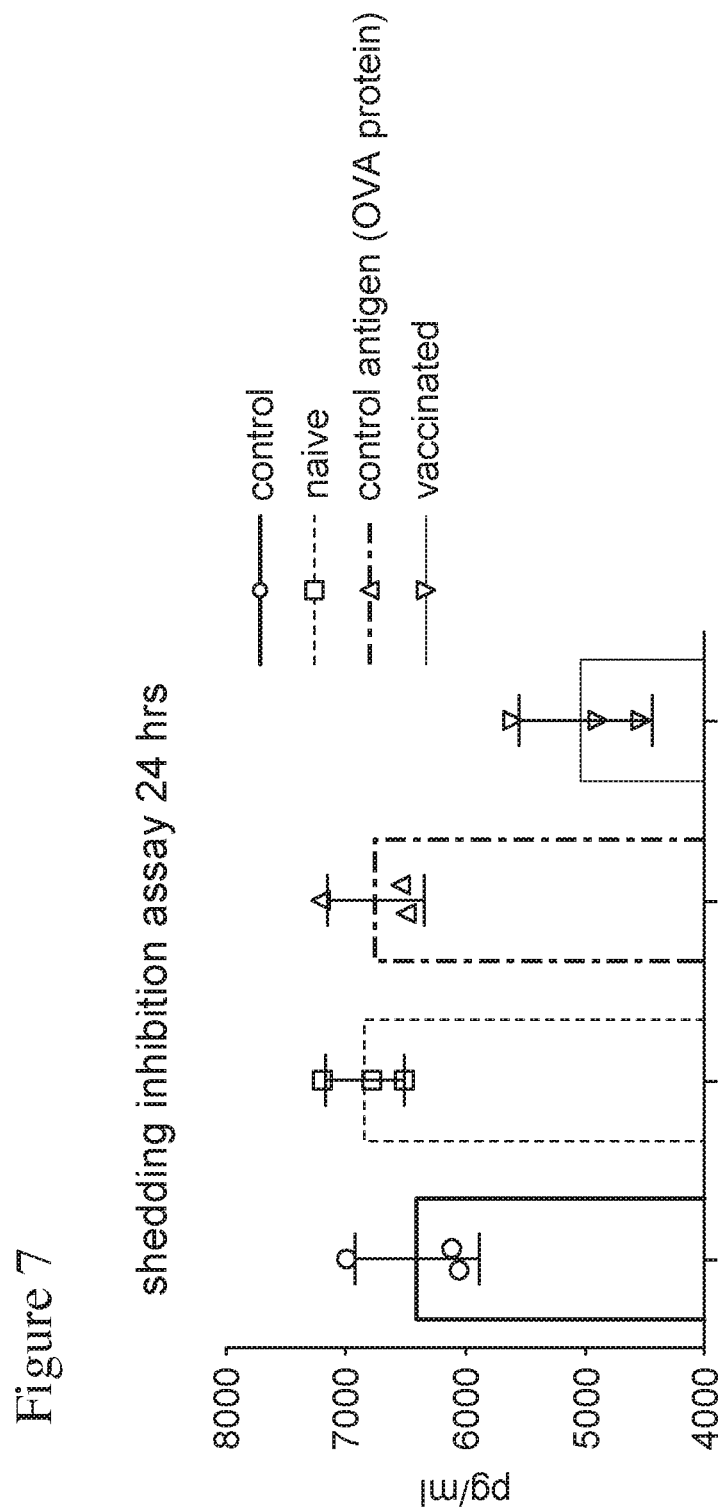
FIG. 7 is a graph demonstrating that serum antibodies in the MICA-ferritin immunized group prevent MICA shedding from the tumor cell surface.

For these assays, $4\times10^5$ A375 malignant melanoma cells were plated in 96 well plate with 200 μl of media. The cells were incubated with no serum or with serum from naïve, OVA-protein immunized or MICA-ferritin vaccinated mice (FIG. 7 bars with inverted triangle) for 24 hrs. sMICA in the supernatant was analyzed using MICA ELISA kit which utilizes MICA α1-α2 domain antibodies for capture and detection. Lower levels of sMICA was detected in the supernatant of cells incubated with serum from MICA-ferritin vaccinated mice (FIG. 7 bars with inverted triangle) compared to cells that were incubated without serum, serum from naïve (FIG. 7 bars with circles and squares) or OVA-protein immunized mice (FIG. 7 bars with triangle), thus indicating that the MICAα3 specific antibodies can inhibit the shedding of MICA from tumor cell surface.

Example 6: Therapeutic Activity of Mica-Ferritin Vaccine

The therapeutic activity of the MICA-ferritin vaccine was tested using highly aggressive B16F10 melanoma tumor model. B16F10 melanoma tumor cells were genetically modified to express human MICA. MICA is bound by the murine NKG2D receptor, making this a suitable model system. C57BL/6 mice immunized with the MICA-ferritin vaccine, OVA-protein vaccine (control antigen) and non-immunized control mice (age and sex matched) were challenged with i.v injection of B16F10-MICA tumor cells. Sera were collected prior to tumor challenge, on day 7 and day 13. Mice were euthanized 14 days after tumor challenge and the number of pulmonary metastases was quantified (See FIG. 8A).

Figure 8A:
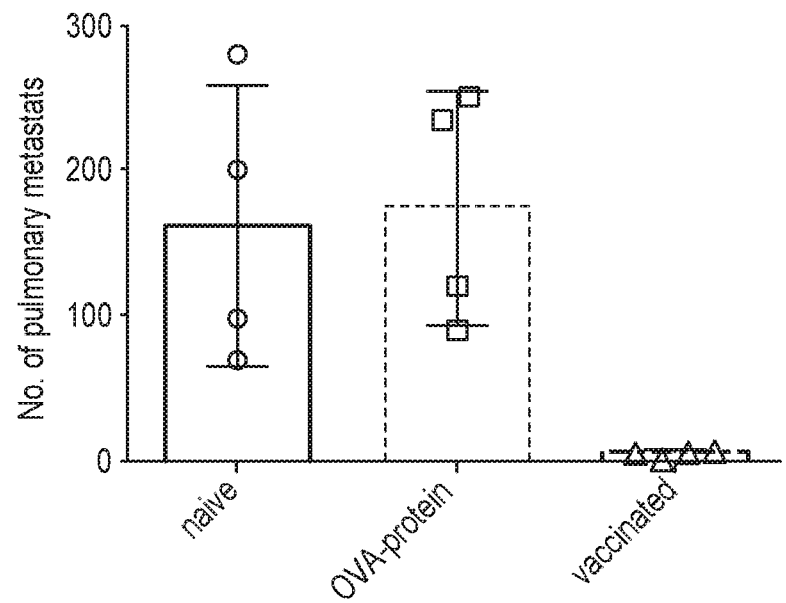
FIGS. 8A and 8B are a series of graphs that depict the therapeutic activity of MICA-ferritin vaccine. C57BL/6 mice were immunized with MICA α3—ferritin or ovalbumin and received a booster injection on day 28. Mice were challenged by intravenous injection of $5\times10^5$ B16-MICA tumor cells which form lung metastases. The number of lung metastases were counted on day 14 (FIG. 8A) and shed MICA was quantified in the serum (FIG. 8B). The MICA α3 domain vaccine substantially reduced the number of lung metastases while the control vaccine had no effect. Also, shed MICA became undetectable in the serum of mice that had received the MICA α3—ferritin vaccine while shed MICA levels were very high in both control groups.
Figure 8B:
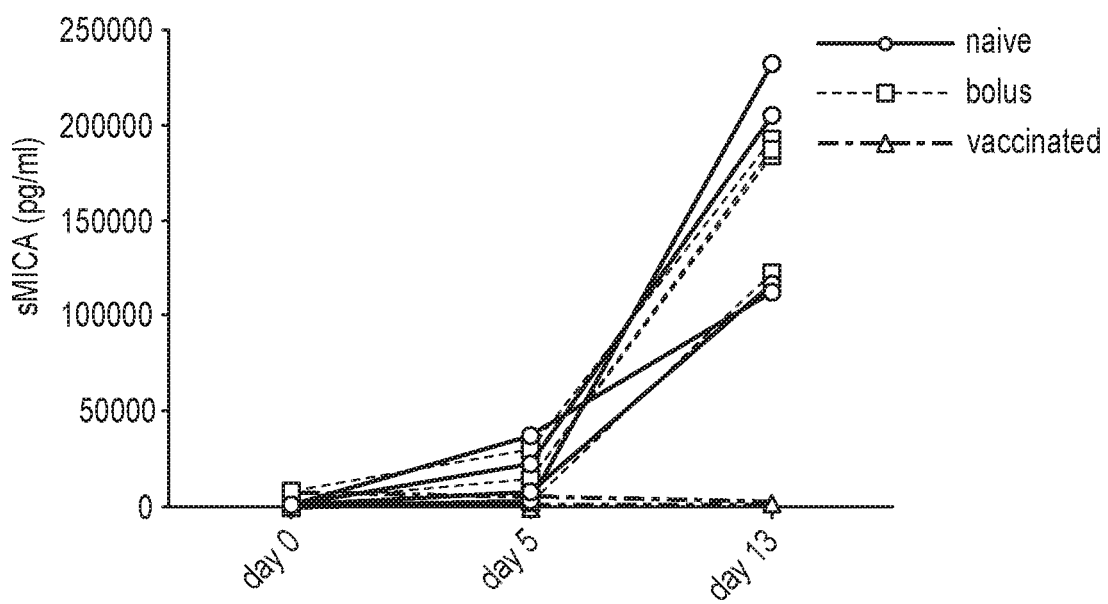

For these assays, 8 week old C57BL/6 female mice were immunized with MICA alpha3-ferritin or ova-protein followed by a boost on day 28. Three weeks later, mice were challenged by i.v. of $5\times10^5$ MICA-expressing B16F10 melanoma cells. Mice were euthanized 14 days after tumor challenge and the number of pulmonary metastases was quantified. Shed MICA (sMICA) level in the sera was monitored by ELISA. These experiments demonstrated that MICA-ferritin vaccinated mice were nearly tumor free. In contrast, non-immunized age-matched control group (naïve) and mice vaccinated with control antigen-ovalbumin had large numbers of lung metastases (average of ~150 lung mets/mouse) (FIG. 8A). Importantly, sMICA was undetectable in sera of mice immunized with MICA-ferritin vaccine (triangle) while high levels of sMICA were detected within two weeks after tumor challenge in the sera of mice immunized with ovalbumin (square) and the non-immunized control group (circle) (FIG. 8B).

Example 7: Determining Effective Dosage of MICA-Ferritin Vaccine and Kinetics of Polyclonal Antibody Response In Vivo For these studies, mice received two injections of the vaccine prior to tumor cell challenge. However, near-maximal antibody levels are already achieved two weeks following initial immunization. In order to determine the optimal vaccination dosage and kinetics of polyclonal antibody response at different doses, C57B1/6J mice were immunized different doses of MICA-ferritin protein (50-200 µg) absorbed to MSR. The mice received boost on day 17. Sera were collected at weekly intervals by retro-orbital bleeding to determine the MICA antibody titers by ELISA. On day 25 following initial immunization, mice were challenged with i.v. injection of MICA expressing B16F10 melanoma cells. Sera were collected prior to tumor challenge and at weekly intervals to analyze shed MICA levels. Mice were euthanized 14 days after tumor challenge; lungs were harvested and fixed in 10% neutral-buffered formalin and the number of pulmonary metastases was quantified.

Figure 9A:
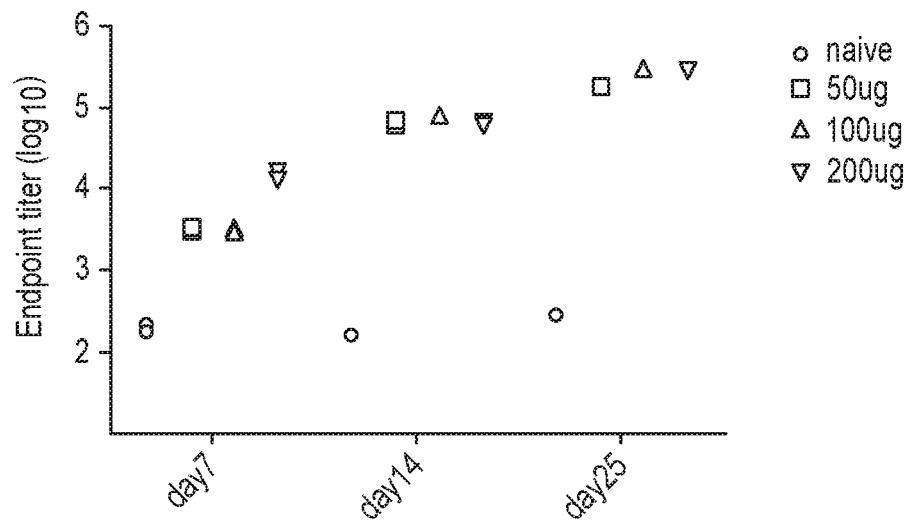
FIGS. 9A-9C are a series of graphs that depict the titer of antibodies induced by the MICA-ferritin vaccine (FIG. 9A) as well as the effect of the vaccine dosage on the number of pulmonary nodules (FIG. 9B) and in the amount of sMICA (FIG. 9C).

For these studies, 8 week old C57BL/6 female mice were immunized with MICA alpha3-ferritin vaccine at different doses (50 µg, 100 µg or 200 µg) and boosted on day 17. End point antibody titer was determined by serially diluting the sera and testing its binding to full length MICA protein by ELISA. MICA-ferritin immunized mice elicited high levels of antibody titers by day 14 (ELISA endpoint titers of $10^5$) at all doses tested and the titer increased by 1000 fold after boost on day 17. Naïve, untreated age matched mice were used as control group (See FIG. 9A).

Figure 9B:
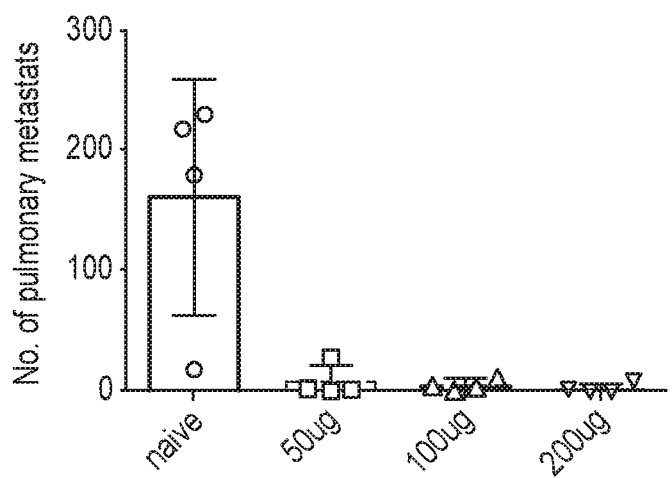
Figure 9C:
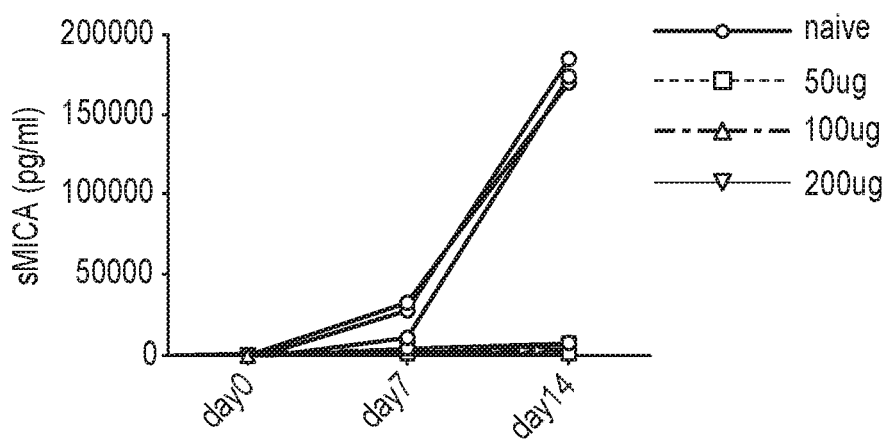

On day 25 following initial immunization, mice were challenged with i.v. injection of $0.5\times10^6$ MICA expressing B16F10 melanoma cells. Sera were collected prior to tumor challenge and at weekly intervals to analyze shed MICA levels. Mice were euthanized 14 days after tumor challenge; lungs were harvested and fixed in 10% neutral-buffered formalin and the number of pulmonary metastases was quantified. Mice immunized with 100 µg and 200 µg were nearly tumor free compared to mice immunized with 50 µg of the vaccine (~2-12 lung mets). sMICA was undetectable in the sera of mice immunized with different doses of MICA-ferritin vaccine (50 µg—square, 100 µg—upward triangle, 200 µg—downward triangle) while high levels of sMICA were detected within two weeks after tumor challenge in the sera non-immunized control group (empty circle) (see FIGS. 9B and 9C).

Example 8: MICAa3 Vaccine Alone Induces High-Titers of MICA Specific Antibodies

To determine the effect of MICAα3 vaccine alone (without ferritin) in generating MICA specific polyclonal antibody response, deglycosylated version of MICAα3 gene was generated by mutating 7 out of 8 potential N-glycosylation sites to Asp or Gln. Following protein production and purification as described in the methods section, MICAα3 vaccine was prepared by loading 5 mg of MSR with 1 µg GM-CSF, 100 µg CpG-ODN and 150 µg of deglycosylated MICAα3 protein (abbreviated MICAα3 vaccine). The particles were then lyophilized, re-suspended in cold PBS (150 µl) and injected subcutaneously into the flank of female C57B1/6J mice. Mice immunized with all vaccine components but without the MSR scaffold (bolus) and untreated, age matched mice were used as control groups. Sera were collected at weekly intervals by retro-orbital bleeding. The mice received boost on day 28 following initial immunization.

Figure 10A:
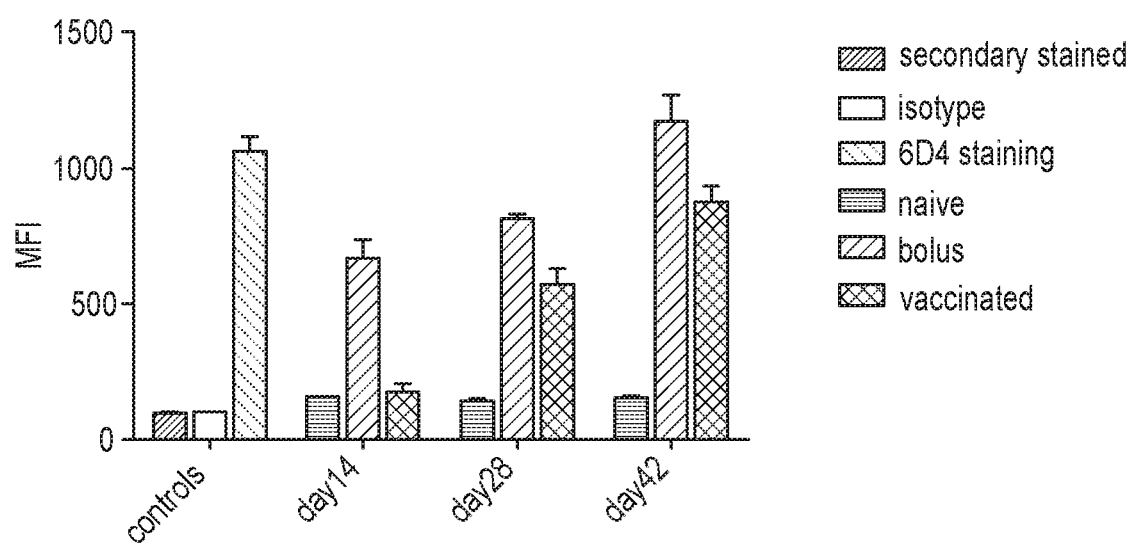
FIGS. 10A and 10B are a series of graphs that depict the effect of the deglycosylated version of the MICAα3 vaccine (not linked to ferritin nanoparticle) on binding of MICAα3 specific antibodies in the sera of immunized mice to full length MICA expressed on the surface of B16F10 mouse melanoma cells tested by Flow Cytometry (FIG. 10A), as well as graphs that depict results from ELISA assays that were used to determine the different subclasses of IgGs induced upon vaccination (FIG. 10B).

For these studies, $1\times10^5$ MICA009 expressing B16F10 melanoma cells were stained with 1 µl of serum from non-immunized mice (naïve), mice immunized with MICAα3 without MSR (bolus) or MICAα3 vaccine (vaccinated) in 100 µl of PBS for 2 hours. Commercially available monoclonal antibody 6D4 that binds to the α1-α2 domains of MICA was used as a positive control (10 µg). PE conjugated anti-mouse IgG was used as secondary antibody. MICAα3 specific antibodies in the sera of vaccinated mice and bolus group showed significant binding to MICA expressed on the tumor cell surface, with levels similar to the positive control group following boost (See FIG. 10A).

Figure 10B:
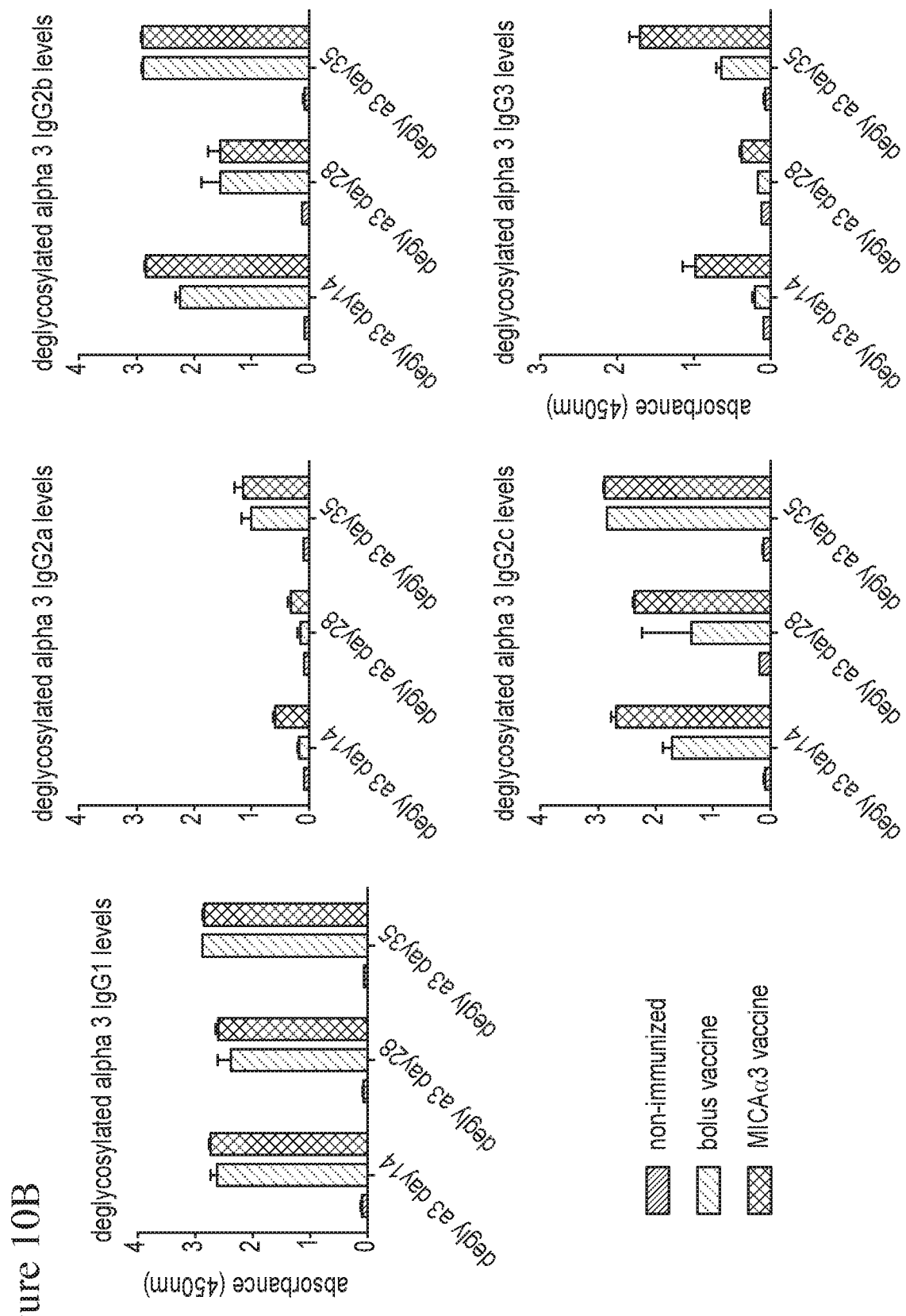

Sera from MICAα3 immunized mice were tested in ELISA to determine the different subclasses of IgGs induced upon vaccination. Sera from non-immunized mice were used as control groups. Full length MICA was used as the capture antigen and a serum dilution of 1/1000 was used in each well. HRP conjugated anti-mouse IgG1, IgG2a, IgG2b or IgG3 were used for detection. Immunization with MICAα3 vaccine and the bolus vaccine were found to induce the production of all the IgG subclasses tested, with IgG1 levels higher than the MICA-ferritin vaccine (See FIG. 10B).

Figure 11A:
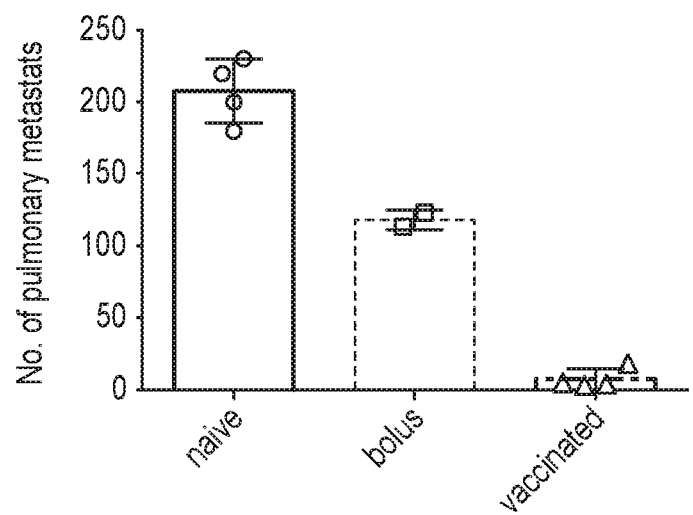
FIGS. 11A and 11B are a series of graphs that depict MICAα3 vaccine alone (without ferritin fusion) has significant therapeutic benefit in vivo.
Figure 11B:
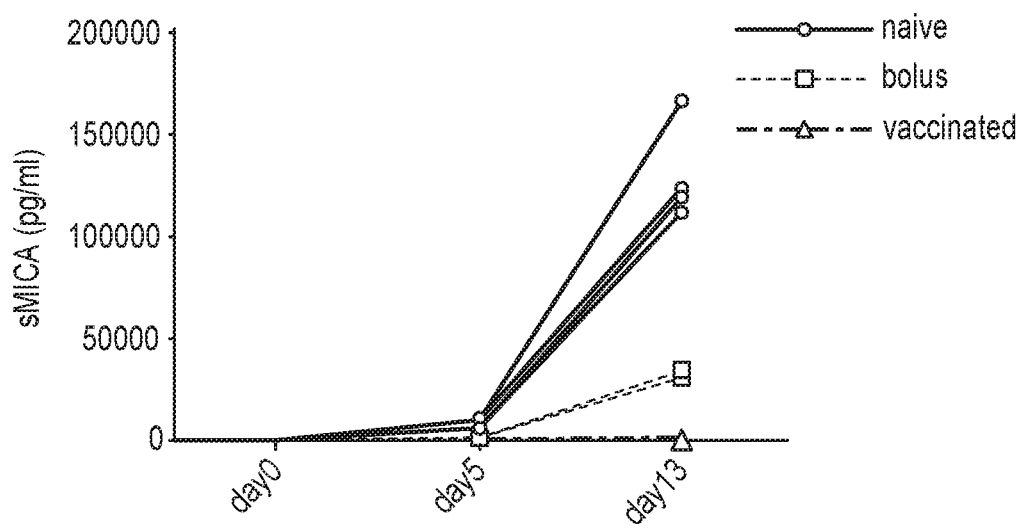
Figure 12A:
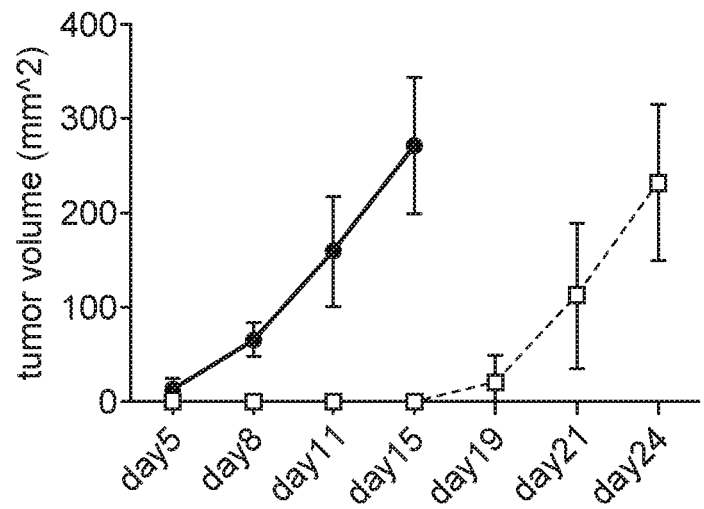
FIGS. 12A and 12B show that MICA-ferritin vaccine delays tumor growth in B16F10 subcutaneous melanoma model.
Figure 12B:
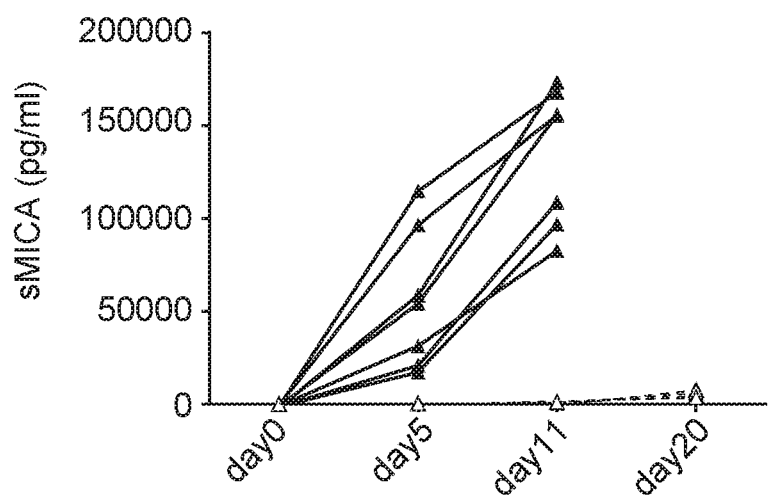
Figure 13A:
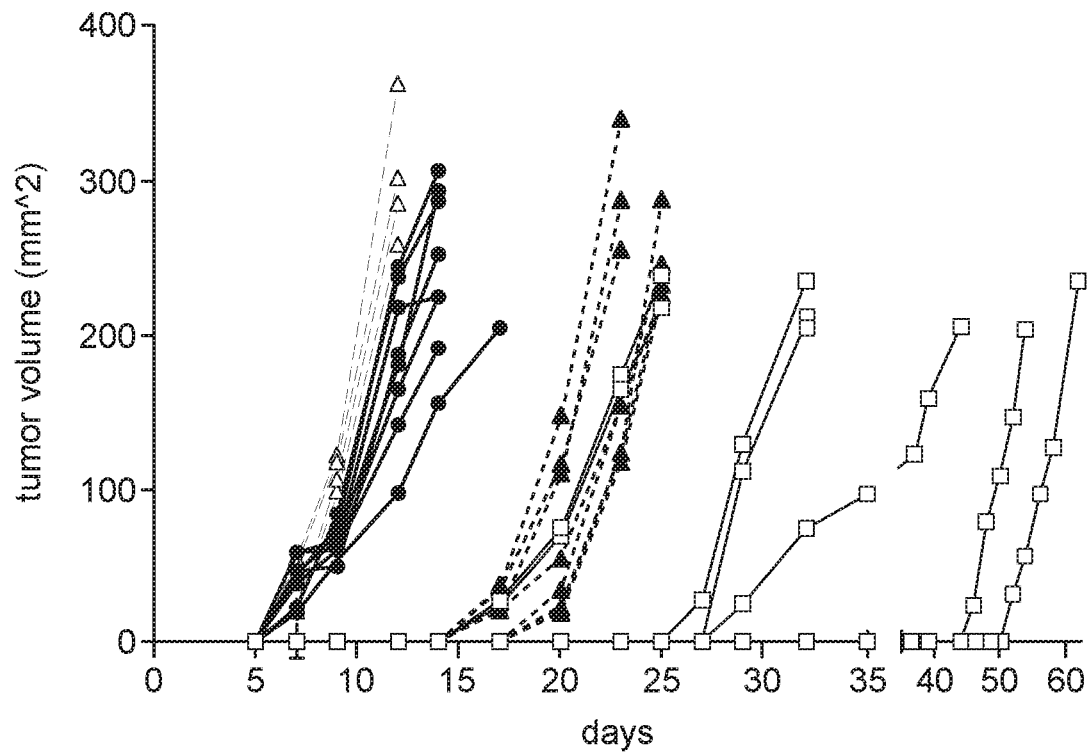
FIGS. 13A and 13B show that depletion of CD8 T cells accelerates tumor growth in MICA-ferritin vaccinated B16F10 subcutaneous melanoma model.
Figure 13B:
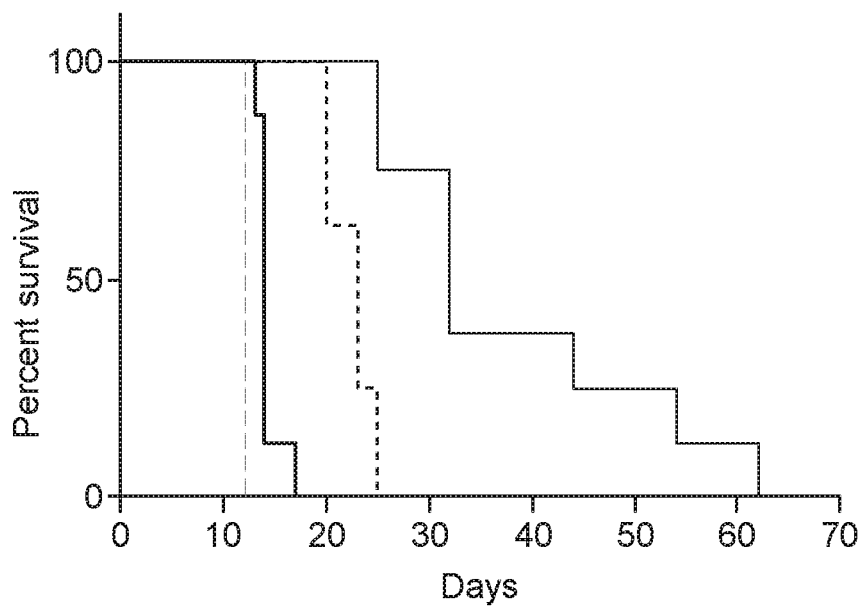
Figure 14A:
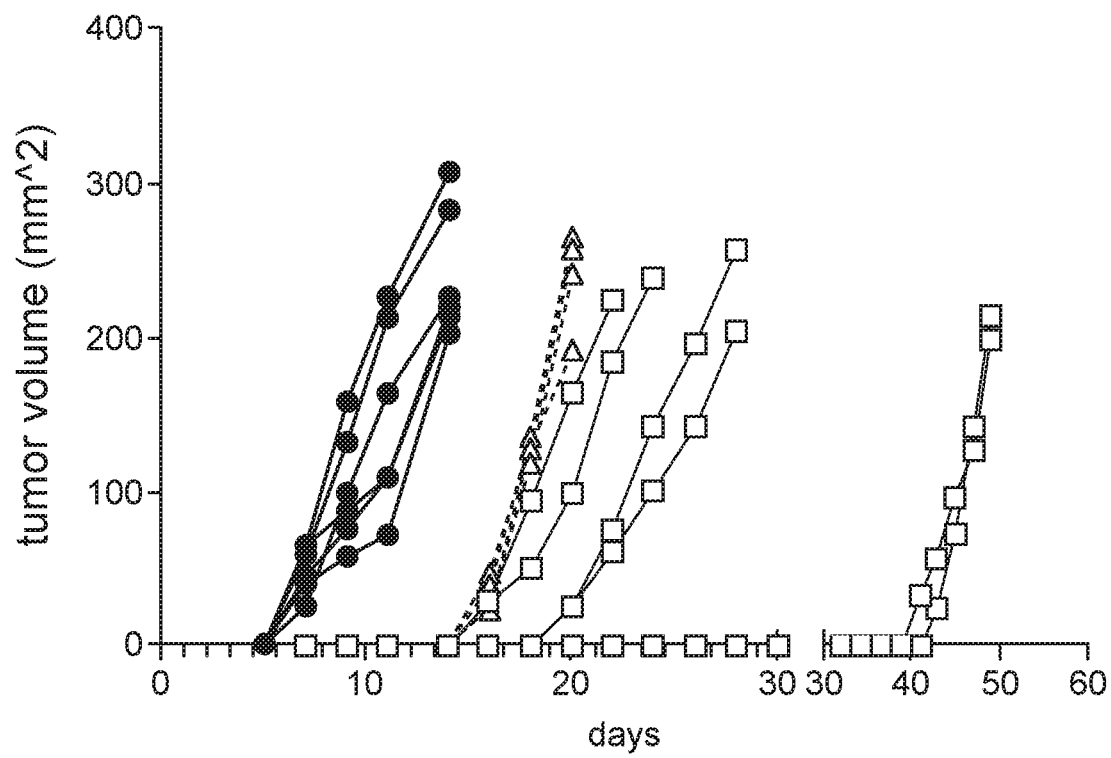
FIGS. 14A and 14B show that NK cells contribute to the therapeutic effect of MICA-ferritin vaccine in B16F10 subcutaneous melanoma model.
Figure 14B:
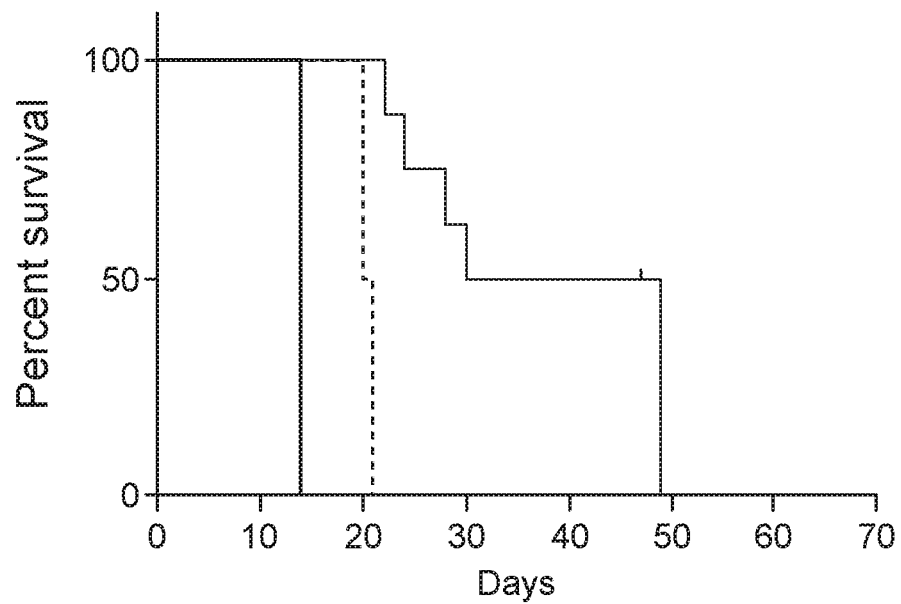
Figure 15A:
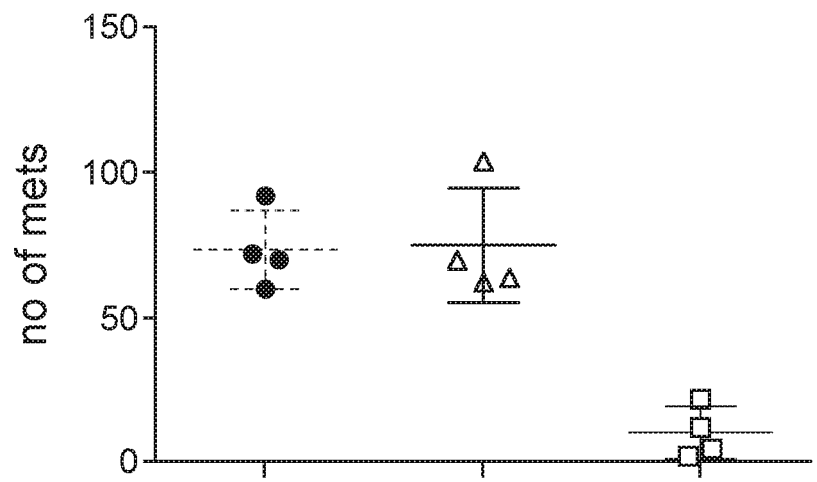
FIGS. 15A and 15B show that serum polyclonal antibodies generated in response to MICA-ferritin vaccine prevent pulmonary metastasis of B16F10-MICA tumor cells.
Figure 15B:
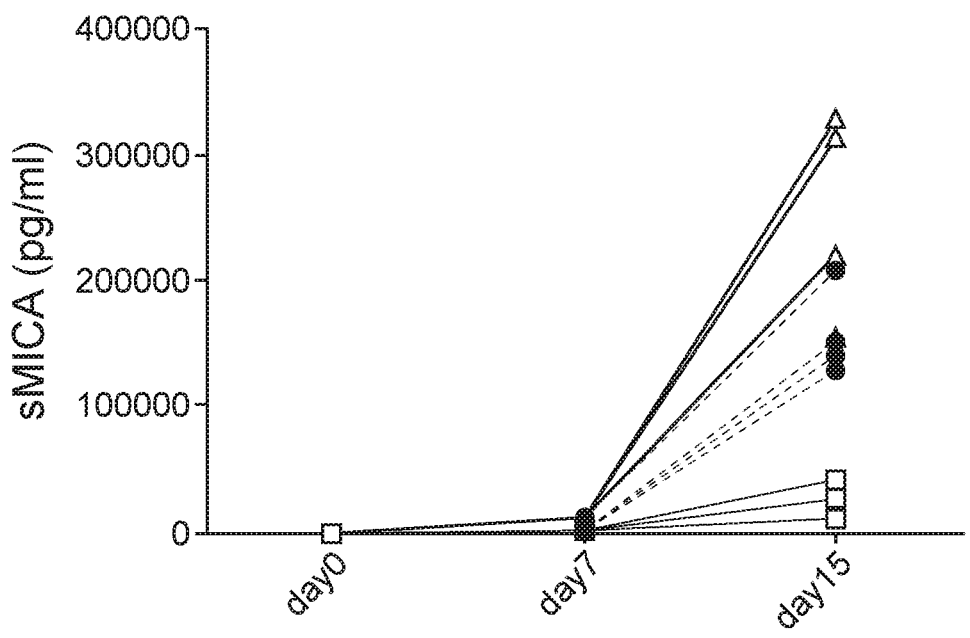
Figure 16A:
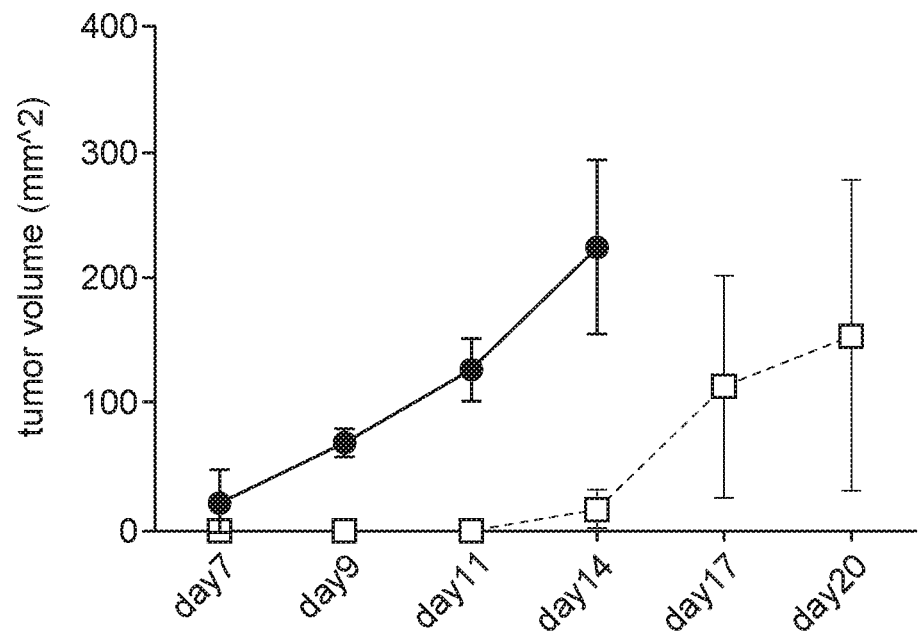
FIGS. 16A and 16B show that MICA-ferritin vaccine also controls B16F10-MICB005 subcutaneous tumor growth.
Figure 16B:
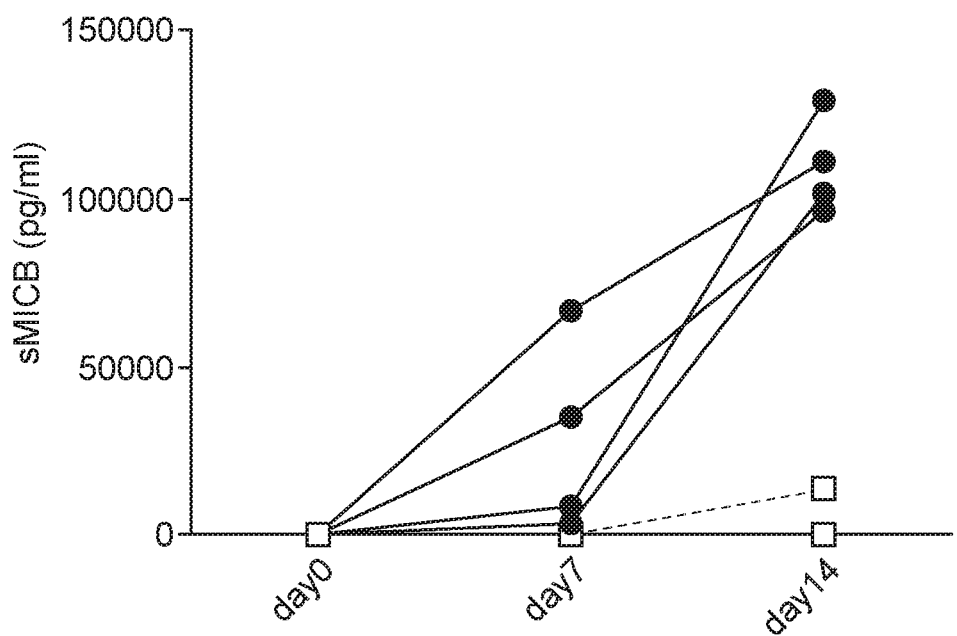
Figure 17:
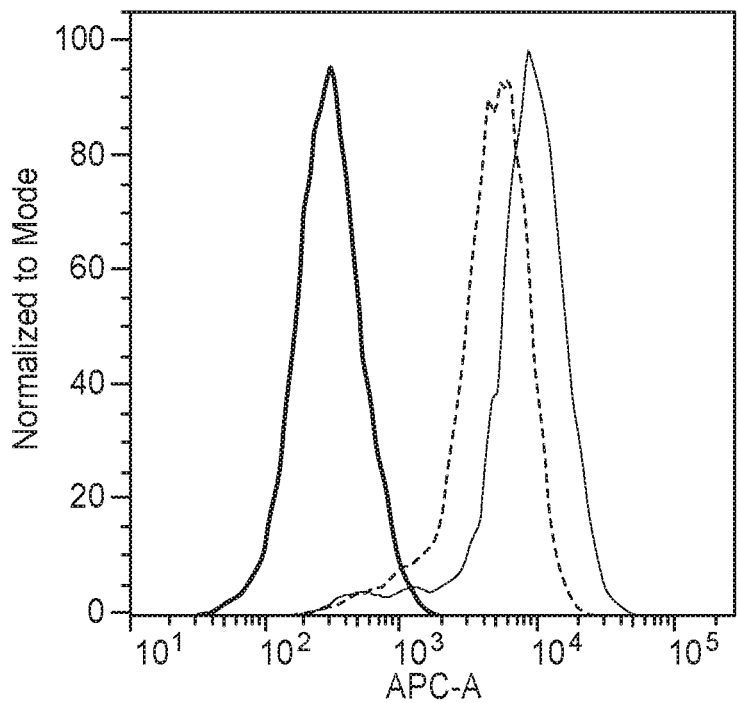
FIG. 17 is a series of graphs showing the staining of B16 cell lines that express MICA with sera from mice immunized with MICA-ferritin vaccine formulated with mesoporous silica rods (MSR) (dashed line) or direct conjugation of CpG to MICA-ferritin (without MSR (thin solid line). These data illustrate that vaccination with CpG directly conjugated to MICA-ferritin peptide induces a stronger immune response to the MICA alpha 3 domain than the vaccine formulated with MSR scaffold. For MSR vaccine, 5 mg MSR+200 ug protein+100 ug CpG+1 ug GM-CSF, immunize on day 0; boost on day 14; serum from day 28. For direct conjugation, 200 ug protein conjugated to ~5 ug CpG (primary immunization); boost (100 ug protein conjugated to ~5 ug CpG+ addavax (100 ul)+GM-CSF (1 ug); immunize on day 0; boost on day 21; serum from day 28.
Figure 17:
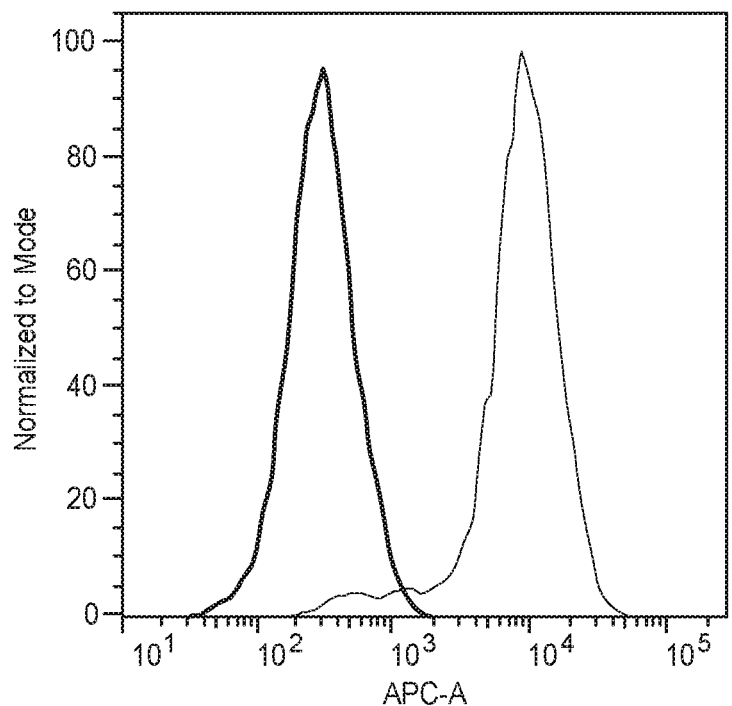
Figure 18A:
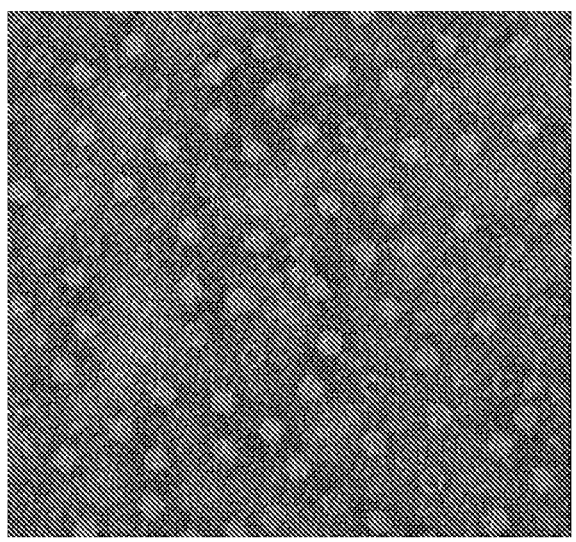
FIG. 18A is an electron micrograph of purified MICA α3—ferritin nanoparticles.
Figure 18B:
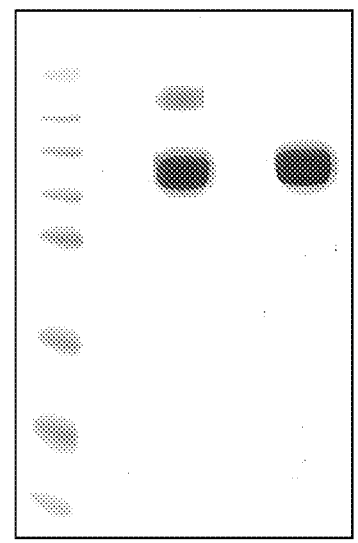
FIG. 18B is a picture of SDS-PAGE of vaccine protein following affinity and gel filtration chromatography.
Figure 19:
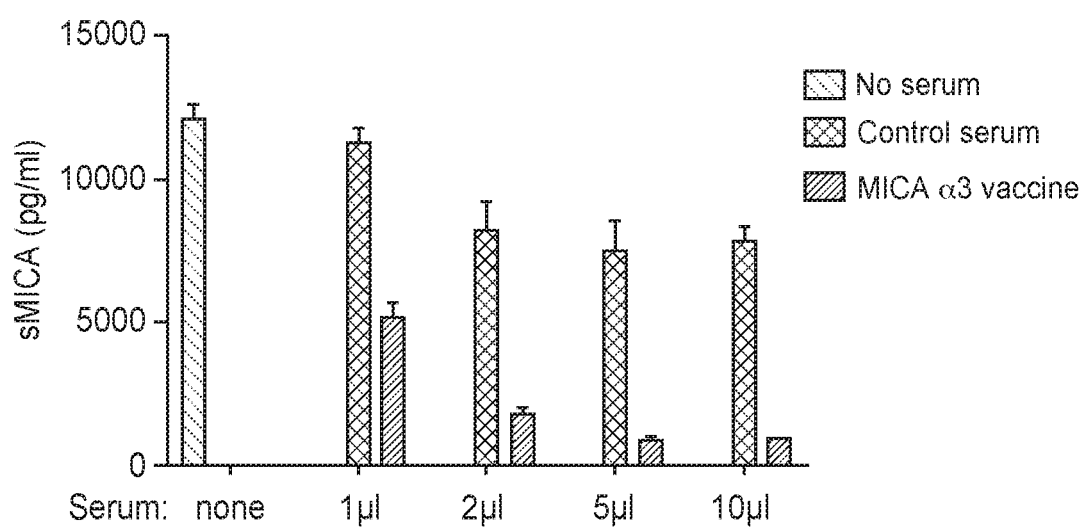
FIG. 19 is a graph showing that polyclonal antibodies induced by MICA α3 domain vaccine inhibit MICA shedding by human tumor cells. MICA shedding by the human A375 melanoma cell line was quantified using a sandwich ELISA. Addition of small quantities of sera (1-10 μl) from mice vaccinated with MICA α3—ferritin strongly inhibited shedding while addition of sera from control mice had little effect.
Figure 21A:
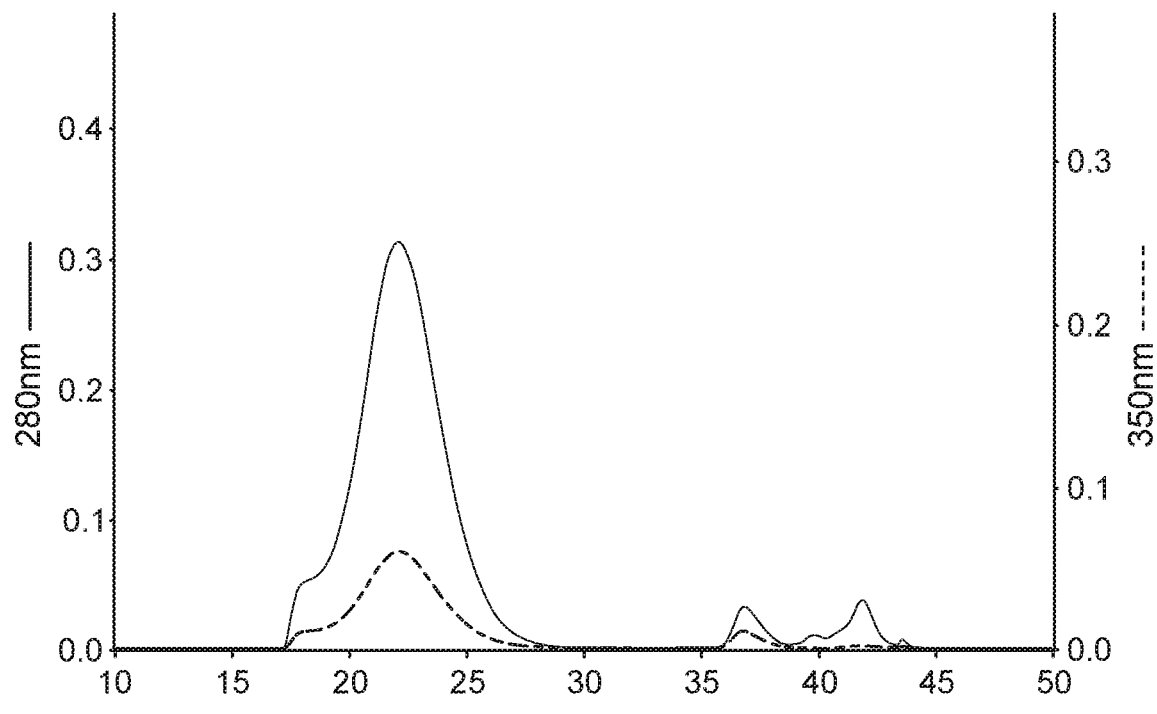
FIGS. 21A-21B are graphs showing immunization with MICA-ferritin nanoparticles conjugated with CpG induces high-titer antibodies.
Figure 21B:
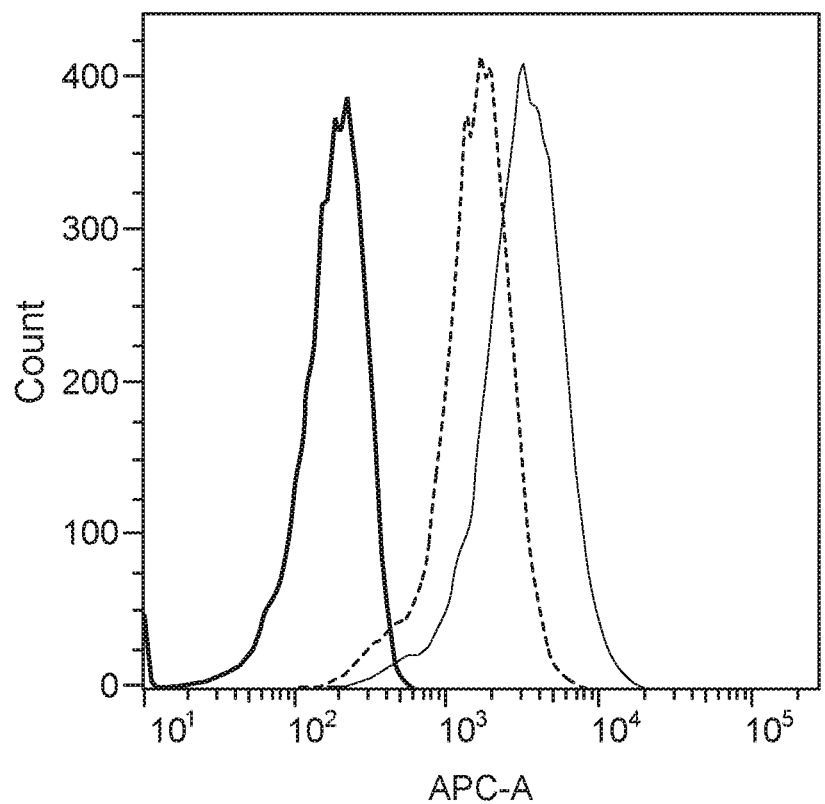

Example 8: MICAa3 Vaccine Alone (without Ferritin Fusion) Shows Significant Therapeutic Benefit In Vivo For these studies, 8 week old C57B1/6J female mice were immunized with MICAα3 vaccine or bolus consisting of all the vaccine components but without the MSR scaffold. Untreated, age matched C57B1/6J female mice were used as the control group. Three weeks after the boost, mice were challenged with i.v. injection of $0.5\times10^6$ MICA expressing B16F10 melanoma cells. Mice were euthanized 14 days after tumor challenge; lungs were harvested and fixed in 10% neutral-buffered formalin and the number of pulmonary metastases was quantified. MICAα3 vaccinated mice were nearly tumor free compared to untreated, age matched control group. The number of pulmonary metastases was significantly lower in the bolus group (~100-125) compared to the non-immunized group (~200-250) (See FIG. 11A).

sMICA was undetectable in sera of mice immunized with MICAα3 vaccine (triangle) while elevated levels of sMICA was found in the untreated control group within two weeks after tumor challenge (circle). The bolus group had relatively lower levels of sMICA in the sera (square) compared to the control group. (See FIG. 11B). The increased number of lung metastases and sMICA levels in mice immunized with MICAα3 bolus compared to the vaccinated group is most likely due to observed levels of reduction in MICA specific antibody titers by day 62 following initial immunization compared to the vaccinated group (data not shown).

Example 9: Determining Cytotoxic Lymphocyte Populations that are Required for Vaccine Efficacy By depleting CD8 T cells or NK cells with mAbs, it was found that both CD8 T cells and NK cells contribute to the therapeutic effect of the vaccine (FIGS. 13A-13B and 14A-14B).

Example 10: ELISA Assay for Quantification of MIC Antibodies

Figure 6:
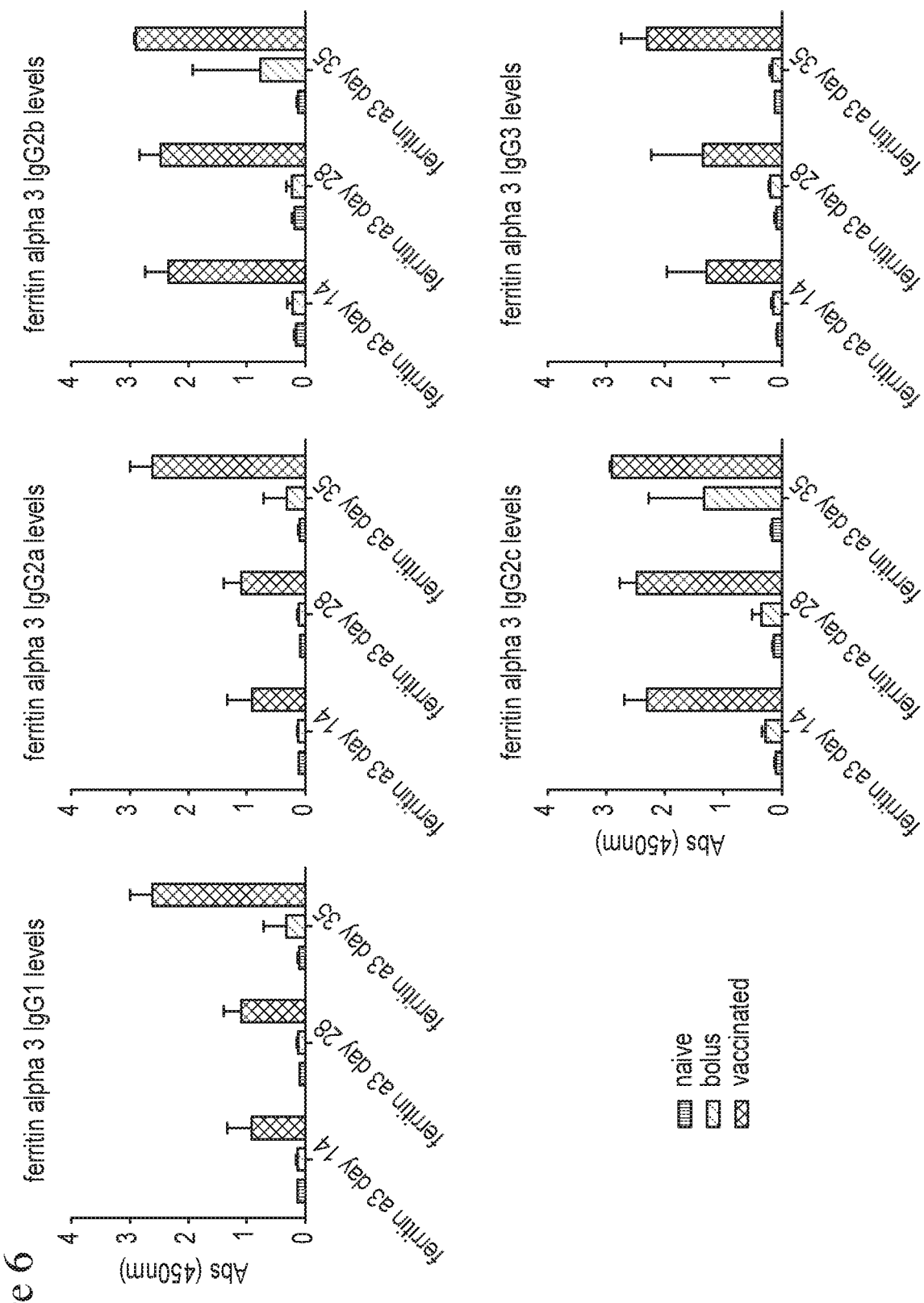
FIG. 6 is a series of graphs that depict tested sera from MICA-ferritin immunized mice that were assayed by ELISA to determine the different subclasses of IgGs induced upon vaccination.

An ELISA assay for quantification of MIC antibodies induced by the vaccine is used (FIG. 6).

Example 11: Future Studies

The following are future studies to be performed to further assess vaccine performance.

1. Vaccine formulations will be optimized by testing the optimal amount of antigen and comparing two adjuvants, CpG oligonucleotide and Poly(I:C).

2. The efficacy of the vaccine will be tested in multiple tumor models, specifically the B16-MIC melanoma model (both subcutaneous and metastasis models) and the orthotopic TRAMP-MIC model of prostate cancer. These studies involve measurement of vaccine efficacy by assessing the inhibition of tumor growth and the reduction of shed MIC in the serum.

3. Sera will be transferred from immunized mice to non-immunized recipients to examine if the induced MIC-specific antibodies are sufficient for the protection afforded by the vaccine.

4. Determination of whether the vaccine provides protection against secondary challenge by tumor cells that lack MIC expression due to induction of a CD8 T cell response against other tumor antigens. Mice that survive the B16-MIC metastasis model will be challenged by i.v. injection of a high dose of B16 tumor cells that express or do not express MIC.

Further investigations of the biomarkers that reflect the mechanistic activity of induced antibodies will be performed. These will include the following approaches.

1. ELISA assay for shed MIC in serum; an assay is available and will be rigorously tested with serum samples from patients with advanced cancer.

2. Testing of functional activity of induced MIC α3 domain antibodies. Which human tumor cell lines are optimal for assays that assess antibody-mediated inhibition of MIC shedding (a panel of cell lines is available) will be studied.

3. Flow cytometry analysis of immune cells in peripheral blood and tumor biopsies. Particularly important is the quantification of surface NKG2D levels by CD8 T cells and NK cells; antibodies are available and the panel will be optimized.

Example 12: Baculovirus Expression of MICA002 Alpha 3 Fused to Ferritin (*H. Pylori*)

```
Purpose: Insect cell expression of MICA (002) alpha 3 fused to ferritin
                                nanoparticle General design:
Signal peptide, 6 his

| | |
|---|---|
| | Purpose: Insect cell expression of MICA (002) alpha 3 fused to ferritin nanoparticle |
| 601 | GCTAAGAAACTGATCATTTTCCTGAATGAGAACAATGTGCCAGTCCAGCTGACTAGCATT |
| 201 | A K K L I I F L N E N N V P V Q L T S I |
| 661 | TCCGCACCCGAACACAAGTTCGAGGGCCTGACCCAGATCTTTCAGAAAGCCTACGAACAC |
| 221 | S A P E H K F E G L T Q I F Q K A Y E H |
| 721 | GAGCAGCATATCTCTGAAAGTATCAACAACATCGTGGACCACGCAATCAAGAGCAAAGAT |
| 241 | E Q H I S E S I N N I V D H A I K S K D |
| 781 | CATGCCACCTTCAACTTTCTGCAGTGGTACGTGGCCGAGCAGCACGAGGAAGAGGTCCTG |
| 261 | H A T F N F L Q W Y V A E Q H E E E V L |
| 841 | TTTAAGGACATTCTGGATAAAATCGAACTGATTGGCAATGAGAATCACGGGCTGTACCTG |
| 281 | F K D I L D K I E L I G N E N H G L Y L |
| 901 | GCAGATCAGTATGTCAAGGGCATCGCAAAGTCAAGGAAATCATGA (SEQ ID NO: 6) |
| 301 | A D Q Y V K G I A K S R K S * (SEQ ID NO: 7) |

SEQ DNAMAN: 945 bp;
Composition 254 A; 252 C; 241 G; 198 T; 0 OTHER
Percentage: 26.9% A; 26.7% C; 25.5% G; 21.0% T; 0.0% OTHER
Molecular Weight (kDa): ssDNA: 291.81 dsDNA: 582.6
ORIGIN

| 1 | ATGGTCCCCT GTACCCTGCT GCTGCTGCTG GCTGCTGCAC TGGCACCTAC TCAGACTCGG |
|---|---|
| 61 | GCCCACCATC ATCACCATCA CTCAAAAAGT TACCCCTACG ATGTCCCCGA CTACGCCAGG |
| 121 | ACCGTGCCCC CTATGGTGAA CGTCACACGC TCAGAAGCTA GCGAGGGCAA TATCACCGTG |
| 181 | ACATGCCGAG CATCTGGGTT CTATCCTTGG AACATTACAC TGAGTTGGAG GCAGGACGGG |
| 241 | GTGTCCCTGT CTCACGATAC TCAGCAGTGG GGCGACGTGC TGCCAGATGG CAATGGGACC |
| 301 | TACCAGACAT GGGTGGCTAC TCGGATCTCC CAGGGGGAGG AACAGAGATT CACCTGCTAT |
| 361 | ATGGAGCATA GTGGAAACCA CTCAACACAT CCTGTGCCAT CTGGCAAGGT GCTGGTCCTG |
| 421 | CAGAGTCACT GGCAGACATT TCATGGATCA GGCGATATCA TTAAGCTGCT GAACGAACAG |
| 481 | GTGAACAAGG AGATGCAGTC TAGTAACCTG TACATGAGCA TGTCAAGCTG GTGTTATACA |
| 541 | CACTCCCTGG ACGGAGCCGG CCTGTTCCTG TTTGATCACG CCGCTGAGGA ATACGAACAT |
| 601 | GCTAAGAAAC TGATCATTTT CCTGAATGAG AACAATGTGC CAGTCCAGCT GACTAGCATT |
| 661 | TCCGCACCCG AACACAAGTT CGAGGGCCTG ACCCAGATCT TTCAGAAAGC CTACGAACAC |
| 721 | GAGCAGCATA TCTCTGAAAG TATCAACAAC ATCGTGGACC ACGCAATCAA GAGCAAAGAT |
| 781 | CATGCCACCT TCAACTTTCT GCAGTGGTAC GTGGCCGAGC AGCACGAGGA AGAGGTCCTG |
| 841 | TTTAAGGACA TTCTGGATAA AATCGAACTG ATTGGCAATG AGAATCACGG GCTGTACCTG |
| 901 | GCAGATCAGT ATGTCAAGGG CATCGCAAAG TCAAGGAAAT CATGA (SEQ ID NO: 8) |

Step 1. Amplify template for PCR 1 (signal peptide, 6 his, linker, HA, MICA alpha3) from C1347 construct using primers
Forward primer# ferritin_baculo_SmaIfor
5' AAAAAACCCGGGATGGTCCCCTGTACCCTGCTGCTGCTGC 3'(SEQ ID NO: 9)

Internal reverse primer: # ferritin baculo_IRev
5' GTTCGTTCAGCAGCTTAATGATATCGCCTGATCCATGAAATGTCTGCCAG 3' (SEQ ID NO: 10)

Step 2. Amplify template for PCR 2 (ferritin) from C1347 using
Internal forward primer: # ferritin baculo_IF
5' CTGGCAGACATTTCATGGATCAGGCGATATCATTAAGCTGCTGAACGAAC 3' (SEQ ID NO: 11)

Reverse primer: # ferritin baculo_BamHIRev
5' AAAAAAGGATCCTCATGATTTCCTTGACTTTGCGATGCCCTTG 3' (SEQ ID NO: 12)

-continued

Purpose: Insect cell expression of MICA (002) alpha 3 fused to ferritin nanoparticle

```
Step 3: Fusion PCR using primers
# ferritin baculo_SmaIfor
and
# ferritin baculo_BamHIRev
Restriction analysis on DNAMAN18
Methylation: dam-No dcm-No
Screened with 117 enzymes, 18 sites found ApaI                        1                    GGGCC/C
                           63
BclI                        2                    T/GATCA
                          573                    611
BglII                       1                    A/GATCT
                          695
BsiI                        2                    C/TCGTG
                          718                    823
Bsp1407I                    1                    T/GTACA
                          509
BspHI                       1                    T/CATGA
                          940
BspMI                       1                    ACCTGCNNNN/ (SEQ ID NO: 13)
                          361
Eam1105I                    1                    GACNNN/NNGTC (SEQ ID NO: 14)
                          240
Eco56I                      1                    G/CCGGC
                          556
EcoNI                       1                    CCTNN/NNNAGG (SEQ ID NO: 15)
                          841
EcoRV                       1                    GAT/ATC
                          456
NaeI                        1                    GCC/GGC
                          558
NheI                        1                    G/CTAGC
                          157
PstI                        2                    CTGCA/G
                          422                    803
PvuII                       1                    CAG/CTG
                          648
List by Site Order
63        ApaI          456       EcoRV         611      BclI         803  PstI
157       NheI          509       Bsp1407I      648      PvuII        823  BsiI
240       Eam1105I      556       Eco56I        695      BglII        841  EcoNI
361       BspMI         558       NaeI          718      BsiI         940  BspHI
422       PstI          573       BclI
Non Cut Enzymes
AatII       Acc65I      AccIII      AclI        AflII       AgeI
AhaIII      Alw44I      AlwNI       ApaBI       ApaLI       AscI
Asp718I     AsuII       AvrII       BalI        BamHI       BbeI
BbvII       BglI        Bpu1102I    Bsc91I      BsmI        BspMII
BssHII      BstD102I    BstEII      BstXI       Bsu36I      ClaI
Csp45I      CspI        CvnI        DraI        DraIII      DrdI
EagI        Ecl136II    Eco31I      Eco47III    Eco52I      Eco57I
Eco72I      EcoICRI     EcoRI       EheI        EspI        FseI
HindIII     HpaI        I-PpoI      KpnI        MfeI        Mlu113I
MluI        MscI        MstI        MstII       NarI        NcoI
NdeI        NotI        NruI        NsiI        PacI        Pf1MI
PinAI       PmaCI       PmeI        PvuI        RleAI       SadI
SacII       SalI        SapI        SauI        ScaI        SciI
SfiI        SgrAI       SmaI        SnaBI       SpeI        SphI
SplI        SpoI        SrfI        SspI        SstI        SstII
StuI        SunI        SwaI        Tth111I     VspI        XbaI
XcmI        XhoI        XmaI        XmaIII      XmnI        XorII Ferritin from H. Pylori
MLSKDIIKLLNEQVNKEMQSSNLYMSMSSWCYTHSLDGAGLFLFDHAAEEYEHAKKLIIF

LNENNVPVQLTSISAPEHKFEGLIQIFQKATEHEQHISESINNIVDHAIKSKDHATENFL

QWYVAEQHEEEVLFKDILDKIELIGNENHGLYLADQYVKGIAKSRKS 181 (SEQ ID NO: 16)
```

Purpose: Insect cell expression of MICA (002) alpha 3 fused to ferritin nanoparticle Position N19 changed to Q (to eliminate N-linked glycosylation site),
start at position 5 (underlined)
ferritin [*Helicobacter pylori*]
NCBI Reference Sequence: WP_000949190.1
FASTA Graphics
Go to:
LOCUS  WP_000949190  167 aa  linear  BCT
16-MAY-2013
```
DEFINITION          ferritin [Helicobacter pylori].
ACCESSION           WP_000949190
VERSION             WP_000949190.1  GI:446871934
KEYWORDS            RefSeq.
SOURCE              Helicobacter pylori
ORGANISM            Helicobacter pylori
                    Bacteria; Proteobacteria; Epsilonproteobacteria;
                    Campylobacterales;
                    Helicobacteraceae; Helicobacter.
COMMENT             REFSEQ: This record represents a single, non-redundant,
                    protein
genomes             sequence which may be annotated on many different RefSeq
                    from the same, or different, species.
                    COMPLETENESS: full length.
FEATURES            Location/Qualifiers
source              1..167
                    /organism="Helicobacter pylori"
                    /db xref="taxon:210"
Protein             1..167
                    /product="ferritin"
                    /calculated mol wt=19183
Region              3..158
                    /region name="Nonheme Ferritin"
                    /note="nonheme-containing ferritins; cd01055"
                    /db xref="CDD:153113"
Region              7..144
                    /region name="Ferritin"
                    /note="Ferritin-like domain; pfam00210"
                    /db xref="CDD:249681"
Site                order(17,49..50,53,94,126,129..130)
                    /site type="other"
                    /note="ferroxidase diiron center [ion binding]"
                    /db xref="CDD:153113"

ORIGIN
    1               mlskdiikll negvnkemns snlymsmssw cythsldgag lflfdhaaee
                    yehakkliif
   61               lnennvpvql tsisapehkf egltgifqka yeheqhises innivdhaik
                    skdhatfnfl
  121               gwyvaeghee evlfkdildk ielignenhg lyladqyvkg iaksrks (SEQ ID NO: 17)
```

45

Example 11: Deglycosylated MICA 002 Protein Expression in Insect Cells

Purpose: Baculovirus expression of deglycosylated MICA alpha 3 (*002:01)

General design:
Signal peptide, N-terminal HA peptide, MICA alpha 3 domain (*002:01), stop codon
```
    1   MVPCTLLLLL AAALAPTQTR ASKSYPYDVP DYARTVPPMV QVTRSEASEG QITVTCRASG
        signal peptide, HA
   61   FYPWNINLSW RQDGVSLSHD TQQWGDVLPD GNGTYQTWVA TRISQGEEQR FTCYMEHSGQ  MICA
        alpha 3
  121   HSTHPVPSGK VLVLQSHWQT FH* stop (SEQ ID NO: 25)
```

Strategy: Clone into pAcDB3 BglII-EcoRI site

SEQ DNAMAN1: 432 bp;
Composition 96 A; 125 C; 122 G; 89 T; 0 OTHER
Percentage: 22.2% A; 28.9% C; 28.2% G; 20.6% T; 0.0% OTHER
Molecular Weight (kDa): ssDNA: 133.37 dsDNA: 266.4
ORIGIN
```
    1   ATGGTCCCCT GTACCCTGCT GCTGCTGCTG GCTGCTGCAC TGGCACCTAC TCAGACTCGG
   61   GCCTCAAAAA GTTACCCCTA CGATGTCCCC GACTACGCCA GGACCGTGCC CCCTATGGTG
```

```
    121 CAGGTCACAC GCTCAGAAGC TAGCGAGGGC CAAATCACCG TGACATGCCG AGCATCTGGG
    181 TTCTATCCTT GGAACATTAA CCTGAGTTGG AGGCAGGACG GGGTGTCCCT GTCTCACGAT
    241 ACTCAGCAGT GGGGCGACGT GCTGCCAGAT GGCAATGGGA CCTACCAGAC ATGGGTGGCT
    301 ACTCGGATCT CCCAGGGGGA GGAACAGAGA TTCACCTGCT ATATGGAGCA TAGTGGACAG
    361 CACTCAACAC ATCCTGTGCC ATCTGGCAAG GTGCTGGTCC TGCAGAGTCA CTGGCAGACA
    421 TTTCATTGA (SEQ ID NO: 18)
```

Translation of DNAMAN1(1-432)
Universal code
Total amino acid number: 143, MW = 15928
Max ORF: 1-429, 143 AA, MW = 15928

```
      1 ATGGTCCCCTGTACCCTGCTGCTGCTGCTGGCTGCTGCACTGGCACCTACTCAGACTCGG
      1 M  V  P  C  T  L  L  L  L  L  A  A  A  L  A  P  T  Q  T  R

61 GCCTCAAAAAGTTACCCCTACGATGTCCCCGACTACGCCAGGACCGTGCCCCCTATGGTG
     21 A  S  K  S  Y  P  Y  D  V  P  D  Y  A  R  T  V  P  P  M  V

121 CAGGTCACACGCTCAGAAGCTAGCGAGGGCCAAATCACCGTGACATGCCGAGCATCTGGG
     41 Q  V  T  R  S  E  A  S  E  G  Q  I  T  V  T  C  R  A  S  G

181 TTCTATCCTTGGAACATTAACCTGAGTTGGAGGCAGGACGGGGTGTCCCTGTCTCACGAT
     61 F  Y  P  W  N  I  N  L  S  W  R  Q  D  G  V  S  L  S  H  D

241 ACTCAGCAGTGGGGCGACGTGCTGCCAGATGGCAATGGGACCTACCAGACATGGGTGGCT
     81 T  Q  Q  W  G  D  V  L  P  D  G  N  G  T  Y  Q  T  W  V  A

301 ACTCGGATCTCCCAGGGGGAGGAACAGAGATTCACCTGCTATATGGAGCATAGTGGACAG
    101 T  R  I  S  Q  G  E  E  Q  R  F  T  C  Y  M  E  H  S  G  Q

361 CACTCAACACATCCTGTGCCATCTGGCAAGGTGCTGGTCCTGCAGAGTCACTGGCAGACA
    121 H  S  T  H  P  V  P  S  G  K  V  L  V  L  Q  S  H  W  Q  T

421 TTTCATTGA  (SEQ ID NO: 19)
    141 F  H  *   (SEQ ID NO: 20)
```

Restriction analysis on DNAMAN1
Methylation: dam-No dcm-No
Screened with 117 enzymes, 5 sites found
```
        BspMI      2  ACCTGCNNNN/(SEQ ID NO: 21)
                   343        111
        Eam1105I   1  GACNNN/NNGTC (SEQ ID NO: 22)
                   222
        NheI       1  G/CTAGC
                   139
        PstI       1  CTGCA/G
                   404
```

List by Site Order
```
111      BspMI        222       Eam1105I      343       BspMI        404        PstI
139      NheI
```

Non Cut Enzymes
```
AatII        Acc65I       AccIII       AclI         AflII        AgeI
AhaIII       Alw44I       AlwNI        ApaBI        ApaI         ApaLI
AscI         Asp718I      AsuII        AvrII        BalI         BamHI
BbeI         BbvII        BclI         BglI         BglII        Bpu1102I
Bsc91I       BsiI         BsmI         Bsp1407I     BspHI        BspMII
BssHII       BstD102I     BstEII       BstXI        Bsu36I       ClaI
Csp45I       CspI         CvnI         DraI         DraIII       DrdI
EagI         Ecl136II     Eco31I       Eco47III     Eco52I       Eco56I
Eco57I       Eco72I       EcoICRI      EcoNI        EcoRI        EcoRV
EheI         EspI         FseI         HindIII      HpaI         I-PpoI
KpnI         MfeI         Mlu113I      MluI         MscI         MstI
MstII        NaeI         NarI         NcoI         NdeI         NotI
NruI         NsiI         PacI         PflMI        PinAI        PmaCI
PmeI         PvuI         PvuII        RleAI        SacI         SacII
SalI         SapI         SauI         ScaI         SciI         SfiI
SgrAI        SmaI         SnaBI        SpeI         SphI         SplI
SpoI         SrfI         SspI         SstI         SstII        StuI
SunI         SwaI         Tth111I      VspI         XbaI         XcmI
XhoI         XmaI         XmaIII       XmnI         XorII
```

4099: MICA002_baculo_BglIIfor
5' AAAAAAAGATCTATGGTCCCCTGTACCCTGCTGCTGCTGC 3' (SEQ ID NO: 23)

4100: MICA002_baculo_EcoRIRev
5'AAAAAAGAATTCTCAATGAAATGTCTGCCAGTGACTCTGC 3'(SEQ ID NO: 24)

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

```

What is claimed is:

1. A fusion protein comprising a monomeric ferritin subunit protein fused to a MIC alpha 3-domain protein, wherein the monomeric ferritin subunit protein comprises a domain that allows the fusion protein to self-assemble into nanoparticles, wherein the MIC alpha-3 domain protein comprises the amino acid sequence of SEQ ID NO: 3 or SEQ ID NO: 4 or an amino acid sequence that is at least 90% identical thereto.

2. The fusion protein of claim 1, wherein the monomeric ferritin subunit protein is a monomeric subunit of a *Helicobacter pylori* ferritin protein.

3. The fusion protein of claim 1, further comprising a Cytosine-Guanosine (CpG) oligonucleotide sequence.

4. A nanoparticle comprising the fusion protein of claim 1.

5. An immunogenic composition comprising the nanoparticle of claim 4.

6. The immunogenic composition of claim 5 further comprising GM-CSF.

7. The fusion protein of claim 1, wherein the MIC alpha-3 domain protein comprises the amino acid sequence of SEQ ID NO: 3 or SEQ ID NO: 4.

8. A nanoparticle comprising the fusion protein of claim 7.

9. A vaccine comprising the nanoparticle of claim 8.

10. A method of immunizing a mammalian subject comprising administering to the subject the vaccine of claim 9 in an amount effective to elicit an immune response against the MIC alpha-3 domain protein in the subject.

11. The method of claim 10, further comprising administering GM-CSF or one or more vaccines specific for an antigen other than a MIC alpha-3 domain antigen.

12. The method of claim 10, wherein the subject has a cancer associated with overexpression of major histocompatibility complex (MHC) class I chain-related protein A (MICA).

13. The method of claim 12, wherein the vaccine composition is administered as part of a therapeutic regimen.

14. The method of claim 13, wherein the therapeutic regimen is radiation therapy, targeted therapy, immunotherapy, or chemotherapy.

15. The method of claim 12, wherein the subject has tested positive for shed serum MICA.

* * * * *